United States Patent
Saito et al.

(10) Patent No.: US 9,502,667 B2
(45) Date of Patent: Nov. 22, 2016

(54) ORGANIC ELECTROLUMINESCENCE

(71) Applicant: IDEMITSU KOSAN CO., LTD., Chiyoda-ku (JP)

(72) Inventors: Masatoshi Saito, Chiba (JP); Yumiko Mizuki, Chiba (JP); Kazuki Nishimura, Chiba (JP)

(73) Assignee: IDEMITSU KOSAN CO., LTD., Chiyoda-ku (JP)

(*) Notice: Subject to any disclaimer, the term of this patent is extended or adjusted under 35 U.S.C. 154(b) by 340 days.

(21) Appl. No.: 14/163,397

(22) Filed: Jan. 24, 2014

(65) Prior Publication Data

US 2016/0163998 A1 Jun. 9, 2016

(30) Foreign Application Priority Data

Jan. 24, 2013 (JP) .................. 2013-011403
Jan. 24, 2014 (JP) .................. 2014-011255

(51) Int. Cl.
| | | |
|---|---|---|
| H01L 51/00 | (2006.01) | |
| C07D 487/06 | (2006.01) | |
| C09K 11/02 | (2006.01) | |
| C09K 11/06 | (2006.01) | |
| H01L 51/50 | (2006.01) | |

(52) U.S. Cl.
CPC ......... *H01L 51/0072* (2013.01); *C07D 487/06* (2013.01); *C09K 11/025* (2013.01); *C09K 11/06* (2013.01); *H01L 51/0058* (2013.01); *H01L 51/0061* (2013.01); *H01L 51/0067* (2013.01); *H01L 51/0085* (2013.01); *C09K 2211/1029* (2013.01); *C09K 2211/185* (2013.01); *H01L 51/5012* (2013.01); *H01L 51/5016* (2013.01)

(58) Field of Classification Search
CPC .................................................. H01L 51/0055
See application file for complete search history.

(56) References Cited

U.S. PATENT DOCUMENTS

| | | | |
|---|---|---|---|
| 2010/0283043 A1* | 11/2010 | Nishimura et al. ............ 257/40 |
| 2011/0278552 A1* | 11/2011 | Numata et al. ................. 257/40 |
| 2012/0223295 A1* | 9/2012 | Inoue et al. .................... 257/40 |
| 2014/0001451 A1* | 1/2014 | Mizuki et al. ................. 257/40 |

FOREIGN PATENT DOCUMENTS

WO 03/080760 10/2003

OTHER PUBLICATIONS

Von Dieter Hellwinkel, et al., "Zur Frage des pentakoordinierten Stickstoffs: Reaktionen von (spiro)cyclischen Tetraarylammonium-Salzen mit Nucleophilen", Liebigs Ann. Chem. 762, 29-54 (1972).

* cited by examiner

*Primary Examiner* — Mohammad Islam
*Assistant Examiner* — Ankush Singal
(74) *Attorney, Agent, or Firm* — Oblon, McClelland, Maier & Neustadt, L.L.P.

(57) ABSTRACT

A nitrogen-containing heterocyclic compound wherein a pyrrole ring, an aromatic ring and a 7-membered ring are fused one another, a material for organic electroluminescence device including the compound, and an organic electroluminescence device including the material.

18 Claims, 1 Drawing Sheet

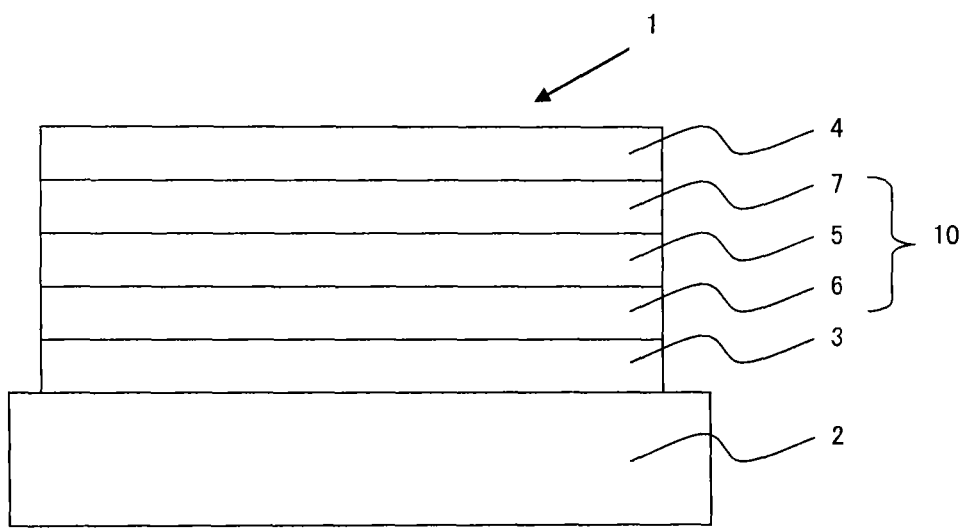

ORGANIC ELECTROLUMINESCENCE

CROSS-REFERENCE TO RELATED APPLICATION

This application is based upon and claims the benefit of priority from the prior Japanese Patent Application No. 2013-011403, filed on Jan. 24, 2013; the entire contents of which are incorporated herein by reference.

TECHNICAL FIELD

The present invention relates to materials for organic electroluminescence device, organic electroluminescence devices employing the material, and nitrogen-containing heterocyclic compounds.

BACKGROUND ART

An organic electroluminescence (EL) device is generally composed of an anode, a cathode, and one or more organic thin film layers sandwiched between the anode and the cathode. When a voltage is applied between the electrodes, electrons are injected from the cathode and holes are injected from the anode into a light emitting region. The injected electrons recombine with the injected holes in the light emitting region to form excited states. When the excited states return to the ground state, the energy is released as light.

Many researches have been made on the applications of organic EL device to display, etc. because of its possibility of a wide selection of emission colors by using various emitting materials in a light emitting layer. Particularly, the research on the materials which emit three primary red, green, blue colors has been made most actively, and the intensive research has been made to improve their properties.

One of the most important issues in the organic EL device is to achieve both high emission efficiency and low driving voltage. It has been known that a highly efficient light-emitting device is obtained by a light emitting layer wherein a several percent of a dopant material is doped into a host material. The host material is required to have a high carrier mobility and a uniform film-forming property, and the dopant material is required to have a high fluorescent quantum yield and a uniform dispersibility.

Patent Document 1 discloses a compound having a carbazole skeleton as the material for such a light emitting layer. Non-patent Document 1 discloses a compound wherein a 7-membered ring is fused to a carbazole structure, however, teaches or suggests nothing about its use as the material for organic EL device.

PRIOR ART

Patent Document

Patent Document 1: WO 2003/080760

Non-Patent Document

Non-patent Document 1: Justus Liebigs Annalen der Chemie, 1972, 762, 29

SUMMARY OF THE INVENTION

In an aspect, the invention provides:
1. a material for organic electroluminescence device comprising a nitrogen-containing heterocyclic compound A represented by formula (1):

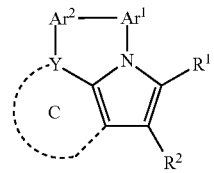

(1)

wherein:
each of $R^1$ and $R^2$ independently represents a hydrogen atom or a group;
when both $R^1$ and $R^2$ represent the groups, $R^1$ and $R^2$ may be bonded to each other to form a ring structure;
each of $Ar^1$ and $Ar^2$ independently represents a substituted or unsubstituted arylene group having 6 to 50 ring carbon atoms or a substituted or unsubstituted heteroarylene group having 5 to 50 ring atoms;
one of ring atoms of $Ar^1$ is bonded to $Ar^2$, and another ring atom of $Ar^1$ which is adjacent to the ring atom bonded to $Ar^2$ is bonded to a nitrogen atom shown in formula (1);
one of ring atoms of $Ar^2$ is bonded to $Ar^1$, and another ring atom of $Ar^2$ which is adjacent to the ring atom bonded to $Ar^1$ is bonded to Y shown in formula (1);
Y represents a carbon atom or a nitrogen atom; and
C represents a substituted or unsubstituted aromatic hydrocarbon ring or a substituted or unsubstituted aromatic heterocyclic ring;
2. an organic electroluminescence device comprising one or more organic thin film layers disposed between a cathode and an anode, wherein the organic thin film layers comprises a light emitting layer, and at least one layer of the organic thin film layers comprises the material for organic electroluminescence device mentioned above;
3. a nitrogen-containing heterocyclic compound B represented by formula (1'):

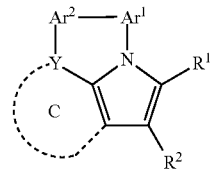

(1')

wherein:
each of $R^1$ and $R^2$ independently represents a hydrogen atom or a group;
when both $R^1$ and $R^2$ represent the groups, $R^1$ and $R^2$ may be bonded to each other to form a ring structure;
each of $Ar^1$ and $Ar^2$ independently represents a substituted or unsubstituted arylene group having 6 to 50 ring carbon atoms or a substituted or unsubstituted heteroarylene group having 5 to 50 ring atoms;
one of ring atoms of $Ar^1$ is bonded to $Ar^2$, and another ring atom of $Ar^1$ which is adjacent to the ring atom bonded to $Ar^2$ is bonded to a nitrogen atom shown in formula (1');
one of ring atoms of $Ar^2$ is bonded to $Ar^1$, and another ring atom of $Ar^2$ which is adjacent to the ring atom bonded to $Ar^1$ is bonded to Y shown in formula (1');
Y represents a carbon atom or a nitrogen atom; and
C represents a substituted or unsubstituted aromatic hydrocarbon ring or a substituted or unsubstituted aromatic heterocyclic ring;

provided that at least one of $R^1$, $R^2$, a substituent on $Ar^1$, a substituent on $Ar^2$, and a substituent on the aromatic hydrocarbon ring or the aromatic heterocyclic ring each represented by C is a group comprising a ring structure or a group comprising a reactive site; and 4. an electronic equipment comprising the organic electroluminescence device mentioned above.

BRIEF DESCRIPTION OF THE DRAWINGS

FIG. 1 is a schematic illustration showing an example of the structure of an organic electroluminescence device (hereinafter also referred to as "organic EL device") according to an embodiment of the invention.

MODE FOR CARRYING OUT THE INVENTION

The carbon number of a to b in the expression of "a substituted or unsubstituted X group having a to b carbon atoms" is the carbon number of the unsubstituted X group and does not include the carbon atom of the substituent of the substituted X group.

The definition of "hydrogen atom" includes isotopes different in the neutron numbers, i.e., light hydrogen (protium), heavy hydrogen (deuterium), and tritium.

The optional substituent referred to by "substituted or unsubstituted" used herein is preferably selected from the group consisting of an alkyl group having 1 to 50, preferably 1 to 18, more preferably 1 to 8 carbon atoms; a cycloalkyl group having 3 to 50, preferably 3 to 10, more preferably 3 to 8, still more preferably 5 or 6 ring carbon atoms; an aryl group having 6 to 50, preferably 6 to 25, more preferably 6 to 18 ring carbon atoms; an aralkyl group having 7 to 51, preferably 7 to 30, more preferably 7 to 20 carbon atoms which has an aryl group having 6 to 50, preferably 6 to 25, more preferably 6 to 18 ring carbon atoms; an amino group; a mono- or di-substituted amino group having a substituent selected from an alkyl group having 1 to 50, preferably 1 to 18, more preferably 1 to 8 carbon atoms and an aryl group having 6 to 50, preferably 6 to 25, more preferably 6 to 18 ring carbon atoms; an alkoxy group having an alkyl group having 1 to 50, preferably 1 to 18, more preferably 1 to 8 carbon atoms; an aryloxy group having an aryl group having 6 to 50, preferably 6 to 25, more preferably 6 to 18 ring carbon atoms; a mono-, di- or tri-substituted silyl group having a substituent selected from an alkyl group having 1 to 50, preferably 1 to 18, more preferably 1 to 8 carbon atoms and an aryl group having 6 to 50, preferably 6 to 25, more preferably 6 to 18 ring carbon atoms; a heterocyclic group having 5 to 50, preferably 5 to 24, more preferably 5 to 13 ring atoms; a haloalkyl group having 1 to 50, preferably 1 to 18, more preferably 1 to 8 carbon atoms; a halogen atom selected from a fluorine atom, a chlorine atom, a bromine atom and an iodine atom; a cyano group; a nitro group; a sulfonyl group having a group selected from an alkyl group having 1 to 50, preferably 1 to 18, more preferably 1 to 8 carbon atoms and an aryl group having 6 to 50, preferably 6 to 25, more preferably 6 to 18 ring carbon atoms; and a di-substituted phosphoryl group having a substituent selected from an alkyl group having 1 to 50, preferably 1 to 18, more preferably 1 to 8 carbon atoms and an aryl group having 6 to 50, preferably 6 to 25, more preferably 6 to 18 ring carbon atoms. The substituents in the exemplary compounds mentioned below are also preferred.

The optional substituent may be further substituted with an optional substituent mentioned above.

Material for Organic Electroluminescence Device

The material for organic electroluminescence device of the invention comprises a nitrogen-containing heterocyclic compound A represented by formula (1):

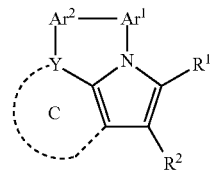

(1)

wherein:
each of $R^1$ and $R^2$ independently represents a hydrogen atom or a group;
when both $R^1$ and $R^2$ represent the groups, $R^1$ and $R^2$ may be bonded to each other to form a ring structure;
each of $Ar^1$ and $Ar^2$ independently represents a substituted or unsubstituted arylene group having 6 to 50 ring carbon atoms or a substituted or unsubstituted heteroarylene group having 5 to 50 ring atoms;
one of ring atoms of $Ar^1$ is bonded to $Ar^2$, and another ring atom of $Ar^1$ which is adjacent to the ring atom bonded to $Ar^2$ is bonded to a nitrogen atom shown in formula (1);
one of ring atoms of $Ar^2$ is bonded to $Ar^1$, and another ring atom of $Ar^2$ which is adjacent to the ring atom bonded to $Ar^1$ is bonded to Y shown in formula (1);
Y represents a carbon atom or a nitrogen atom; and
C represents a substituted or unsubstituted aromatic hydrocarbon ring or a substituted or unsubstituted aromatic heterocyclic ring.

As seen from formula (1), the nitrogen-containing heterocyclic compound A has a 7-membered ring including 7 ring atoms, i.e., the nitrogen atom, two adjacent ring atoms in $Ar^1$, two adjacent ring atoms in $Ar^2$, Y, and the carbon atom linking Y and the nitrogen atom. With such a structure, the whole molecular structure is stabilized to provide a beneficial effect of the invention.

Examples of the basic structure of the nitrogen-containing heterocyclic compound A represented by formula (1) are shown below. The nitrogen-containing heterocyclic compound A may be either a compound including only the following basic structure or a compound including the following basic structure which is substituted with the group mentioned above.

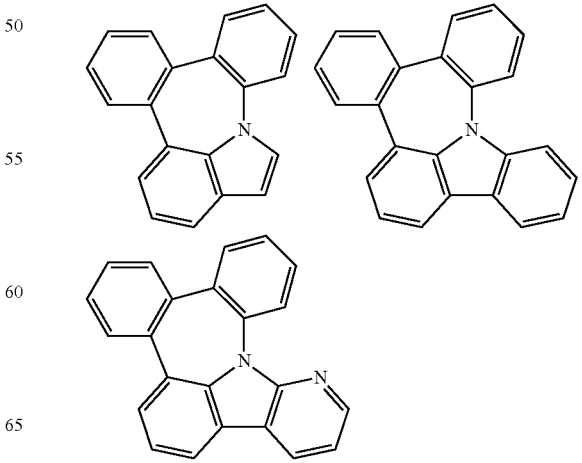

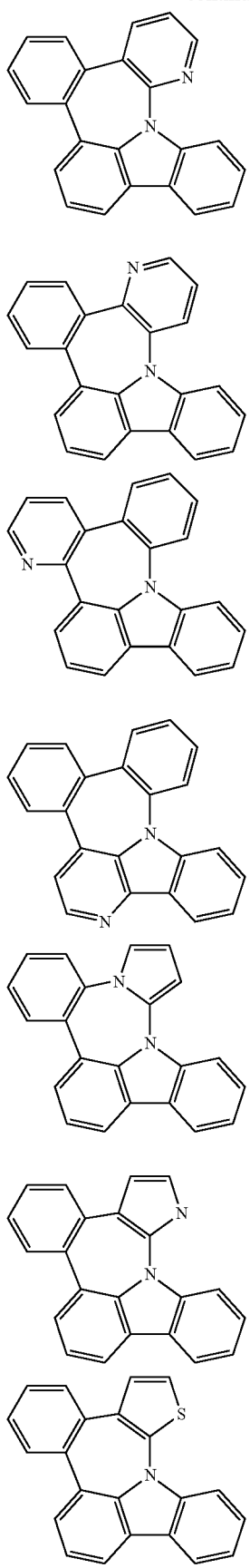
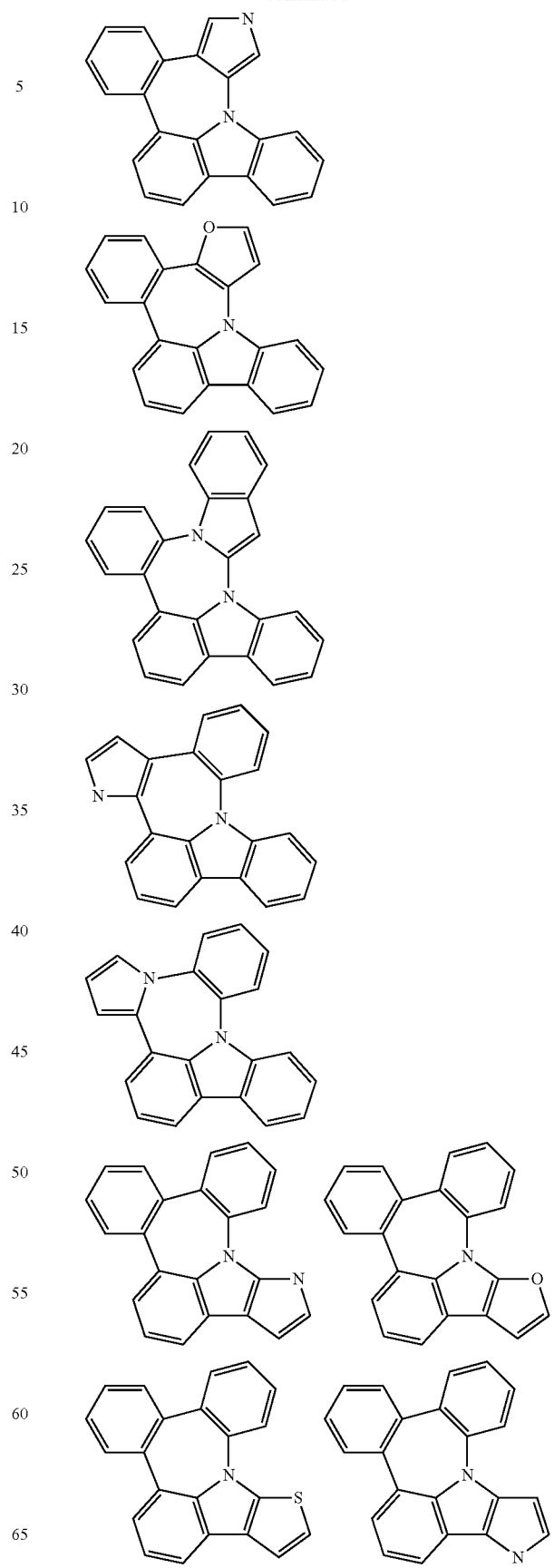

-continued

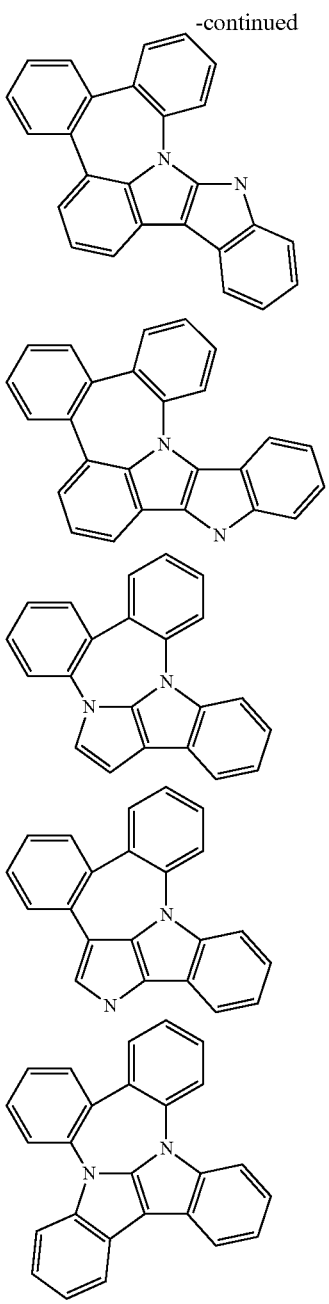

The nitrogen-containing heterocyclic compound A represented by formula (1) may be a polymer represented by formula (1-a):

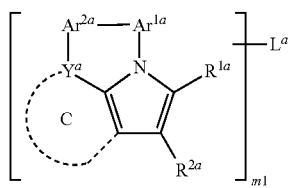

wherein:
each of $R^{1a}$ and $R^{2a}$ independently represents a hydrogen atom or a group;

when both $R^{1a}$ and $R^{2a}$ represent the groups, $R^{1a}$ and $R^{2a}$ may be bonded to each other to form a ring structure;

each of $Ar^{1a}$ and $Ar^{2a}$ independently represents a substituted or unsubstituted arylene group having 6 to 50 ring carbon atoms or a substituted or unsubstituted heteroarylene group having 5 to 50 ring atoms;

one of ring atoms of $Ar^{1a}$ is bonded to $Ar^{2a}$, and another ring atom of $Ar^{1a}$ which is adjacent to the ring atom bonded to $Ar^{2a}$ is bonded to a nitrogen atom shown in formula (1-a);

one of ring atoms of $Ar^{2a}$ is bonded to $Ar^{1a}$, and another ring atom of $Ar^{2a}$ which is adjacent to the ring atom bonded to $Ar^{1a}$ is bonded to $Y^a$ shown in formula (1-a);

$Y^a$ represents a carbon atom or a nitrogen atom;

$C^a$ represents a substituted or unsubstituted aromatic hydrocarbon ring or a substituted or unsubstituted aromatic heterocyclic ring;

m1 represents an integer of 2 to 6; and $L^a$ represents a single bond or an m1-valent linking group which is bonded to any of $R^{1a}$, $R^{2a}$, $Ar^{1a}$, $Ar^{2a}$, and the ring $C^a$.

The nitrogen-containing heterocyclic compound A is preferably represented by formula (2):

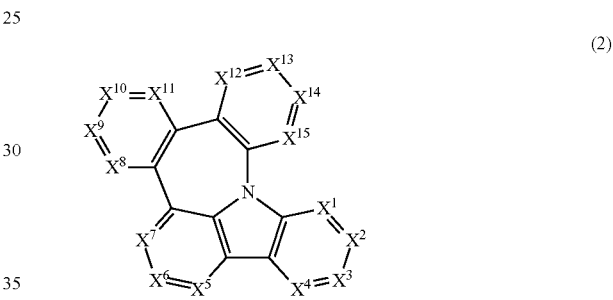

wherein:
each of $X^1$ to $X^{15}$ independently represents C(R) or a nitrogen atom;

R represents a hydrogen atom or a group; and when two or more of $X^1$ to $X^{15}$ have the group, the groups may be bonded to each other to form a ring structure.

The nitrogen-containing heterocyclic compound A represented by formula (2) may be a polymer represented by formula (2-a):

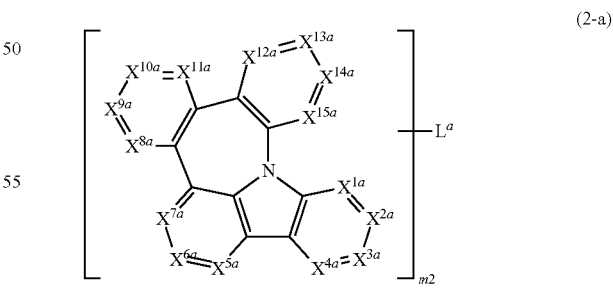

wherein:
each of $X^{1a}$ to $X^{15a}$ independently represents C(R) or a nitrogen atom;

R represents a hydrogen atom or a group;

when two or more of $X^{1a}$ to $X^{15a}$ have the groups, the groups may be bonded to each other to form a ring structure;

m2 represents an integer of 2 to 6; and $L^a$ represents a single bond or an m2-valent linking group which is bonded to any of $X^{1a}$ to $X^{15a}$.

The nitrogen-containing heterocyclic compound A is more preferably represented by formula (3):

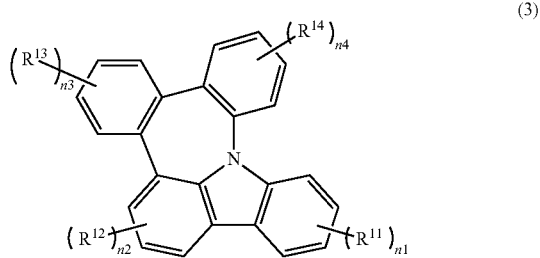

(3)

wherein:
each of $R^{11}$ to $R^{14}$ independently represents a group;
each of n1, n3, and n4 independently represents an integer of 0 to 4;
n2 represents an integer of 0 to 3;
when n1 represents 2 to 4, $R^{11}$ groups may be the same or different, and $R^{11}$ groups may be bonded to each other to form a ring structure;
when n2 represents 2 or 3, $R^{12}$ groups may be the same or different, and $R^{12}$ groups may be bonded to each other to form a ring structure;
when n3 represents 2 to 4, $R^{13}$ groups may be the same or different, and $R^{13}$ groups may be bonded to each other to form a ring structure; and
when n4 represents 2 to 4, $R^{14}$ groups may be the same or different, and $R^{14}$ groups may be bonded to each other to form a ring structure.

The nitrogen-containing heterocyclic compound A represented by formula (3) may be a polymer represented by formula (3-a):

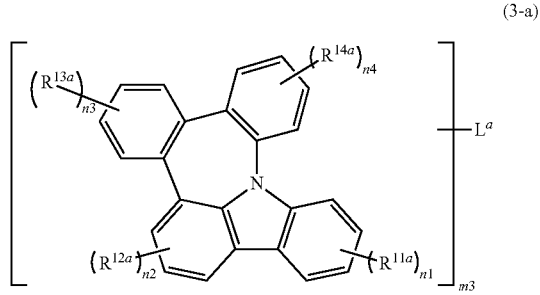

(3-a)

wherein:
each of $R^{11a}$ to $R^{14a}$ independently represents a group;
each of n1, n3, and n4 independently represents an integer of 0 to 4;
n2 represents an integer of 0 to 3;
m3 represents an integer of 2 to 6;
$L^a$ represents a single bond or an m3-valent linking group which is bonded to any of the ring carbon atoms shown in formula (3-a) or any of $R^{11a}$ to $R^{14a}$;
when n1 represents 2 to 4, $R^{11a}$ groups may be the same or different, and $R^{11a}$ groups may be bonded to each other to form a ring structure;
when n2 represents 2 or 3, $R^{12a}$ groups may be the same or different, and $R^{12a}$ groups may be bonded to each other to form a ring structure;
when n3 represents 2 to 4, $R^{13a}$ groups may be the same or different, and $R^{13a}$ groups may be bonded to each other to form a ring structure; and
when n4 represents 2 to 4, $R^{14a}$ groups may be the same or different, and $R^{14a}$ groups may be bonded to each other to form a ring structure.

The group represented by $R^1$, $R^2$, $R^{1a}$, and $R^{2a}$ of formulae (1) and (1-a), the group represented by R of formulae (2) and (2-a), and the group represented by $R^{11}$ to $R^{14}$ and $R^{11a}$ to $R^{14a}$ of formulae (3) and (3-a) may include a mono-valent organic residue. Examples thereof are preferably selected from a substituted or unsubstituted alkyl group having 1 to 50, preferably 1 to 18, more preferably 1 to 8 carbon atoms; a substituted or unsubstituted cycloalkyl group having 3 to 50, preferably 3 to 10, more preferably 3 to 8, still more preferably 5 or 6 ring carbon atoms; a substituted or unsubstituted aryl group having 6 to 50, preferably 6 to 25, more preferably 6 to 18 ring carbon atoms; an aralkyl group having 7 to 51 total carbon atoms having a substituted or unsubstituted aryl group having 6 to 50, preferably 6 to 25, more preferably 6 to 18 ring carbon atoms; an amino group; a mono- or di-substituted amino group having a substituent selected from a substituted or unsubstituted alkyl group having 1 to 50, preferably 1 to 18, more preferably to 8 carbon atoms and a substituted or unsubstituted aryl group having 6 to 50, preferably 6 to 25, more preferably 6 to 18 ring carbon atoms; an alkoxy group having a substituted or unsubstituted alkyl group having 1 to 50, preferably 1 to 18, more preferably 1 to 8 carbon atoms; an aryloxy group having a substituted or unsubstituted aryl group having 6 to 50, preferably 6 to 25, more preferably 6 to 18 ring carbon atoms; a mono-, di- or tri-substituted silyl group having a substituent selected from a substituted or unsubstituted alkyl group having 1 to 50, preferably 1 to 18, more preferably 1 to 8 carbon atoms and a substituted or unsubstituted aryl group having 6 to 50, preferably 6 to 25, more preferably 6 to 18 ring carbon atoms; a substituted or unsubstituted heterocyclic group having 5 to 50, preferably 5 to 24, more preferably 5 to 13 ring atoms; a substituted or unsubstituted haloalkyl group having 1 to 50, preferably 1 to 18, more preferably 1 to 8 carbon atoms; a halogen atom selected from a fluorine atom, a chlorine atom, a bromine atom and an iodine atom; a cyano group; a nitro group; a sulfonyl group having a substituent selected from a substituted or unsubstituted alkyl group having 1 to 50, preferably 1 to 18, more preferably 1 to 8 carbon atoms and a substituted or unsubstituted aryl group having 6 to 50, preferably 6 to 25, more preferably 6 to 18 ring carbon atoms; and a di-substituted phosphoryl group having a substituent selected from a substituted or unsubstituted alkyl group having 1 to 50, preferably 1 to 18, more preferably 1 to 8 carbon atoms and a substituted or unsubstituted aryl group having 6 to 50, preferably 6 to 25, more preferably 6 to 18 ring carbon atoms.

Examples of the alkyl group having 1 to 50, preferably 1 to 18, more preferably 1 to 8 carbon atoms include methyl group, ethyl group, n-propyl group, isopropyl group, n-butyl group, isobutyl group, s-butyl group, t-butyl group, pentyl group (inclusive of isomeric groups), hexyl group (inclusive of isomeric groups), heptyl group (inclusive of isomeric groups), octyl group (inclusive of isomeric groups), nonyl group (inclusive of isomeric groups), decyl group (inclusive of isomeric groups), undecyl group (inclusive of isomeric groups), dodecyl group (inclusive of isomeric groups), tridecyl group, tetradecyl group, octadecyl group, tetracosanyl group, and tetracontanyl group. Preferred examples include methyl group, ethyl group, n-propyl group, isopropyl group, n-butyl group, isobutyl group, s-butyl group, t-butyl group, pentyl group (inclusive of isomeric groups), hexyl group (inclusive of isomeric groups), heptyl group (inclusive of isomeric groups), octyl group (inclusive of isomeric groups), nonyl group (inclusive of isomeric groups), decyl group (inclusive of isomeric groups), undecyl group (inclusive of isomeric groups), dodecyl group (inclusive of isomeric groups), tridecyl group, tetradecyl group, and octadecyl group. More preferred examples include methyl group, ethyl group, n-propyl group, isopropyl group, n-butyl group, isobutyl group, s-butyl group, t-butyl group, pentyl group (inclusive of isomeric groups), hexyl group (inclusive of isomeric groups), heptyl group (inclusive of isomeric groups), and octyl group (inclusive of isomeric groups).

Examples of the cycloalkyl group having 3 to 50, preferably 3 to 10, more preferably 3 to 8, still more preferably 5 or 6 ring carbon atoms include cyclopropyl group, cyclobutyl group, cyclopentyl group, cyclohexyl group, cycloheptyl group, cyclooctyl group, and adamantyl group, with cyclopentyl group and cyclohexyl group being preferred.

Examples of the aryl group having 6 to 50, preferably 6 to 25, more preferably 6 to 18 ring carbon atoms include phenyl group, naphthyl group, naphthylphenyl group, biphenylyl group, terphenylyl group, acenaphthylenyl group, anthryl group, benzanthryl group, aceanthryl group, phenanthryl group, benzophenanthryl group, phenalenyl group, fluorenyl group, 9,9'-spirobifluorenyl group, benzofluorenyl group, dibenzofluorenyl group, picenyl group, pentaphenyl group, pentacenyl group, pyrenyl group, chrysenyl group, benzochrysenyl group, s-indacenyl group, as-indacenyl group, fluoranthenyl group, benzofluoranthenyl group, tetracenyl group, picenyl group, triphenylenyl group, benzotriphenylenyl group, perylenyl group, coronyl group, and dibenzanthryl group. Preferred examples include phenyl group, naphthyl group, biphenylyl group, terphenylyl group, acenaphthylenyl group, anthryl group, phenanthryl group, fluorenyl group, 9,9'-spirobifluorenyl group, fluoranthenyl group, and triphenylenyl group.

Examples of the arylene group having 6 to 50, preferably 6 to 25, more preferably 6 to 18 ring carbon atoms include the groups obtained by removing one hydrogen atom from the aryl groups mentioned above.

The heteroaryl group having 5 to 50, preferably 5 to 24, more preferably 5 to 13 ring atoms include at least one, preferably 1 to 5, more preferably 1 to 3, and still more preferably 1 or 2 hetero atoms, for example, a nitrogen atom, a sulfur atom, an oxygen atom, a phosphorus atom. Examples thereof include pyrrolyl group, furyl group, thienyl group, pyridyl group, pyridazinyl group, pyrimidinyl group, pyrazinyl group, triazinyl group, imidazolyl group, oxazolyl group, thiazolyl group, pyrazolyl group, isooxazolyl group, isothiazolyl group, oxadiazolyl group, thiadiazolyl group, triazolyl group, tetrazolyl group, indolyl group, isoindolyl group, benzofuranyl group, isobenzofuranyl group, benzothiophenyl group, isobenzothiophenyl group, indolizinyl group, quinolizinyl group, quinolyl group, isoquinolyl group, cinnolyl group, phthalazinyl group, quinazolinyl group, quinoxalinyl group, benzimidazolyl group, benzoxazolyl group, benzothiazolyl group, indazolyl group, benzisoxazolyl group, benzisothiazolyl group, dibenzofuranyl group, dibenzothiophenyl group, carbazolyl group, phenanthridinyl group, acridinyl group, phenanthrolinyl group, phenazinyl group, phenothiazinyl group, phenoxazinyl group, azatriphenylenyl group, diazatriphenylenyl group, xanthenyl group, azacarbazolyl group, azadibenzofuranyl group, azadibenzothiophenyl group, benzofuranobenzothiophenyl group, benzothienobenzothiophenyl group, dibenzofuranonaphthyl group, dibenzothienonaphthyl group, and dinaphthothienothiophenyl group. Preferred examples include pyridyl group, pyrimidinyl group, triazinyl group, imidazolyl group, triazolyl group, indolyl group, isoindolyl group, benzofuranyl group, isobenzofuranyl group, benzothiophenyl group, isobenzothiophenyl group, indolizinyl group, quinolizinyl group, quinolyl group, isoquinolyl group, quinazolinyl group, quinoxalinyl group, benzimidazolyl group, benzoxazolyl group, benzothiazolyl group, benzisoxazolyl group, benzisothiazolyl group, dibenzofuranyl group, dibenzothiophenyl group, carbazolyl group, phenanthridinyl group, phenanthrolinyl group, and phenazinyl group. More preferred examples include pyridyl group, pyrimidinyl group, triazinyl group, quinolyl group, isoquinolyl group, quinazolinyl group, quinoxalinyl group, benzimidazolyl group, benzoxazolyl group, benzothiazolyl group, dibenzofuranyl group, dibenzothiophenyl group, carbazolyl group, phenanthridinyl group, and phenanthrolinyl group.

In addition, examples of the heteroaryl group having 5 to 50 ring atoms preferably include mono-valent groups derived from the following compounds by removing one hydrogen atom:

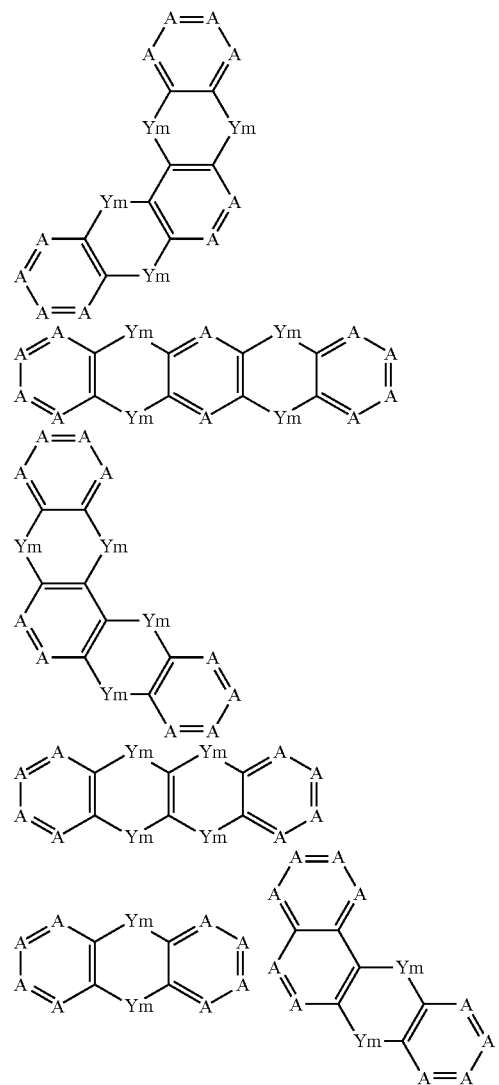

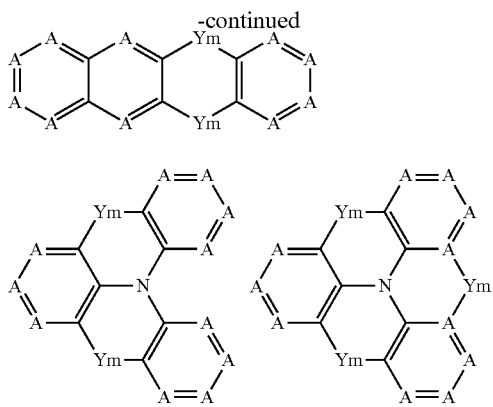

wherein:

A independently represents $CR^{100}$ or a nitrogen atom;

$R^{100}$ independently represents a hydrogen atom or a group;

Y independently represents a single bond, $C(R^{101})(R^{102})$, an oxygen atom, v a sulfur atom, or $N(R^{103})$;

each of $R^{101}$, $R^{102}$ and $R^{103}$ independently represents a hydrogen atom or a group; and m independently represents 0 or 1.

The group referred to in the above formulae is selected from those mentioned above.

Examples of the heteroarylene group having 5 to 50, preferably 6 to 24, more preferably 6 to 13 ring atoms include those obtained by removing one hydrogen atom from the heteroaryl groups mentioned above.

Examples of the aralkyl group having 7 to 51 total carbon atoms which has an aryl group having 6 to 50, preferably 6 to 25, more preferably 6 to 18 ring carbon atoms include those having the aryl group mentioned above.

Examples of the mono- or di-substituted amino group having a substituent selected from an alkyl group having 1 to 50, preferably 1 to 18, more preferably 1 to 8 carbon atoms and an aryl group having 6 to 50, preferably 6 to 25, more preferably 6 to 18 ring carbon atoms include those having a substitutent selected from the alkyl groups and the aryl groups which are mentioned above.

Examples of the alkoxy group having an alkyl group having 1 to 50, preferably 1 to 18, more preferably 1 to 8 carbon atoms include those having the alkyl group mentioned above.

Examples of the aryloxy group having an aryl group having 6 to 50, preferably 6 to 25, more preferably 6 to 18 ring carbon atoms include those having the aryl group mentioned above.

Examples of the mono-, di- or tri-substituted silyl group having a substituent selected from an alkyl group having 1 to 50, preferably 1 to 18, more preferably 1 to 8 carbon atoms and an aryl group having 6 to 50, preferably 6 to 25, more preferably 6 to 18 ring carbon atoms include those having a substituent selected form the alkyl groups and the aryl groups which are mentioned above.

Examples of the haloalkyl group having 1 to 50, preferably 1 to 18, more preferably 1 to 8 carbon atoms included those obtained by replacing one or more hydrogen atoms of the alkyl groups mentioned above with a halogen atom, such as a fluorine atom, a chlorine atom, a bromine atom and an iodine atom.

Examples of the sulfonyl group having a group selected from an alkyl group having 1 to 50, preferably 1 to 18, more preferably 1 to 8 carbon atoms and an aryl group having 6 to 50, preferably 6 to 25, more preferably 6 to 18 ring carbon atoms include those having a substituent selected from the alkyl groups and the aryl groups which are mentioned above.

Examples of the di-substituted phosphoryl group having a substituent selected from an alkyl group having 1 to 50, preferably 1 to 18, more preferably 1 to 8 carbon atoms and an aryl group having 6 to 50, preferably 6 to 25, more preferably 6 to 18 ring carbon atoms include those having a substitutent selected from the alkyl groups and the aryl groups which are mentioned above.

Examples of the linker represented by $L^a$ of formulae (1-a) to (3-a) include a single bond and an m1-, m2- or m3-valent group obtained by removing m1-, m2- or m3 hydrogen atoms from the group mentioned above, preferably a single bond, an aromatic hydrocarbon ring group obtained by removing m1-, m2- or m3 hydrogen atoms from the aryl groups mentioned above, or an aromatic heterocyclic ring group obtained by removing m1-, m2- or m3 hydrogen atoms from the heteroaryl group mentioned above.

Examples of the group represented by $R^1$, $R^2$, $R^{1a}$, and $R^{2a}$ of formulae (1) and (1-a), examples of the group represented by R of formulae (2) and (2-a), and examples of the group represented by $R^{11}$ to $R^{14}$ and $R^{11a}$ to $R^{14a}$ of formulae (3) and (3-a) are preferably selected from the examples of the group comprising a ring structure which are mentioned below with respect to the nitrogen-containing heterocyclic compound B, more preferably selected from the groups represented by formula (10A) mentioned below, and still more preferably selected from the groups represented by any of formulae (10A-1) to (10A-3) mentioned below. In a preferred nitrogen-containing heterocyclic compound A represented by formula (2), $X^2$ or $X^{13}$ represents CR wherein R is selected from the above groups.

The material for organic EL device of the invention comprises the nitrogen-containing heterocyclic compound A mentioned above. The content of the nitrogen-containing heterocyclic compound A in the material for organic EL device is not particularly limited and 1% by mass or more is sufficient, preferably 10% by mass or more, more preferably 50% by mass or more, still more preferably 80% by mass or more, and particularly preferably 90% by mass or more.

The material for organic EL device of the invention is useful as the material for producing an organic EL device, for example, as a host material or a dopant material for use in a light emitting layer of a fluorescent emission unit, and as a host material for use in a light emitting layer of a phosphorescent emission unit. In addition, useful as a material for forming a fluorescent emission unit and a phosphorescent emission unit, i.e., a material for use in an anode-side organic thin film layer between an anode and a light emitting layer and in a cathode-side organic thin film layer between a cathode and a light emitting layer, for example, a hole transporting layer, a hole injecting layer, an electron transporting layer, an electron injecting layer, a hole blocking layer, and an electron blocking layer.

The "emission unit" referred to herein is the smallest unit for emitting light by the recombination of injected holes and injected electrons, which comprises one or more organic layers wherein at least one layer is a light emitting layer.

Nitrogen-Containing Heterocyclic Compound B

The nitrogen-containing heterocyclic compound B is represented by formula (1'):

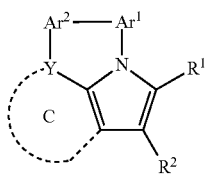

(1')

wherein:

each of $R^1$ and $R^2$ independently represents a hydrogen atom or a group;

when both $R^1$ and $R^2$ represent the groups, $R^1$ and $R^2$ may be bonded to each other to form a ring structure;

each of $Ar^1$ and $Ar^2$ independently represents a substituted or unsubstituted arylene group having 6 to 50 ring carbon atoms or a substituted or unsubstituted heteroarylene group having 5 to 50 ring atoms;

one of ring atoms of $Ar^1$ is bonded to $Ar^2$, and another ring atom of $Ar^1$ which is adjacent to the ring atom bonded to $Ar^2$ is bonded to a nitrogen atom shown in formula (1');

one of ring atoms of $Ar^2$ is bonded to $Ar^1$, and another ring atom of $Ar^2$ which is adjacent to the ring atom bonded to $Ar^1$ is bonded to Y shown in formula (1');

Y represents a carbon atom or a nitrogen atom; and

C represents a substituted or unsubstituted aromatic hydrocarbon ring or a substituted or unsubstituted aromatic heterocyclic ring;

provided that at least one of $R^1$, $R^2$, a substituent on $Ar^1$, a substituent on $Ar^2$, and a substituent on the aromatic hydrocarbon ring or the aromatic heterocyclic ring each represented by C is a group comprising a ring structure or a group comprising a reactive site.

The details of $R^1$, $R^2$, $Ar^1$, $Ar^2$, Y, and C of formula (1') are as described above with respect to the nitrogen-containing heterocyclic compound A represented by formula (1).

The nitrogen-containing heterocyclic compound B having a group comprising a ring structure is useful as a material for producing the organic EL device mentioned below. The group comprising the ring structure has an effect of improving the film properties of an organic thin layer comprising the nitrogen-containing heterocyclic compound B.

Examples of the group comprising a ring structure include those comprising a group selected from a substituted or unsubstituted cycloalkyl group having 5 to 50, preferably 3 to 6, more preferably 5 or 6 ring carbon atoms; a substituted or unsubstituted aryl group having 6 to 50, preferably 6 to 24, more preferably 6 to 18 ring carbon atoms; an aralkyl group having 7 to 51 total carbon atoms which has a substituted or unsubstituted aryl group having 6 to 50, preferably 6 to 24, more preferably 6 to 18 ring carbon atoms; an amino group substituted with a substituted or unsubstituted aryl group having 6 to 50, preferably 6 to 24, more preferably 6 to 18 ring carbon atoms; an aryloxy group having a substituted or unsubstituted aryl group having 6 to 50, preferably 6 to 24, more preferably 6 to 18 ring carbon atoms; a silyl group substituted with a substituted or unsubstituted aryl group having 6 to 50, preferably 6 to 24, more preferably 6 to 18 ring carbon atoms; a substituted or unsubstituted heteroaryl group having 5 to 50, preferably 5 to 24, more preferably 5 to 13 ring atoms; a sulfonyl group substituted with a substituted or unsubstituted aryl group having 6 to 50, preferably 6 to 24, more preferably 6 to 18 ring carbon atoms; and a phosphoryl group substituted with a substituted or unsubstituted aryl group having 6 to 50, preferably 6 to 24, more preferably 6 to 18 ring carbon atoms. Preferred examples include a group comprising a substituted or unsubstituted aryl group having 6 to 50 ring carbon atoms; a group comprising a substituted or unsubstituted heteroaryl group having 5 to 50 ring atoms, and a mono- or di-substituted amino group having a substituted or unsubstituted aryl group having 6 to 50 ring carbon atoms. The details of these groups are as described above with respect to the nitrogen-containing heterocyclic compound A represented by formula (1).

The above group comprising a ring structure may be substituted with a group comprising a ring structure which is selected from those mentioned above.

The nitrogen-containing heterocyclic compound having the group comprising a reactive site is useful as the intermediate for synthesizing various derivatives having a structure characteristic of the nitrogen-containing heterocyclic compound B.

These derivatives are expected to be useful as a material for organic EL device, an optical material such as resist, a detecting material such as fluorescent marker, and a pharmaceutical or agrochemical material such as anticancer agent.

The derivative can be produced by coupling reactions, addition reactions, oxidation reactions, and reduction reactions, for example, Ullmann reaction using a copper catalyst, Mizoroki-Heck reaction using a palladium nickel catalyst, Negishi reaction, Stille reaction, Sonogashira reaction, Suzuki-Miyaura reaction, Buchwald-Hartwig reaction, and Kumada-Tamao-Corriu reaction.

Examples of the group comprising a reactive site include a group capable of participating in oxidative addition in a coupling reaction, for example, a group comprising a reactive site, such as a halogen atom, an alkylsulfonyloxy group, an arylsulfonyloxy group, an alkylcarbonyloxy group, and an arylcarbonyloxy group; a group capable of participating in transmetalation in a coupling reaction, for example, a group comprising a reactive site, such as a boron-containing group, a zinc-containing group, a tin-containing group, a silicon-containing group, a magnesium-containing group, and a lithium-containing group; a heteroatom-containing functional group, for example, a group comprising a reactive site, such as an amino group, a nitro group, a cyano group, a hydroxyl group, an alkylcarbonyl group, a arylcarbonyl group, and a carboxyl group; and a polymerizable functional group, for example, a group comprising a reactive site, such as a vinyl group, a (meth)acryloyl group, an epoxy group, and an oxetanyl group.

The group comprising a reactive site may include those having a group comprising a reactive site on a substituent, for example, the substituent described above.

The nitrogen-containing heterocyclic compound B represented by formula (1') may be a polymer represented by formula (1'-a):

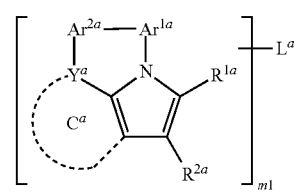

(1'-a)

wherein:

each of $R^{1a}$ and $R^{2a}$ independently represents a hydrogen atom or a group;

when both $R^{1a}$ and $R^{2a}$ represent the groups, $R^{1a}$ and $R^{2a}$ may be bonded to each other to form a ring structure;

each of $Ar^{1a}$ and $Ar^{2a}$ independently represents a substituted or unsubstituted arylene group having 6 to 50 ring carbon atoms or a substituted or unsubstituted heteroarylene group having 5 to 50 ring atoms;

one of ring atoms of $Ar^{1a}$ is bonded to $Ar^{2a}$, and another ring atom of $Ar^{1a}$ which is adjacent to the ring atom bonded to $Ar^{2a}$ is bonded to a nitrogen atom shown in formula (1'-a);

one of ring atoms of $Ar^{2a}$ is bonded to $Ar^{1a}$, and another ring atom of $Ar^{2a}$ which is adjacent to the ring atom bonded to $Ar^{1a}$ is bonded to $Y^a$ shown in formula (1'-a);

$Y^a$ represents a carbon atom or a nitrogen atom;

$C^a$ represents a substituted or unsubstituted aromatic hydrocarbon ring or a substituted or unsubstituted aromatic heterocyclic ring;

m1 represents an integer of 2 to 6; and $L^a$ represents a single bond or an m1-valent linking group which is bonded to any of $R^{1a}$, $R^{2a}$, $Ar^{1a}$, $Ar^{2a}$, and ring $C^a$;

provided that at least one of $R^{1a}$, $R^{2a}$, a substituent on $Ar^{1a}$, a substituent on $Ar^{2a}$, and a substituent on the aromatic hydrocarbon ring or the aromatic heterocyclic ring each represented by $C^a$ is a group comprising a ring structure or a group comprising a reactive site.

The details of $R^{1a}$, $R^{2a}$, $Ar^{1a}$, $Ar^{2a}$, $Y^a$, and $C^a$ of formula (1'-a) are as described above with respect to nitrogen-containing heterocyclic compound A represented by formula (1-a).

The nitrogen-containing heterocyclic compound B is preferably represented by formula (2'):

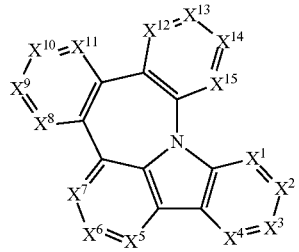

(2')

wherein:

each of $X^1$ to $X^{15}$ independently represents C(R) or a nitrogen atom;

R represents a hydrogen atom or a group; and when two or more of $X^1$ to $X^{15}$ have the groups, the groups may be bonded to each other to form a ring structure;

provided that at least one of $X^1$ to $X^{15}$ represents C(R) wherein R represents a group comprising a ring structure or a group comprising a reactive site.

The details of $X^1$ to $X^{15}$ and R of formula (2') are as described above with respect to the nitrogen-containing heterocyclic compound A represented by formula (2).

The nitrogen-containing heterocyclic compound B represented by formula (2') may be a polymer represented by formula (2'-a).

$X^{13}$ or $X^2$ of formula (2') preferably represents C(R) wherein R represents a group comprising a ring structure or a group comprising a reactive site.

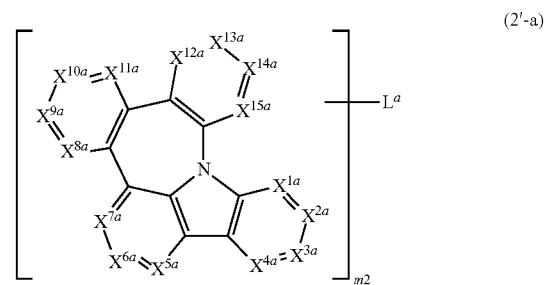

(2'-a)

In formula (2'-a), each of $X^{1a}$ to $X^{15a}$ independently represents C(R) or a nitrogen atom;

R represents a hydrogen atom or a group;

when two or more of $X^{1a}$ to $X^{15a}$ have the groups, the groups may be bonded to each other to form a ring structure;

m2 represents an integer of 2 to 6; and $L^a$ represents a single bond or an m2-valent linking group which is bonded to any of $X^{1a}$ to $X^{15a}$.

The details of $X^{1a}$ to $X^{15a}$ and R of formula (2'-a) are as described above with respect to the nitrogen-containing heterocyclic compound A represented by formula (2-a).

$X^{13a}$ or $X^{2a}$ of formula (2'-a) preferably represents C(R) wherein R represents a group comprising a ring structure or a group comprising a reactive site.

The nitrogen-containing heterocyclic compound B is preferably represented by formula (3'):

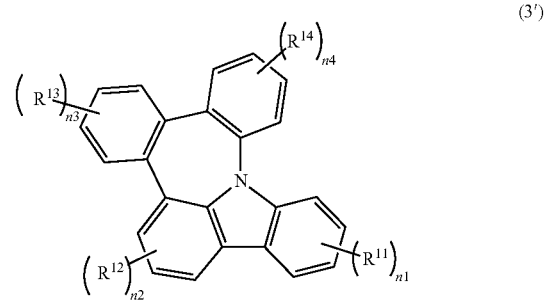

(3')

wherein:

each of $R^{11}$ to $R^{14}$ independently represents a group;

each of n1, n3 and n4 independently represents an integer of 0 to 4;

n2 represents an integer of 0 to 3;

when n1 represents 2 to 4, $R^{11}$ groups may be the same or different, and $R^{11}$ groups may be bonded to each other to form a ring structure;

when n2 represents 2 or 3, $R^{12}$ groups may be the same or different, and $R^{12}$ groups may be bonded to each other to form a ring structure;

when n3 represents 2 to 4, $R^{13}$ groups may be the same or different, and $R^{13}$ groups may be bonded to each other to form a ring structure; and when n4 represents 2 to 4, $R^{14}$ groups may be the same or different, and $R^{14}$ groups may be bonded to each other to form a ring structure;

provided that formula (3') satisfies at least one of requirements (i) to (iv):

(i) n1 represents an integer of 1 to 4, and at least one of $R^{11}$ represents a group comprising a ring structure or a group comprising a reactive site;

(ii) n2 represents an integer of 1 to 3, and at least one of $R^{12}$ represents a group comprising a ring structure or a group comprising a reactive site;

(iii) n3 represents an integer of 1 to 4, and at least one of $R^{13}$ represents a group comprising a ring structure or a group comprising a reactive site; and (iv) n4 represents an integer of 1 to 4, and at least one of $R^{14}$ represents a group comprising a ring structure or a group comprising a reactive site.

The details of $R^{11}$ to $R^{14}$ and n1 to n4 of formula (3') are as described above with respect to the nitrogen-containing heterocyclic compound A represented by formula (3).

The nitrogen-containing heterocyclic compound B represented by formula (3') preferably satisfies the requirement (i) or (iv).

The nitrogen-containing heterocyclic compound B represented by formula (3') may be a polymer represented by formula (3'-a):

$$\left[ \begin{array}{c} (R^{14a})_{n4} \\ (R^{13a})_{n3} \\ (R^{12a})_{n2} \end{array} \begin{array}{c} \\ N \\ (R^{11a})_{n1} \end{array} L^a \right]_{m3} \quad (3'\text{-a})$$

wherein:
each of $R^{11a}$ to $R^{14a}$ independently represents a group;
each of n1, n3 and n4 independently represents an integer of 0 to 4;
n2 represents an integer of 0 to 3;
m3 represents an integer of 2 to 6;
$L^a$ represents a single bond or an m3-valent linking group which is bonded to any of ring carbon atoms and $R^{11a}$ to $R^{14a}$ shown in formula (3'-a);
when n1 represents 2 to 4, $R^{11a}$ groups may be the same or different, and $R^{11a}$ groups may be bonded to each other to form a ring structure;
when n2 represents 2 or 3, $R^{12a}$ groups may be the same or different, and $R^{12a}$ groups may be bonded to each other to form a ring structure;
when n3 represents 2 to 4, $R^{13a}$ groups may be the same or different, and $R^{13a}$ groups may be bonded to each other to form a ring structure; and
when n4 represents 2 to 4, $R^{14a}$ groups may be the same or different, and $R^{14a}$ groups may be bonded to each other to form a ring structure;
provided that formula (3'-a) satisfies at least one of requirements (i) to (iv):

(i) n1 represents an integer of 1 to 4, and at least one of $R^{11a}$ represents a group comprising a ring structure or a group comprising a reactive site;

(ii) n2 represents an integer of 1 to 3, and at least one of $R^{12a}$ represents a group comprising a ring structure or a group comprising a reactive site;

(iii) n3 represents an integer of 1 to 4, and at least one of $R^{13a}$ represents a group comprising a ring structure or a group comprising a reactive site; and (iv) n4 represents an integer of 1 to 4, and at least one of $R^{14a}$ represents a group comprising a ring structure or a group comprising a reactive site;

The details of $R^{11a}$ to $R^{14a}$ and n1 to n4 of formula (3'-a) are as described above with respect to the nitrogen-containing heterocyclic compound A represented by formula (3-a).

The nitrogen-containing heterocyclic compound B represented by formula (3'-a) preferably satisfies the requirement (i) or (iv).

The group comprising a ring structure of formulae (1') to (3') and (1'-a) to (3'-a) is preferably represented by formula (10A):

$$-(L^A)_{nA}-R^A \quad (10A)$$

wherein:
$R^A$ represents a ring group;
$L^A$ represents a single bond or a divalent linking group;
nA represents an integer of 1 to 4; and
when nA represents 2 to 4, $L^A$ groups may be the same or different.

Examples of the divalent linking group of formula (10A) preferably include divalent residues of the group selected from a substituted or unsubstituted alkyl group having 1 to 50 carbon atoms, a substituted or unsubstituted cycloalkyl group having 3 to 50 ring carbon atoms, a substituted or unsubstituted aryl group having 6 to 50 ring carbon atoms, a mono- or di-substituted amino group having a group selected from a substituted or unsubstituted alkyl group having 1 to 50 carbon atoms and a substituted or unsubstituted aryl group having 6 to 50 ring carbon atoms, and a substituted or unsubstituted heteroaryl group having 5 to 50 ring atoms.

Examples of the ring group of formula (10A) preferably include a substituted or unsubstituted cycloalkyl group having 3 to 50, preferably 3 to 10, more preferably 3 to 8, still more preferably 5 or 6 ring carbon atoms; a substituted or unsubstituted aryl group having 6 to 50, preferably 6 to 25, more preferably 6 to 18 ring carbon atoms; a substituted or unsubstituted heteroaryl group having 5 to 50, preferably 5 to 24, more preferably 5 to 13 ring atoms; and a mono- or di-substituted amino group having a substituted or unsubstituted aryl group having 6 to 50 ring carbon atoms.

The group comprising a ring structure is preferably a substituted or unsubstituted aryl group having 6 to 50 ring carbon atoms, a substituted or unsubstituted heteroaryl group having 5 to 50 ring atoms, or a mono- or di-substituted amino group having a substituted or unsubstituted aryl group having 6 to 50 ring carbon atoms.

The details of these groups are as described above with respect to the nitrogen-containing heterocyclic compound A represented by formula (1).

The group comprising a ring structure of formulae (1') to (3') and (1'-a) to (3'-a) is preferably represented by any of formulae (10A-1) to (10A-3);

$$-L^{A1}\text{-}{^N}\text{Ar} \quad (10A\text{-}1)$$

$$-L^{A2}\text{-}{^F}\text{Ar} \quad (10A\text{-}2)$$

$$-L^{A3}\text{-NAr}^{41}\text{Ar}^{42} \quad (10A\text{-}3)$$

in formula (10A-1),
$L^{A1}$ represents a single bond or a divalent linking group; and
$^N$Ar represents a substituted or unsubstituted nitrogen-containing heterocyclic group; in formula (10A-2),
$L^{A2}$ represents a single bond or a divalent linking group; and $^F$Ar represents a substituted or unsubstituted fused aryl group having 10 to 50 ring carbon atoms or a substituted or unsubstituted fused heteroaryl group having 8 to 50 ring atoms;

in formula (10A-3), $L^{43}$ represents a single bond or a divalent linking group; and each of $Ar^{41}$ and $Ar^{42}$ independently represents a substituted or unsubstituted aryl group having 6 to 50 ring carbon atoms or a substituted or unsubstituted heteroaryl group having 5 to 50 ring atoms.

Examples of the divalent linking group for $L^{41}$ to $L^{43}$ are as described above with respect to $L^A$ of formula (10A).

Examples of $L^{41}$ to $L^{43}$ preferably include a single bond and a divalent residue of a substituted or unsubstituted aryl group having 6 to 50 ring carbon atoms or a substituted or unsubstituted heteroaryl group having 5 to 50 ring atoms. The details of these groups are as described above with respect to the nitrogen-containing heterocyclic compound A represented by formula (1).

Examples of the nitrogen-containing heterocyclic group for $^N$Ar of formula (10A-1) include those having a nitrogen atom which are selected from the heteroaryl groups having 5 to 50 ring atoms described above with respect to the nitrogen-containing heterocyclic compound A represented by formula (1). $^N$Ar is preferably pyrrolyl group, pyridyl group, pyridazinyl group, pyrimidinyl group, pyrazinyl group, triazinyl group, imidazolyl group, oxazolyl group, thiazolyl group, pyrazolyl group, isoxazolyl group, isothiazolyl group, oxadiazolyl group, thiadiazolyl group, triazolyl group, tetrazolyl group, indolyl group, isoindolyl group, indolizinyl group, quinolizinyl group, quinolyl group, isoquinolyl group, quinazolinyl group, quinoxalinyl group, benzimidazolyl group, benzoxazolyl group, indazolyl group, carbazolyl group, phenanthrolinyl group, phenazinyl group, phenothiazinyl group, phenoxazinyl group, or azacarbazolyl group. More preferred are pyridyl group, pyrimidinyl group, triazinyl group, indolyl group, isoindolyl group, quinolizinyl group, quinolyl group, isoquinolyl group, quinazolinyl group, quinoxalinyl group, benzimidazolyl group, carbazolyl group, phenanthrolinyl group, phenazinyl group, and azacarbazolyl group.

Examples of the fused aryl group having 10 to 50 ring carbon atoms for $^F$Ar of formula (10A-2) include those wherein two or more rings are fused, which are selected from the aryl groups having 6 to 50 ring carbon atoms described above with respect to the nitrogen-containing heterocyclic compound A represented by formula (1). Preferred are naphthyl group, acenaphthylenyl group, anthryl group, benzanthryl group, aceanthryl group, phenanthryl group, benzophenanthryl group, phenalenyl group, fluorenyl group, 9,9'-spirobifluorenyl group, benzofluorenyl group, dibenzofluorenyl group, picenyl group, pentaphenyl group, pentacenyl group, pyrenyl group, chrysenyl group, benzochrysenyl group, s-indacenyl group, as-indacenyl group, fluoranthenyl group, benzofluoranthenyl group, tetracenyl group, picenyl group, triphenylenyl group, benzotriphenylenyl group, perylenyl group, and dibenzanthryl group. More preferred are anthryl group, naphthyl group, phenanthryl group, fluorenyl group, 9,9'-spirobifluorenyl group, benzofluorenyl group, dibenzofluorenyl group, picenyl group, pyrenyl group, chrysenyl group, fluoranthenyl group, benzofluoranthenyl group, and triphenylenyl group.

Examples of the fused heteroaryl group having 8 to 50 ring atoms for $^F$Ar of formula (10A-2) include those wherein two or more rings are fused, which are selected from the heteroaryl groups having 5 to 50 ring atoms described above with respect to the nitrogen-containing heterocyclic compound A represented by formula (1). Preferred are benzofuranyl group, isobenzofuranyl group, benzothiophenyl group, isobenzothiophenyl group, indolizinyl group, quinolizinyl group, quinolyl group, isoquinolyl group, cinnolyl group, phthalazinyl group, quinazolinyl group, quinoxalinyl group, benzimidazolyl group, benzoxazolyl group, benzothiazolyl group, indazolyl group, benzisoxazolyl group, benzisothiazolyl group, dibenzofuranyl group, dibenzothiophenyl group, carbazolyl group, phenanthridinyl group, acridinyl group, phenanthrolinyl group, phenazinyl group, phenothiazinyl group, phenoxazinyl group, azatriphenylenyl group, diazatriphenylenyl group, xanthenyl group, azacarbazolyl group, azadibenzofuranyl group, azadibenzothiophenyl group, benzofuranobenzothiophenyl group, benzothienobenzothiophenyl group, dibenzofuranonaphthyl group, dibenzothienonaphthyl group, and dinaphthothienothiophenyl group. More preferred are indolizinyl group, quinolizinyl group, quinolyl group, isoquinolyl group, quinazolinyl group, quinoxalinyl group, benzimidazolyl group, dibenzofuranyl group, dibenzothiophenyl group, carbazolyl group, phenanthridinyl group, phenanthrolinyl group, azacarbazolyl group, azadibenzofuranyl group, and azadibenzothiophenyl group.

Examples of the aryl group having 6 to 50 ring carbon atoms for $Ar^{41}$ and $Ar^{42}$ of formula (10A-3) are as described above with respect to the aryl group having 6 to 50 ring carbon atoms of the nitrogen-containing heterocyclic compound A represented by formula (1).

Examples of the heteroaryl group having 5 to 50 ring atoms for $Ar^{41}$ and $Ar^{42}$ of formula (10A-3) are as described above with respect to the heteroaryl group having 5 to 50 ring atoms of the nitrogen-containing heterocyclic compound A represented by formula (1).

Examples of the group for $L^{41}$, $^N$Ar, $L^{42}$, $^F$Ar, $L^{43}$, $Ar^{41}$, and $Ar^{42}$ of formulae (10A-1) to (10A-3) are as described above with respect to the nitrogen-containing heterocyclic compound A represented by formula (1).

The group comprising a reactive site of formulae (1') to (3') and (1'-a) to (3'-a) is preferably represented by formula (10B):

$$-(L^B)_{nB}-R^B \qquad (10B)$$

wherein:

$R^B$ represents a reactive site;

$L^B$ represents a single bond or a divalent linking group;

nB represents an integer of 1 to 4; and when nB represents 2 to 4, $L^B$ groups may be the same or different.

The reactive site of formula (10B) is preferably selected from the group capable of participating in oxidative addition in a coupling reaction, the group capable of participating in transmetalation in a coupling reaction, the heteroatom-containing functional group, and the polymerizable functional group, which are described above. Preferred are a halogen atom, an alkylsulfonyloxy group, an arylsulfonyloxy group, an alkylcarbonyloxy group, an arylcarbonyloxy group, a boron-containing group, a zinc-containing group, a tin-containing group, a silicon-containing group, a magnesium-containing group, a lithium-containing group, an amino group, a nitro group, a cyano group, a hydroxyl group, an alkylcarbonyl group, an arylcarbonyl group, a carboxyl group, a vinyl group, a (meth)acryloyl group, an epoxy group, and an oxetanyl group.

The divalent linking group of formula (10B) is preferably a divalent residue of a group selected from a substituted or unsubstituted alkyl group having 1 to 50 carbon atom, a substituted or unsubstituted cycloalkyl group having 3 to 50 ring carbon atoms, a substituted or unsubstituted aryl group having 6 to 50 ring carbon atoms, a mono- or di-substituted amino group having a group selected from a substituted or unsubstituted alkyl group having 1 to 50 carbon atoms and a substituted or unsubstituted aryl group having 6 to 50 ring carbon atoms, and a substituted or unsubstituted heteroaryl group having 5 to 50 ring atoms. The details of these groups are as described above with respect to the nitrogen-containing heterocyclic compound A represented by formula (1).

Examples of the nitrogen-containing heterocyclic compound A represented by formulae (1) to (3) and the nitrogen-containing heterocyclic compound B represented by formulae (1') to (3') are shown below, although not limited thereto. In the following compounds, Me is a methyl group and Bu is a butyl group.

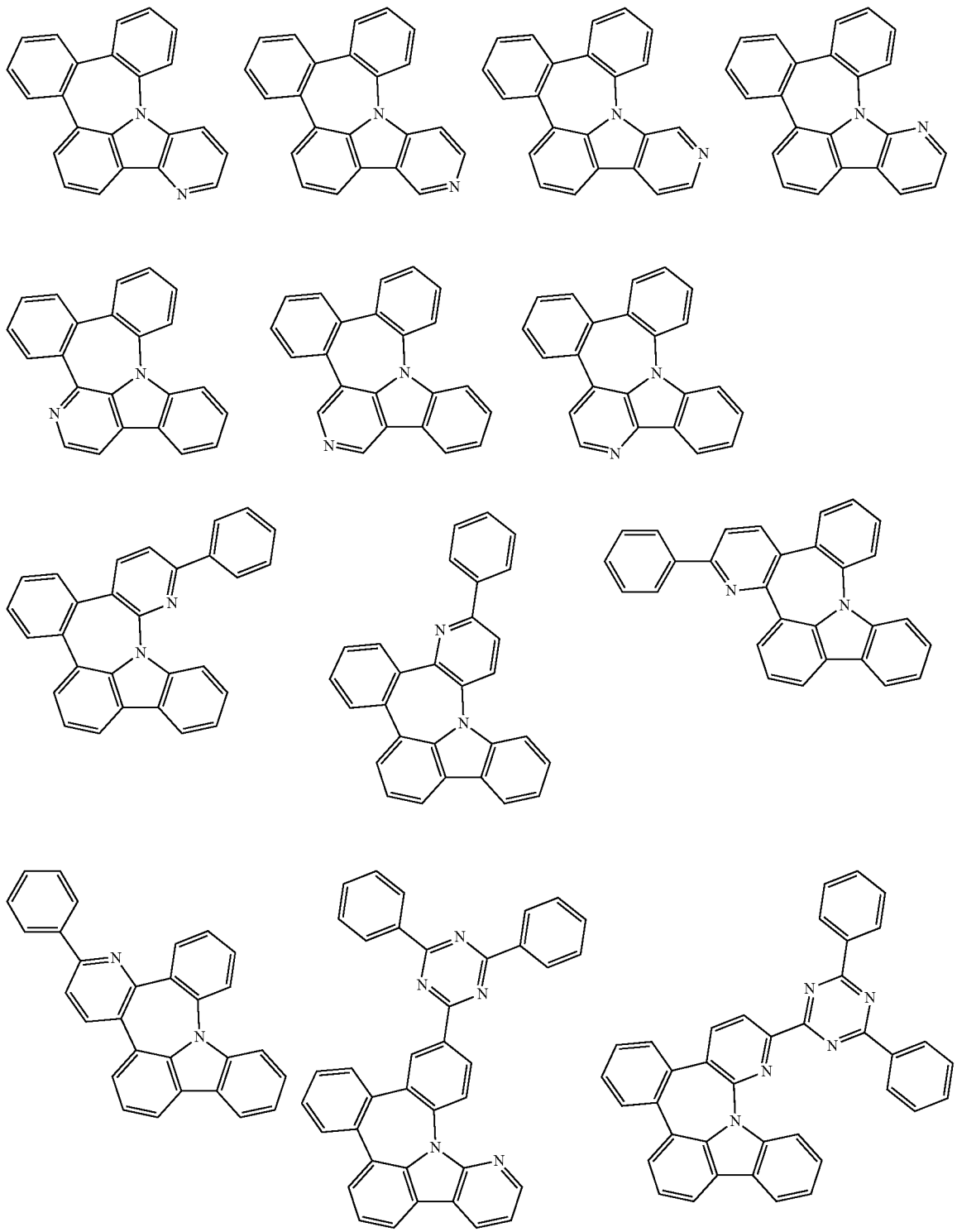

-continued
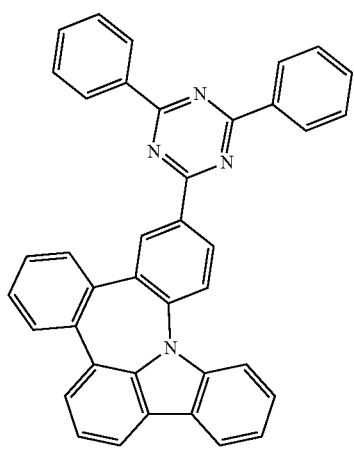
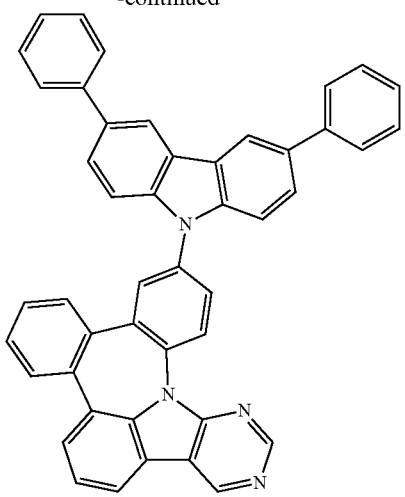
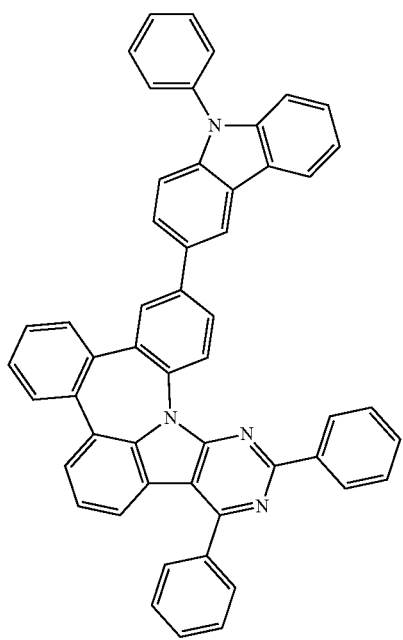
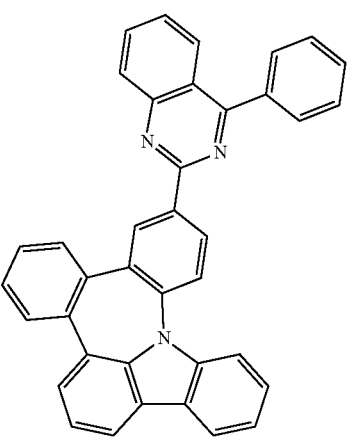
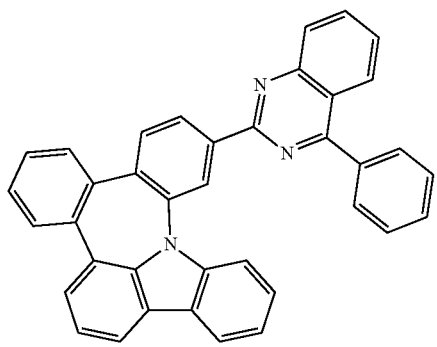
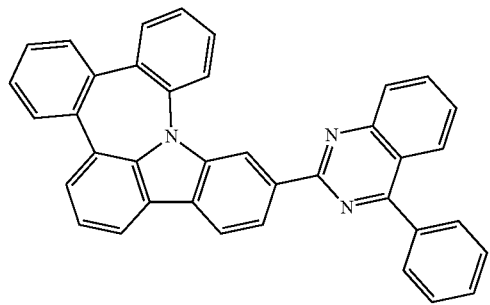

-continued
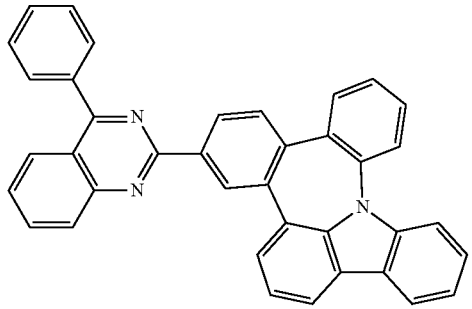
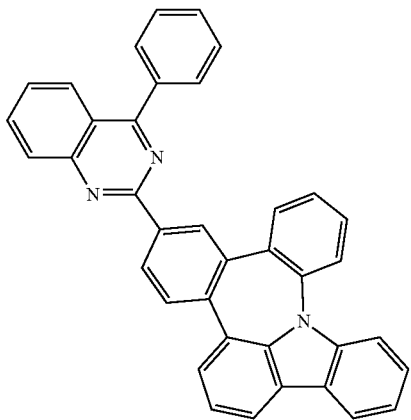
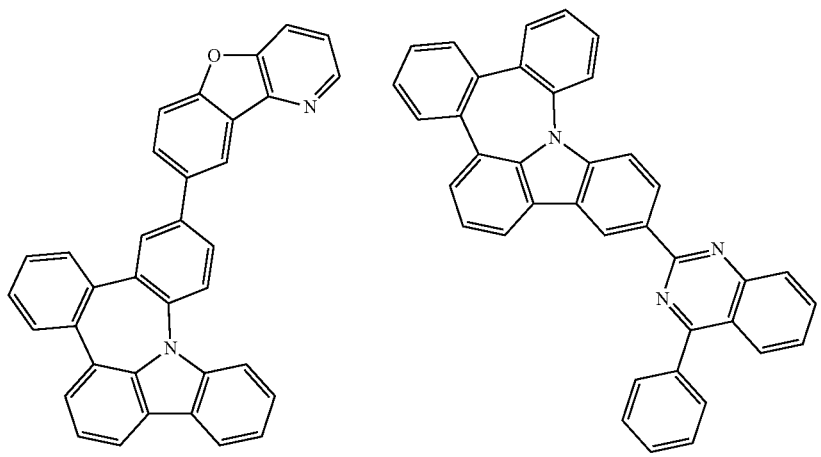
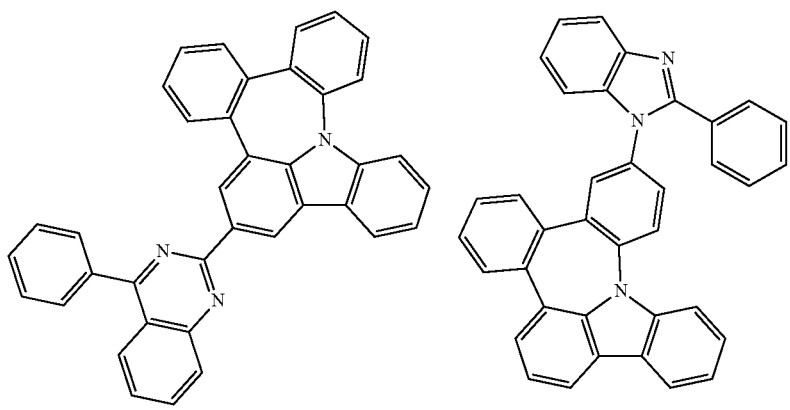

-continued
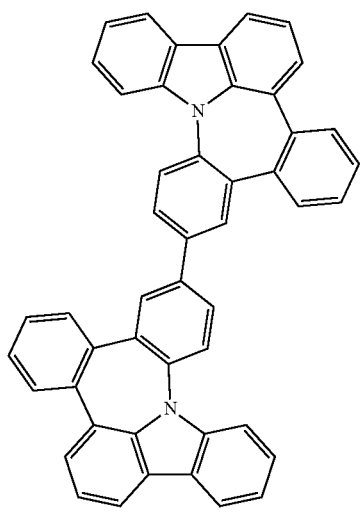
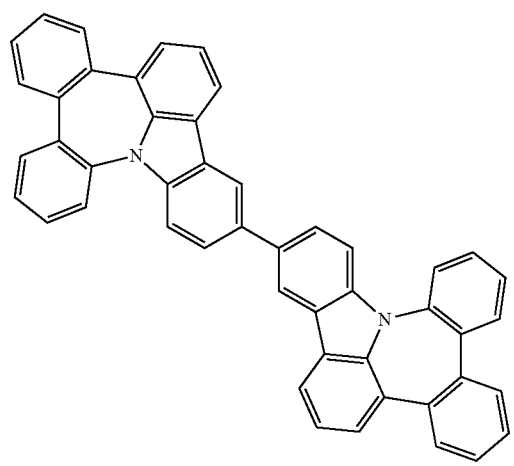
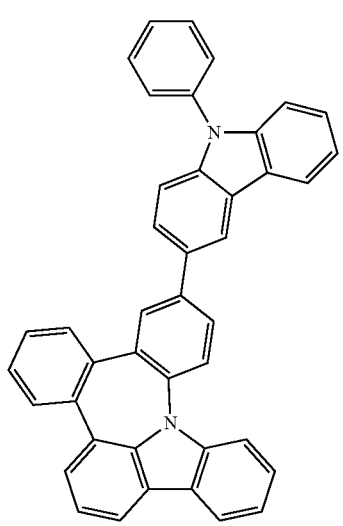
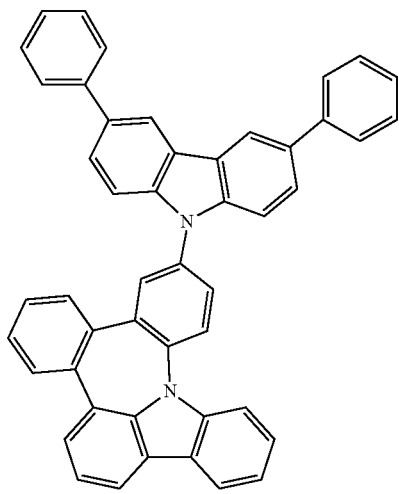
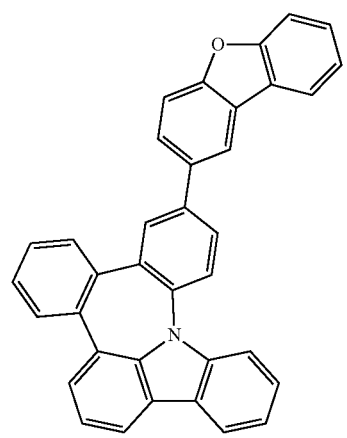
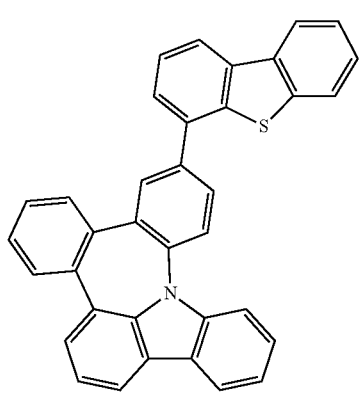
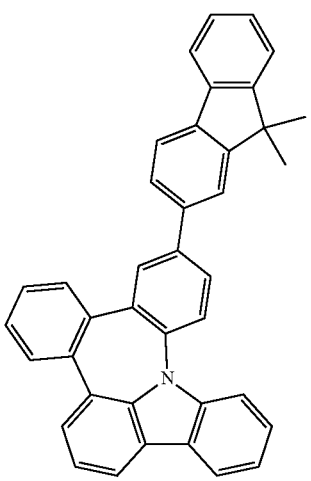
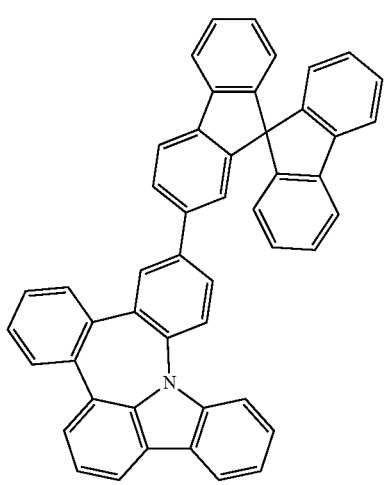

-continued
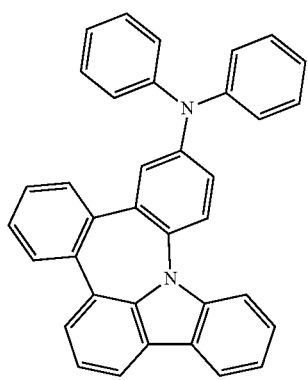
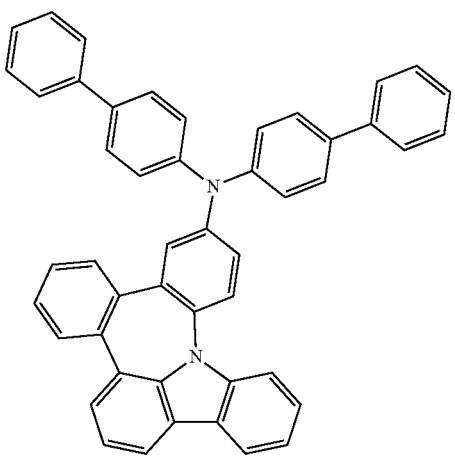
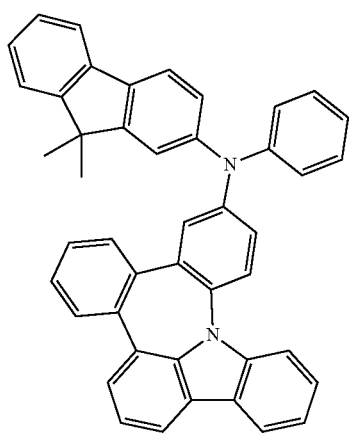
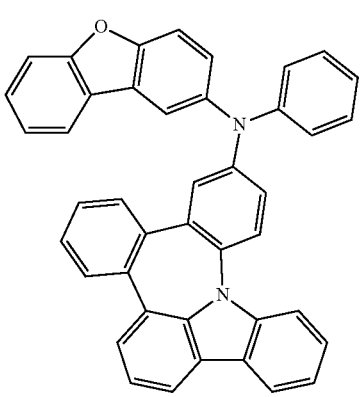
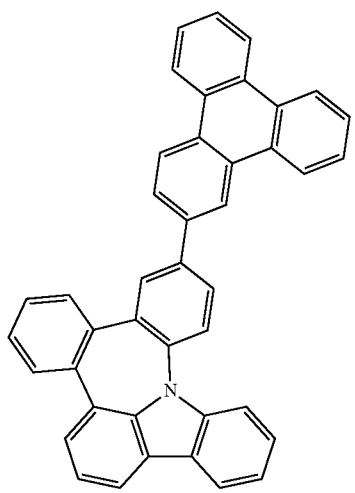
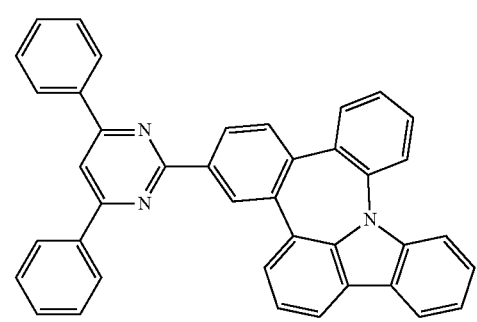

-continued
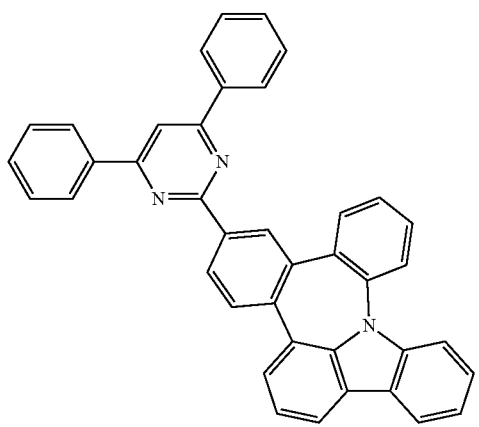
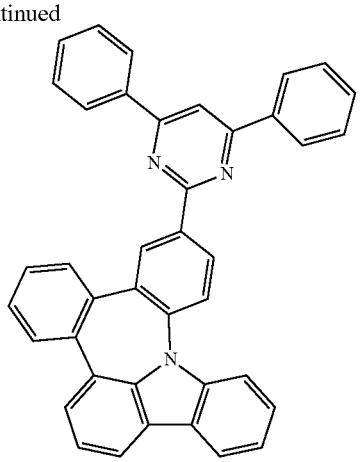
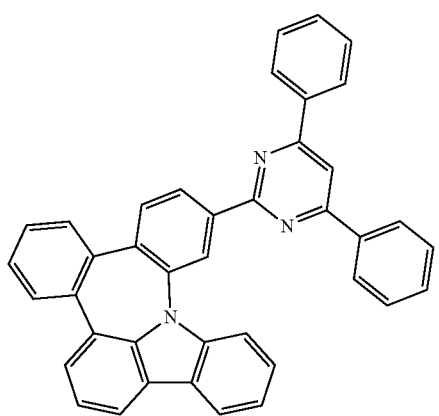
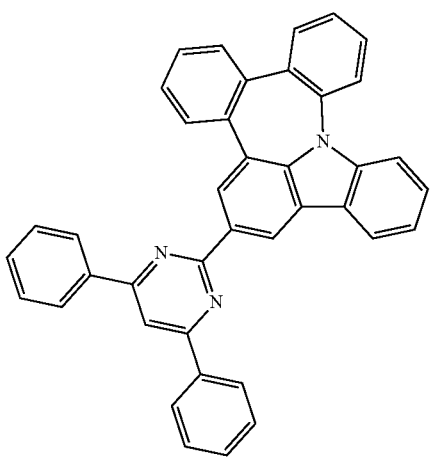
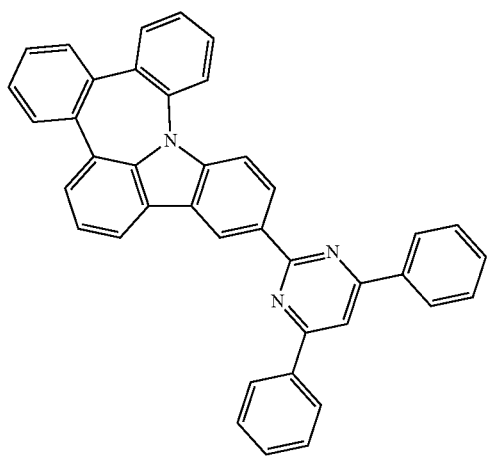
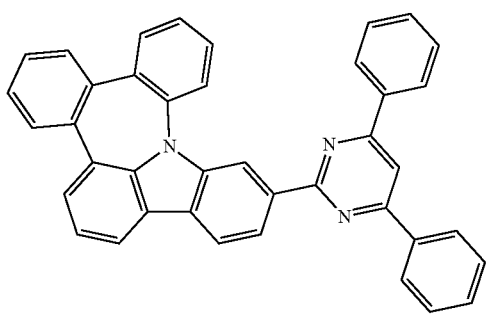

35
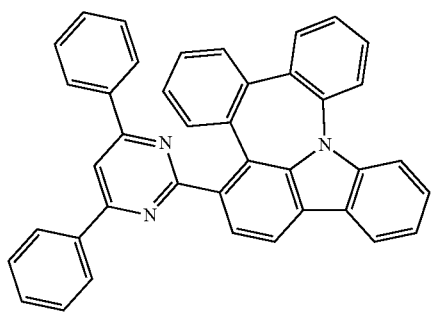
36
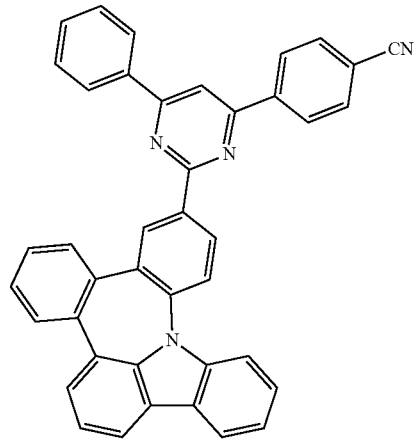
-continued
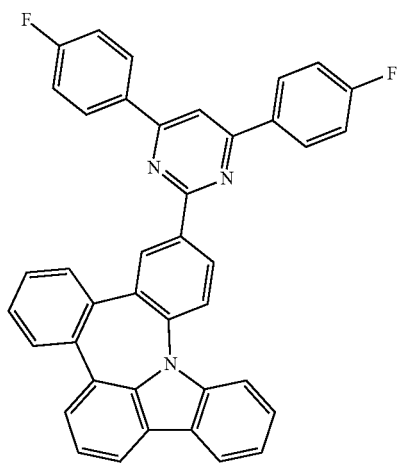
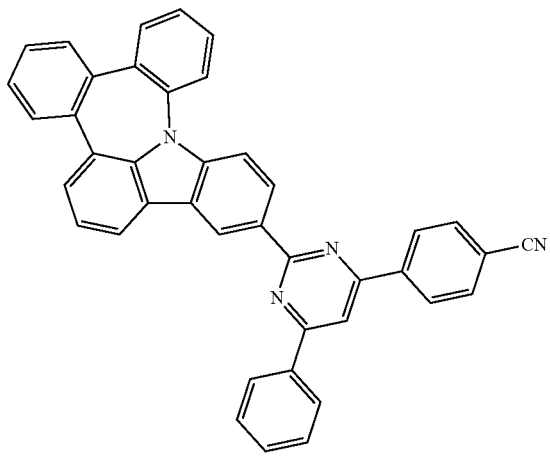
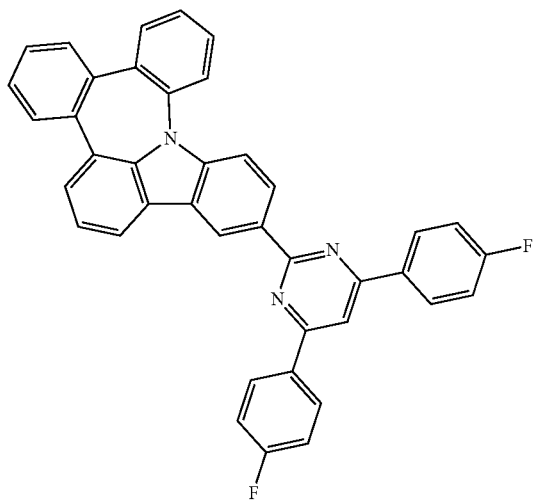
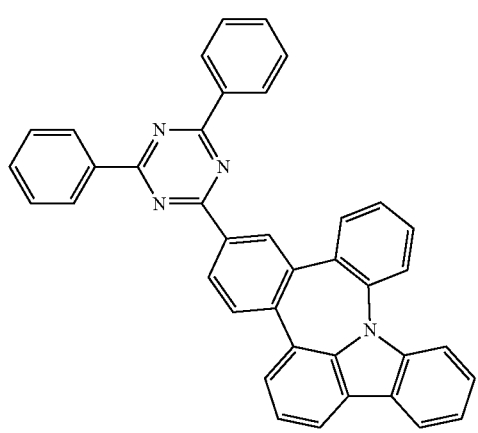

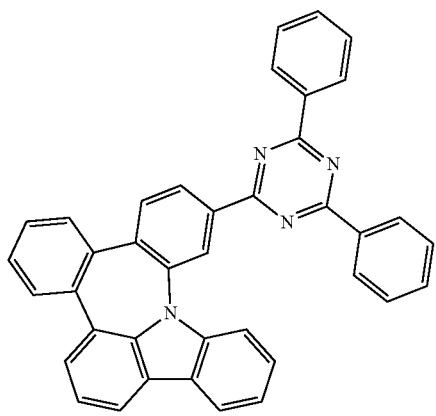
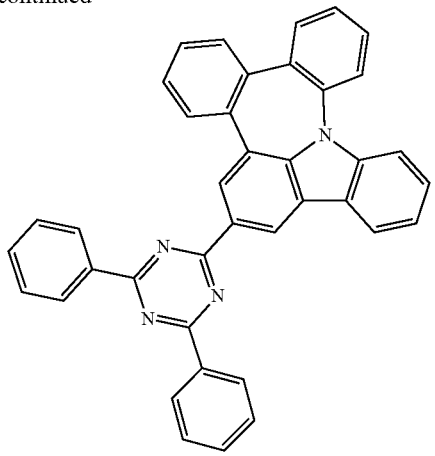
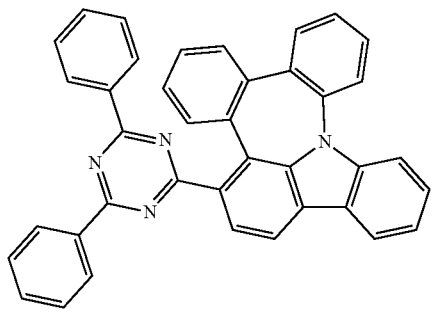
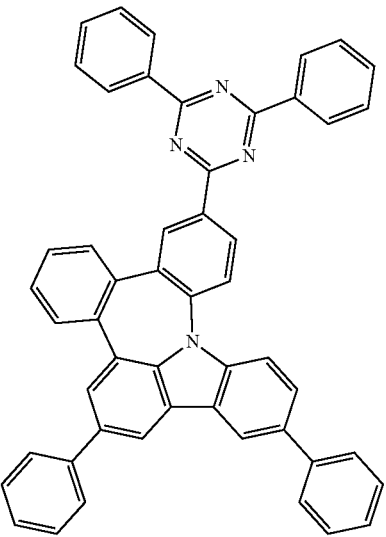
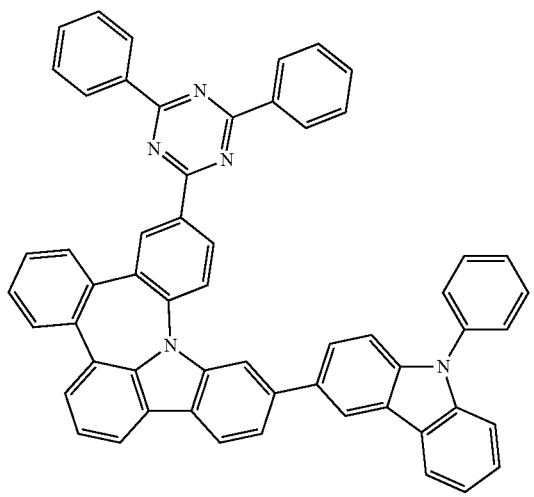
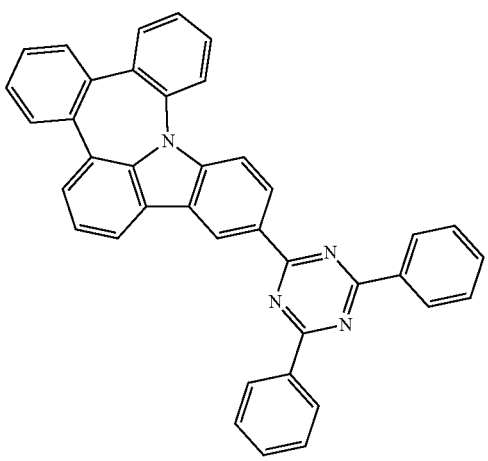

-continued
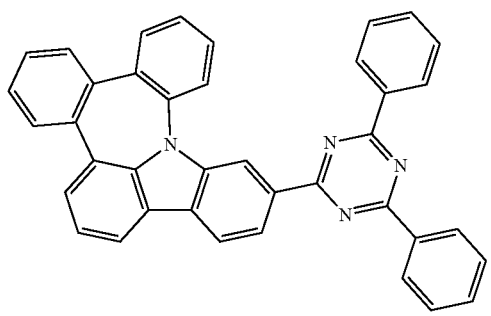
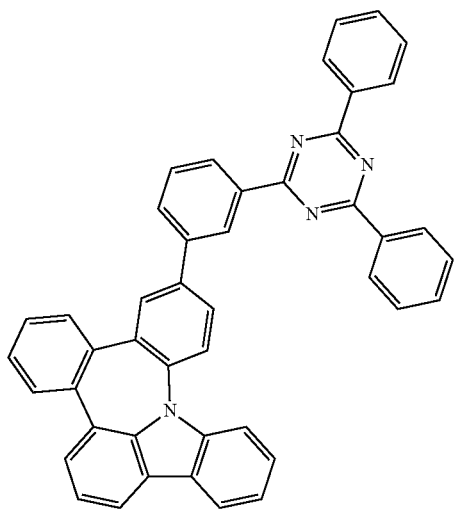
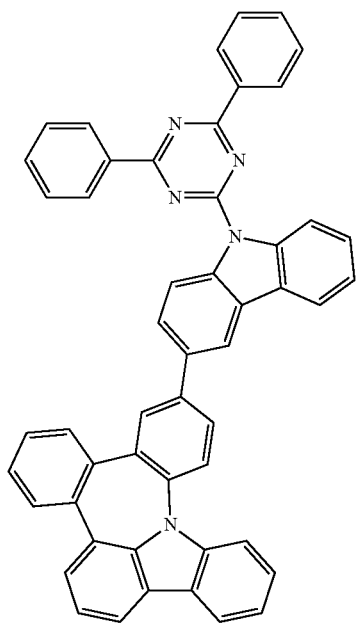
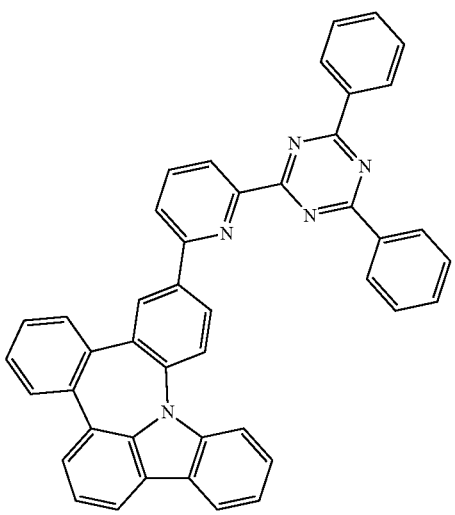
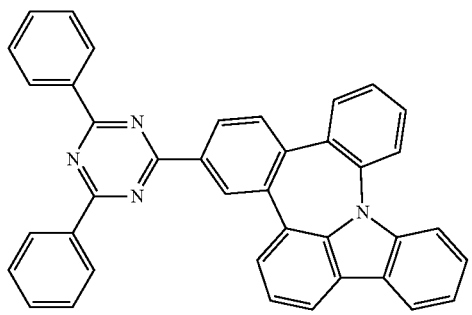
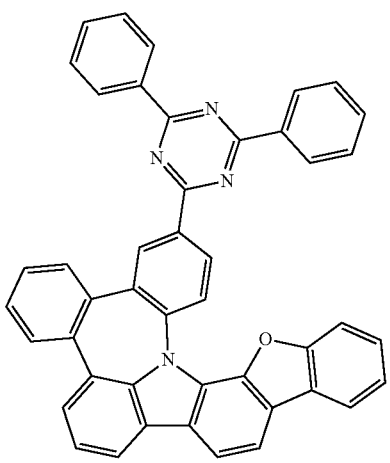

-continued
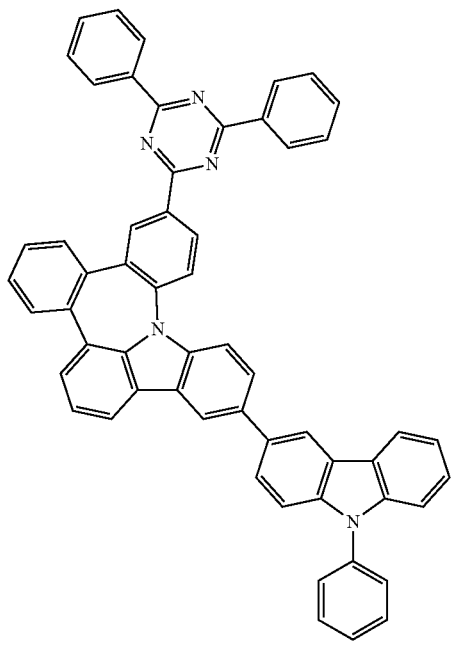
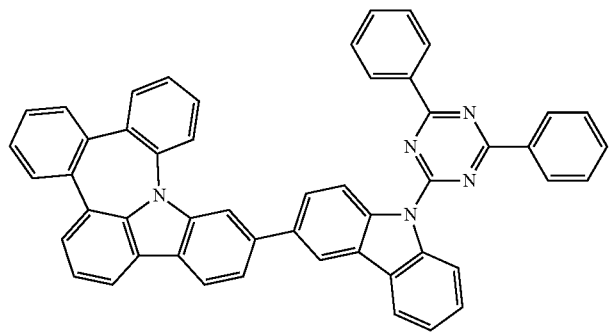
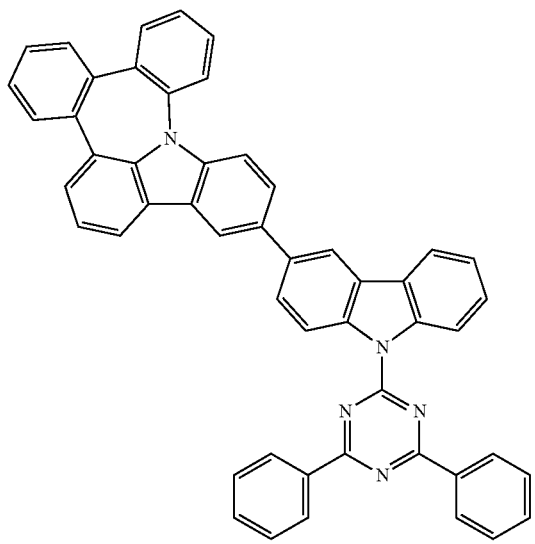
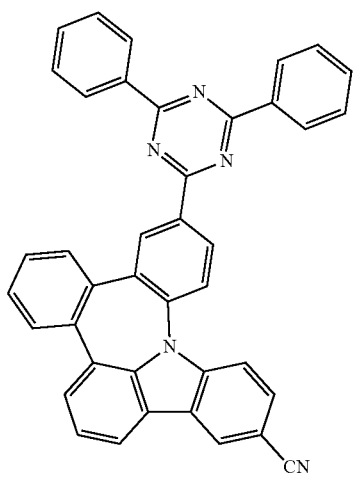
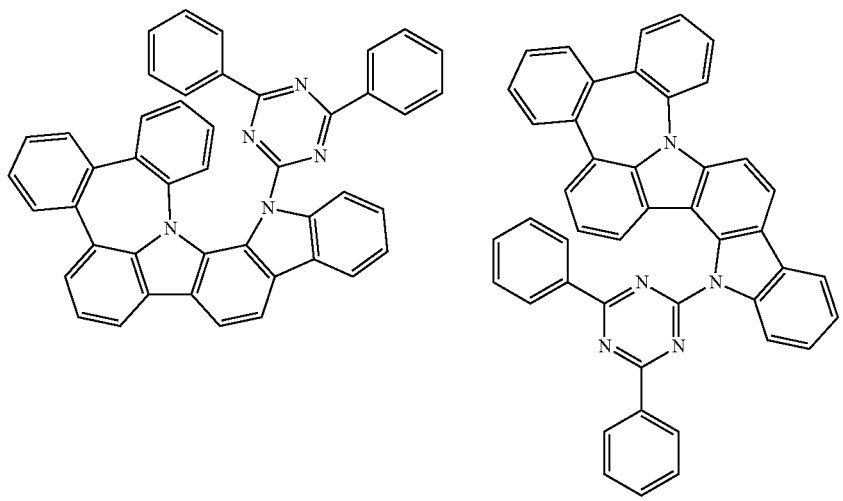

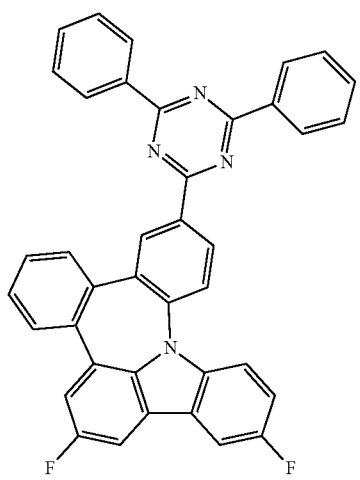
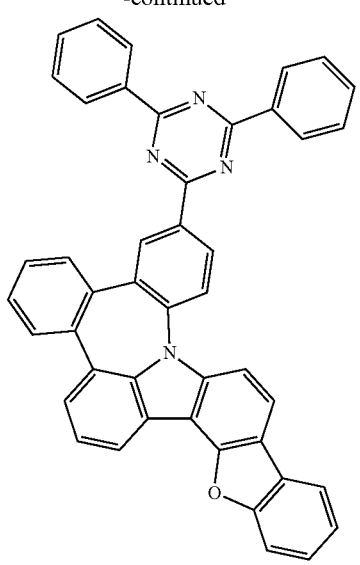
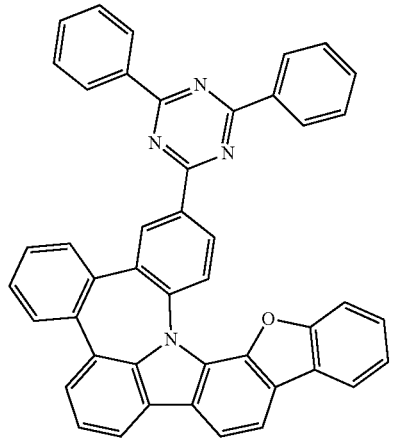
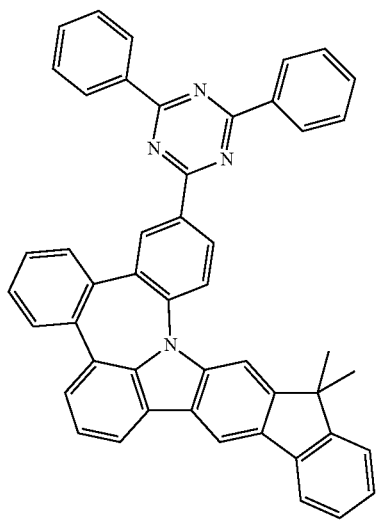
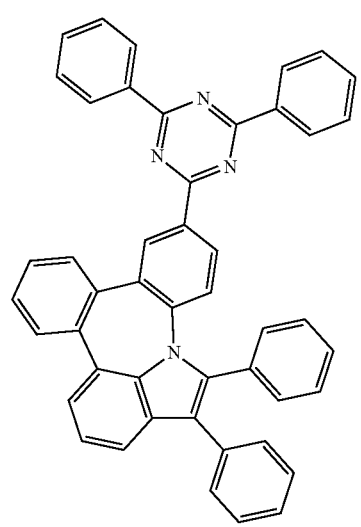
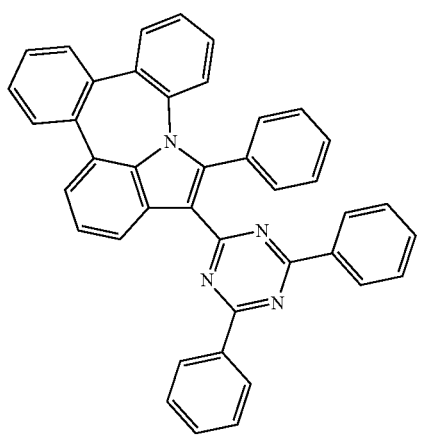
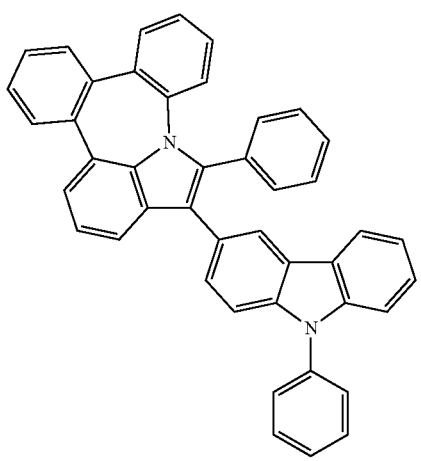

-continued
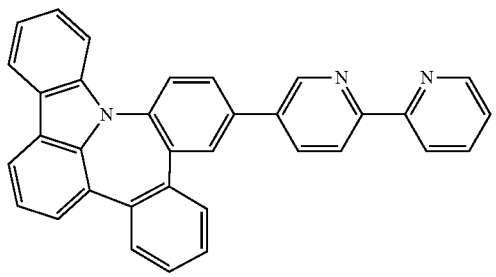
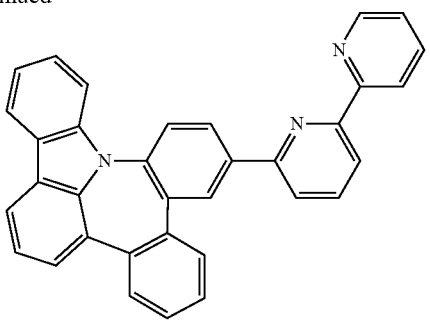
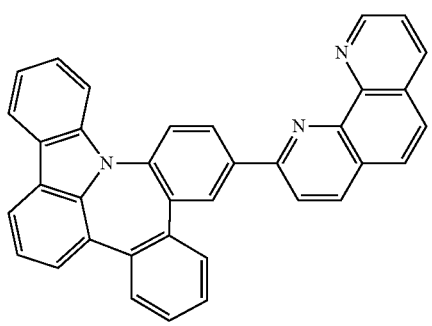
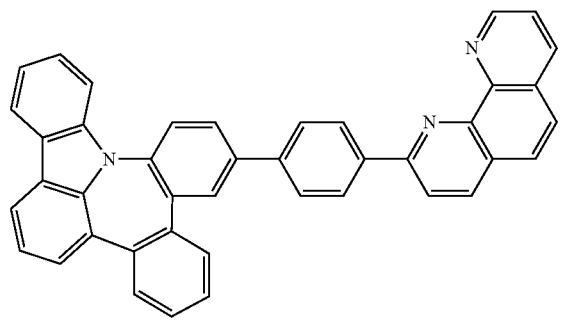
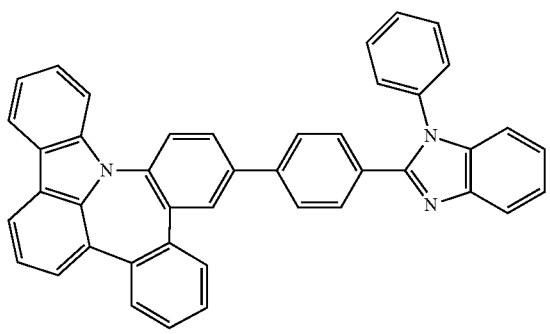
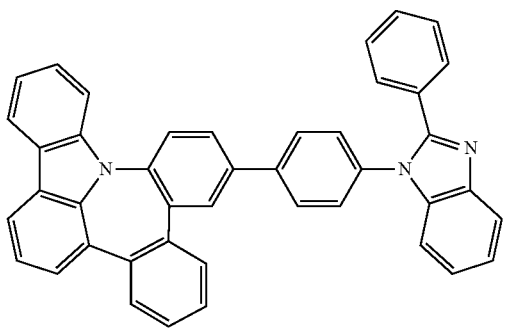
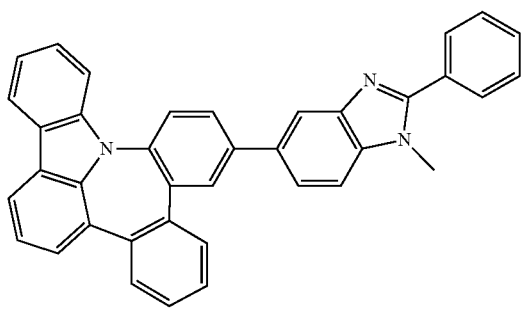
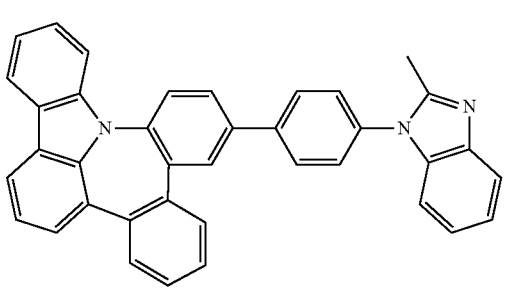
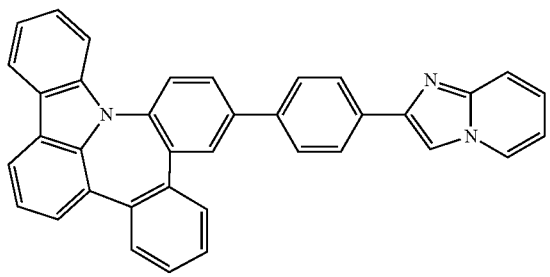
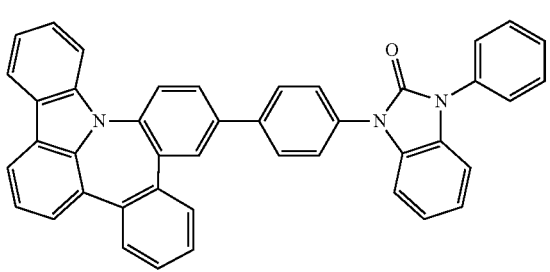

-continued
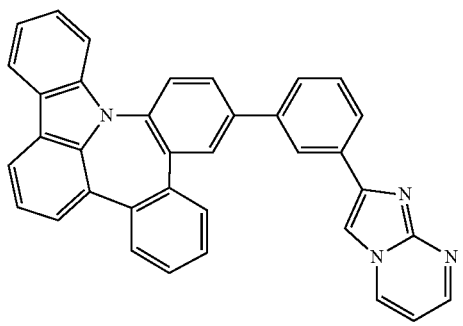 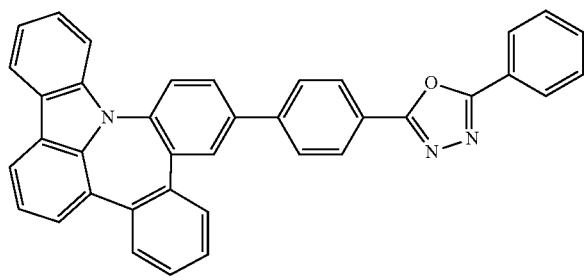
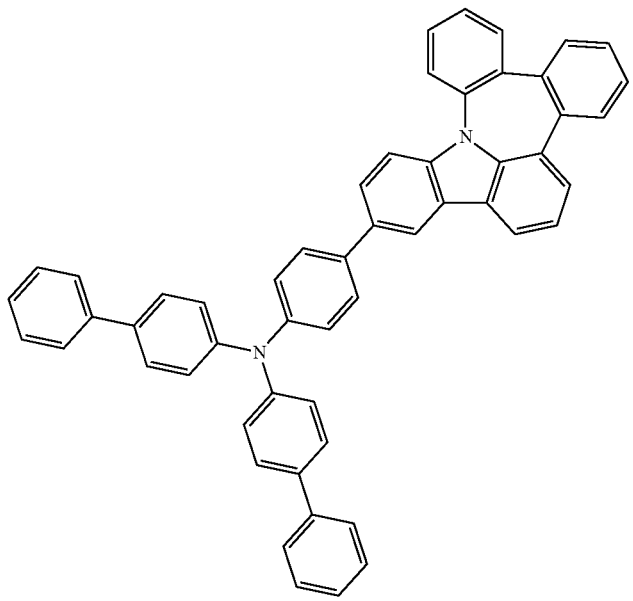
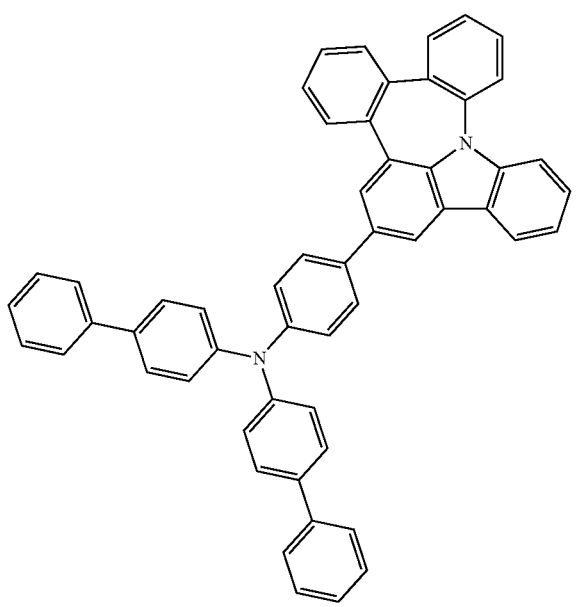

-continued
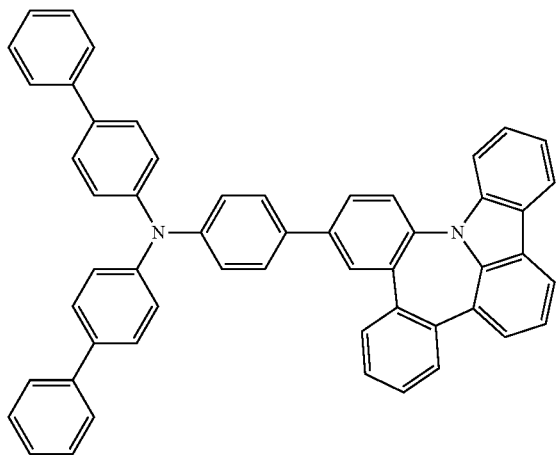
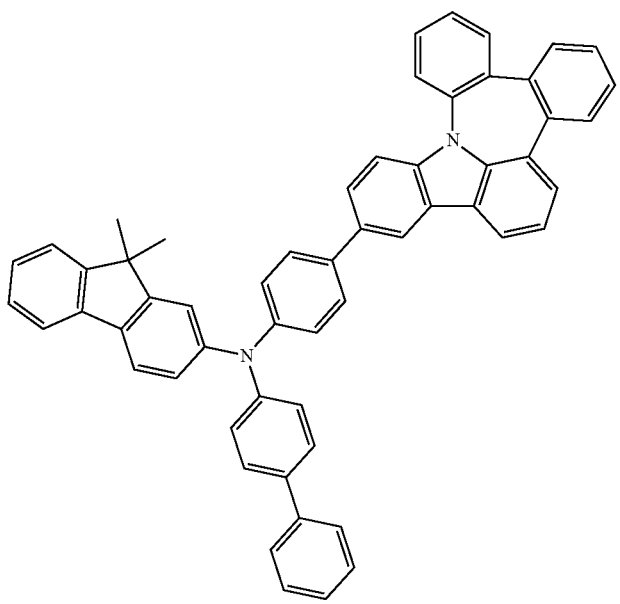
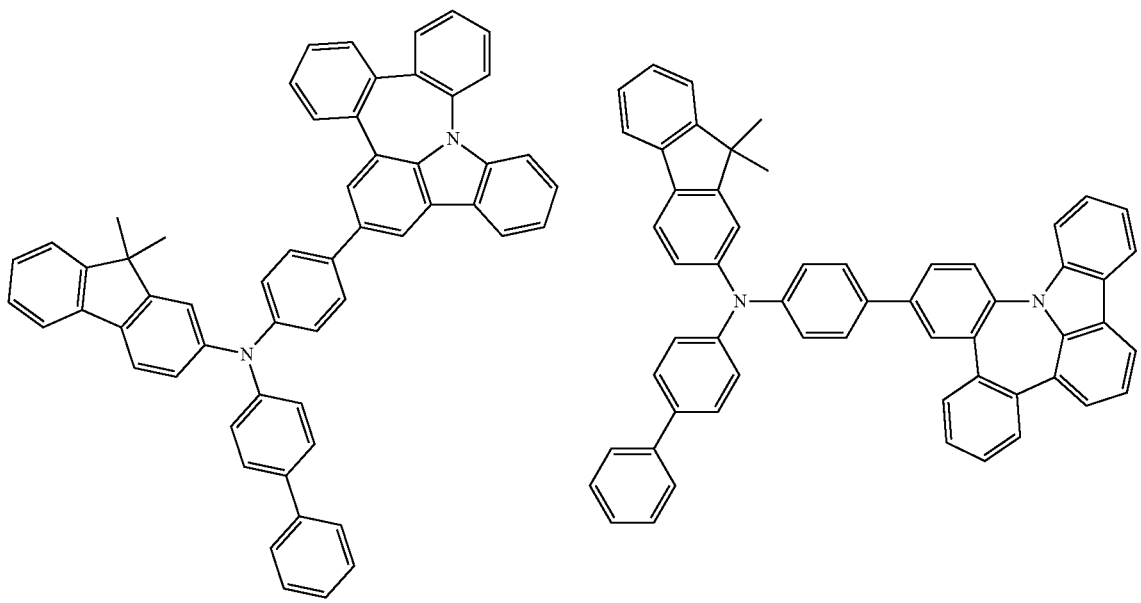

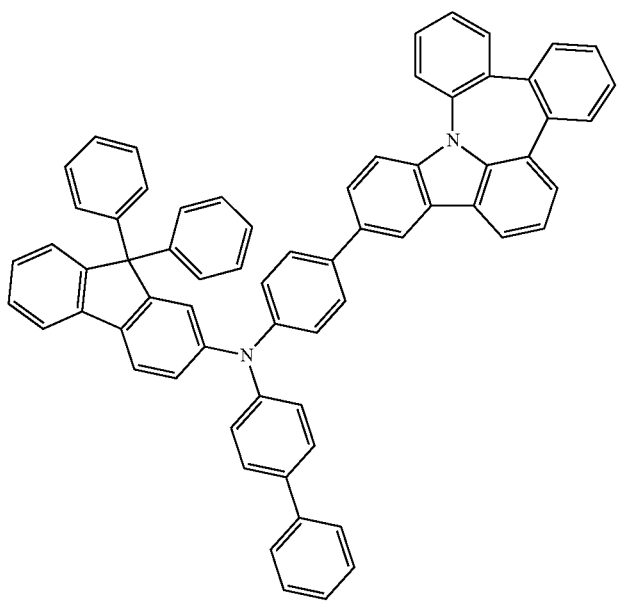
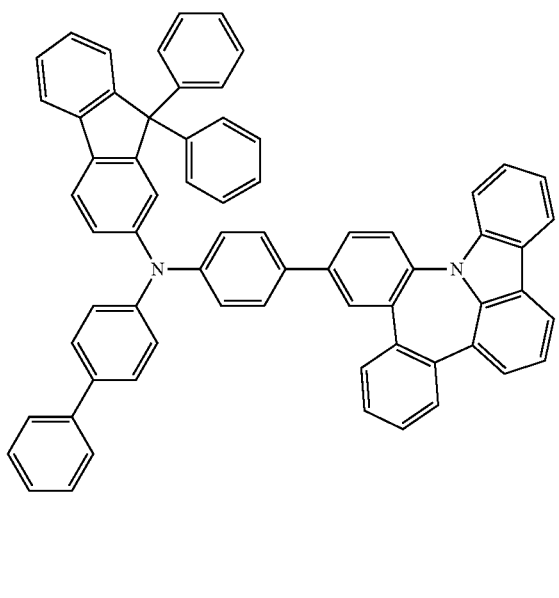

-continued
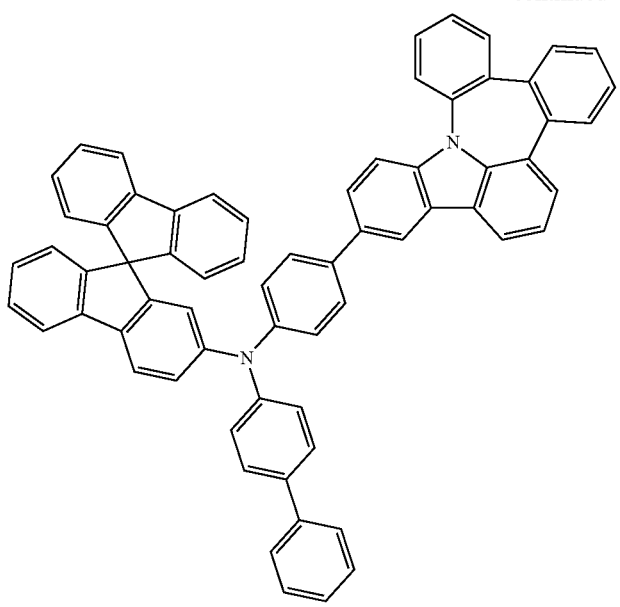
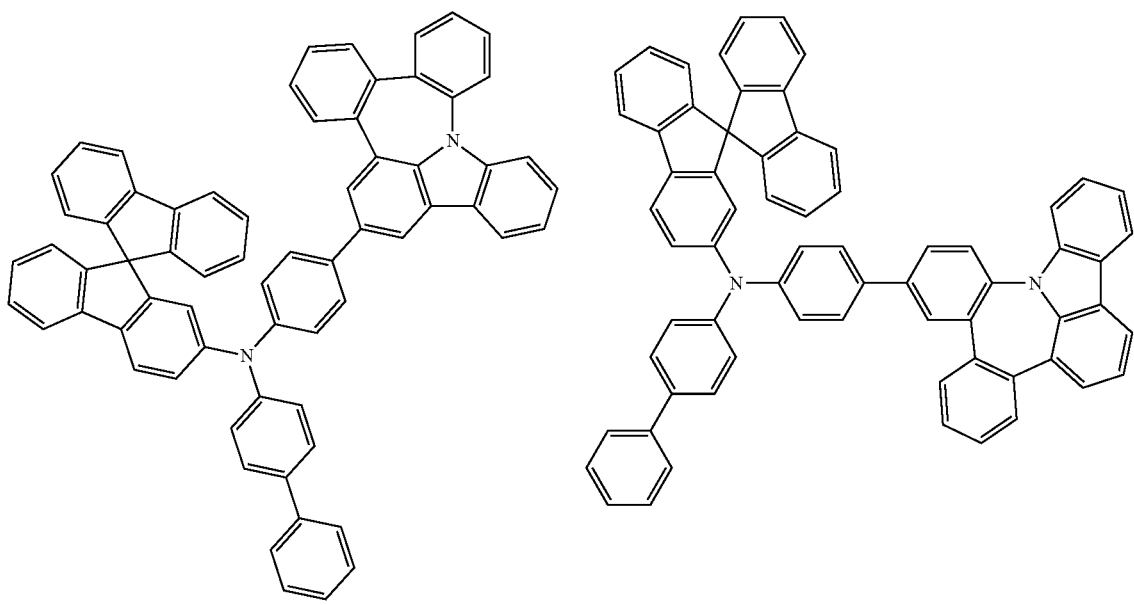

-continued
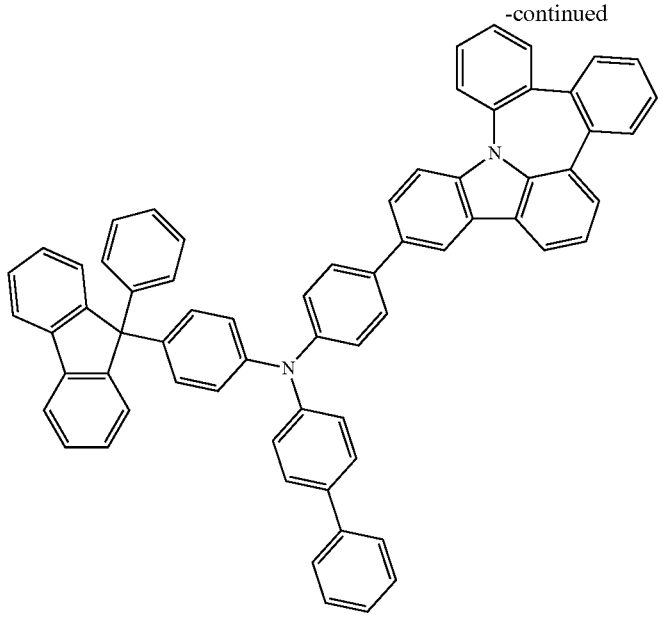
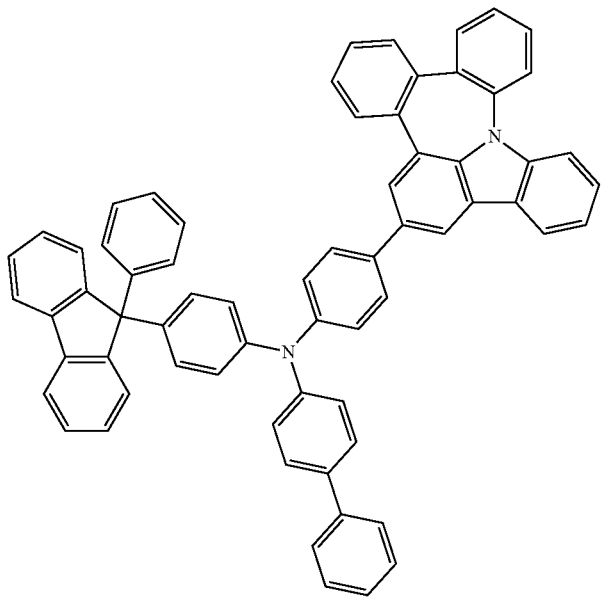
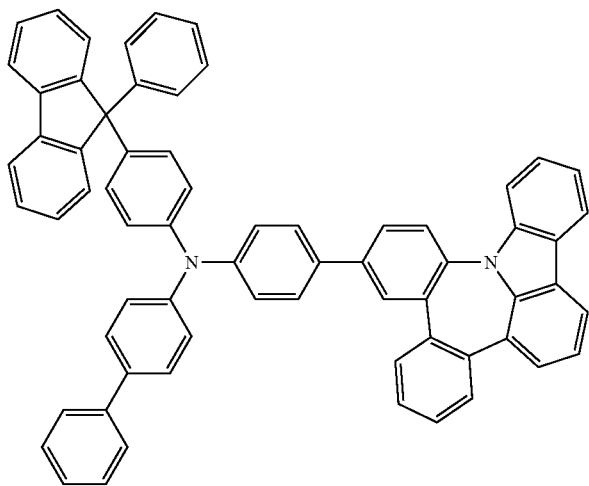

-continued
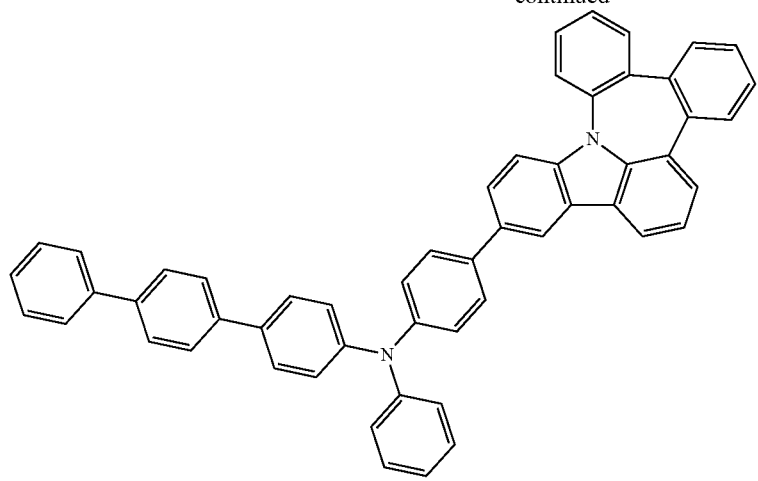
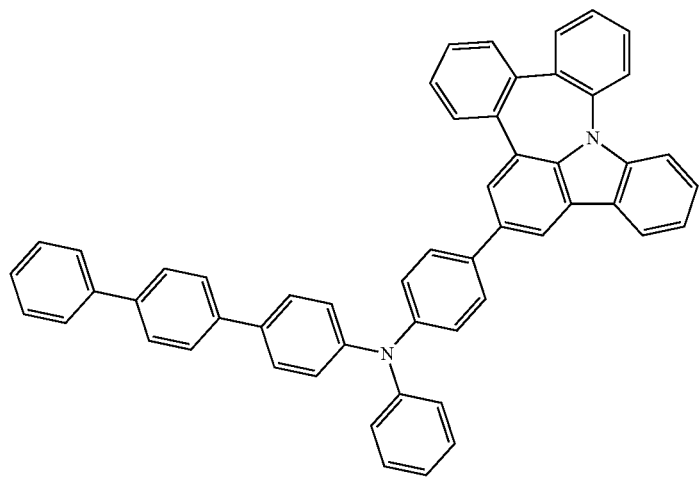
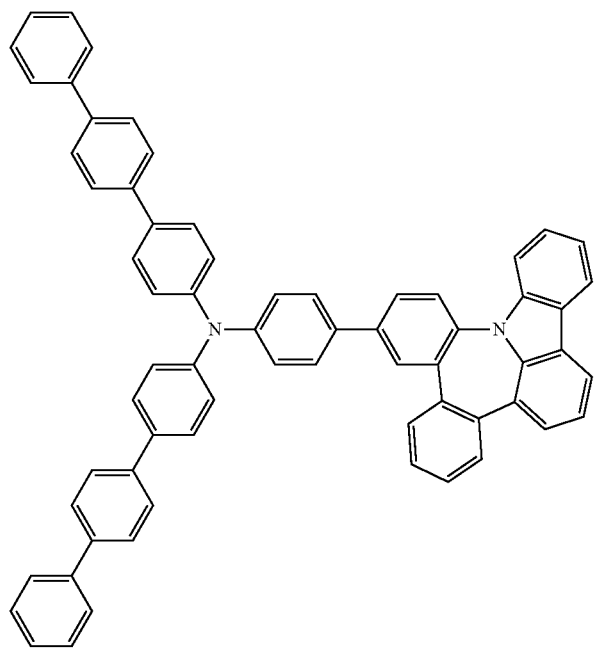

-continued
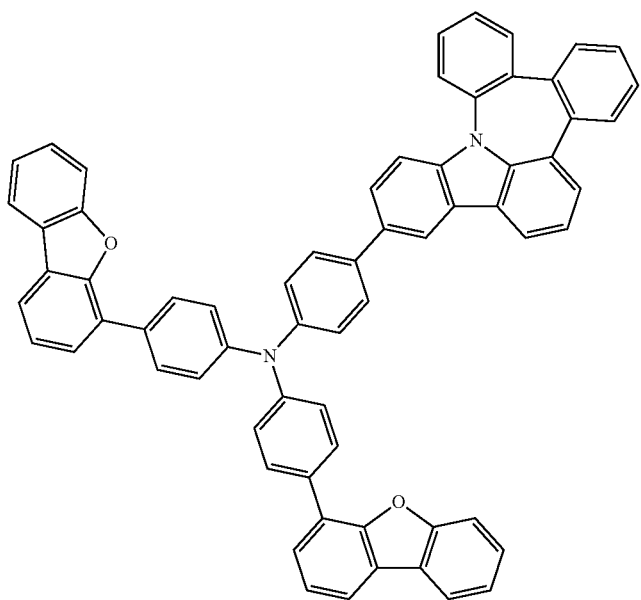
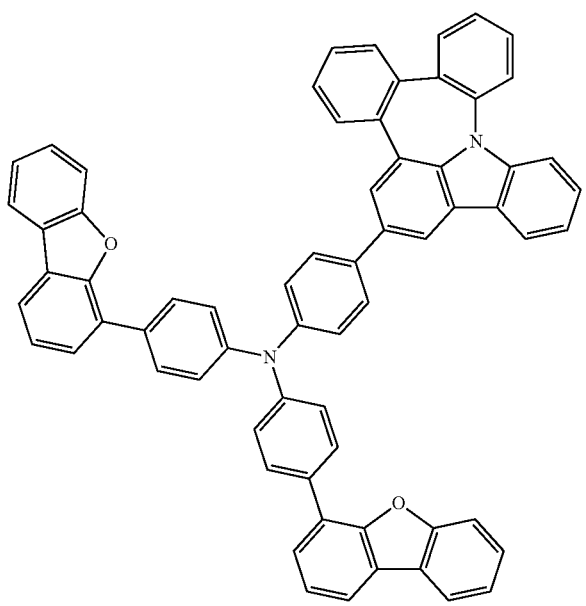

-continued
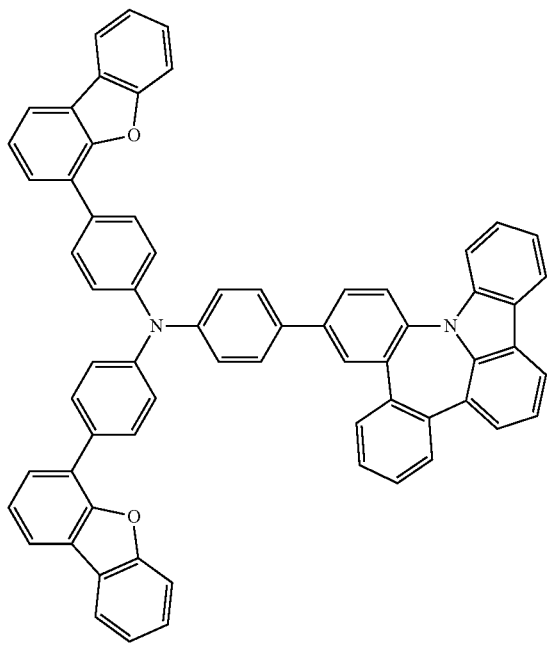
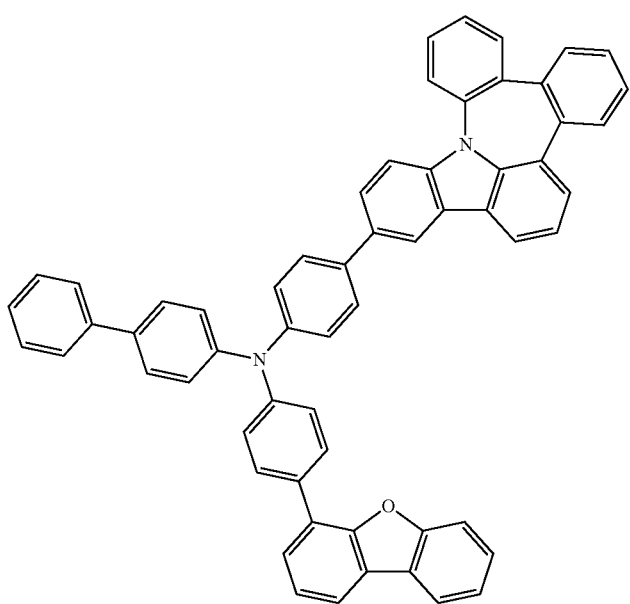

-continued
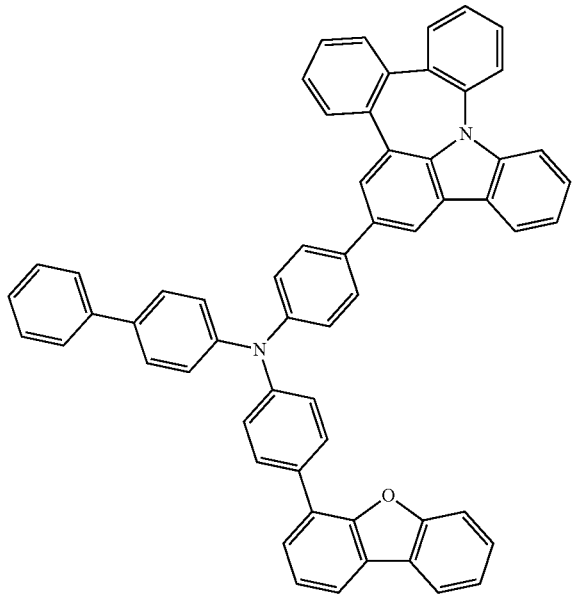
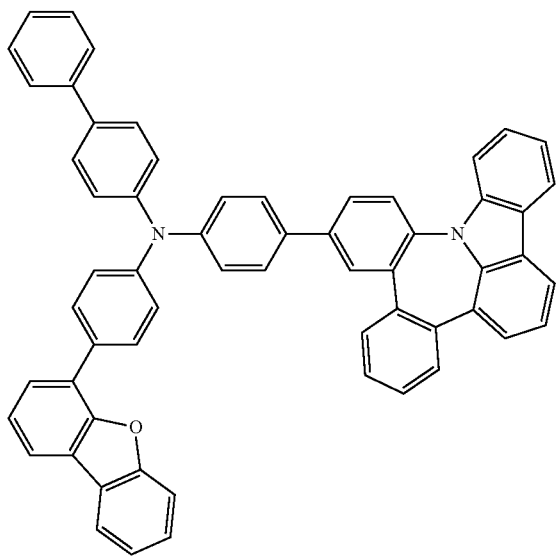
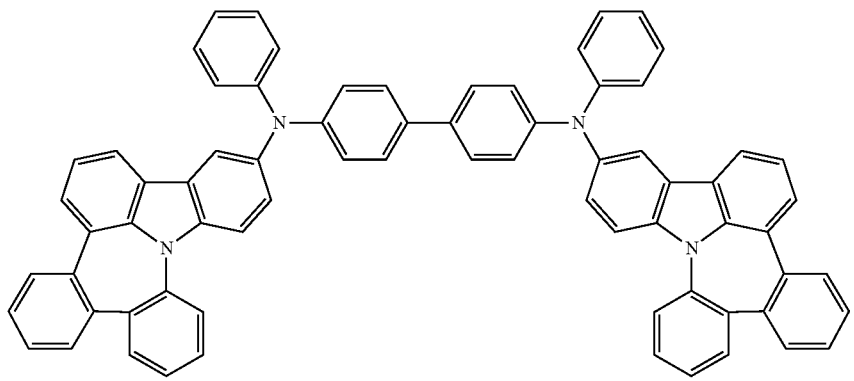

-continued
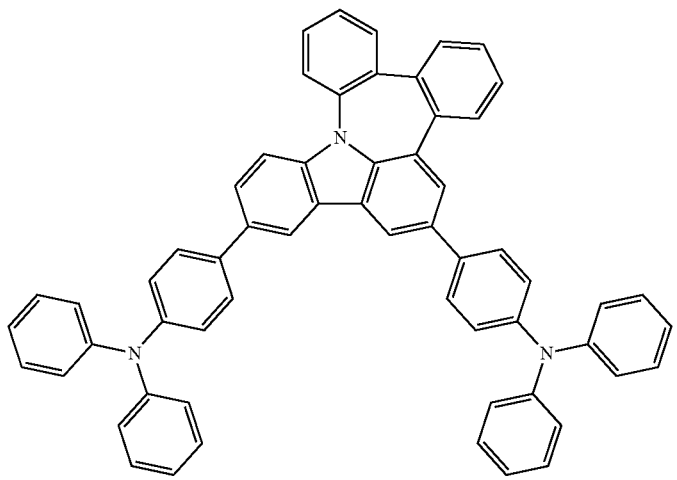
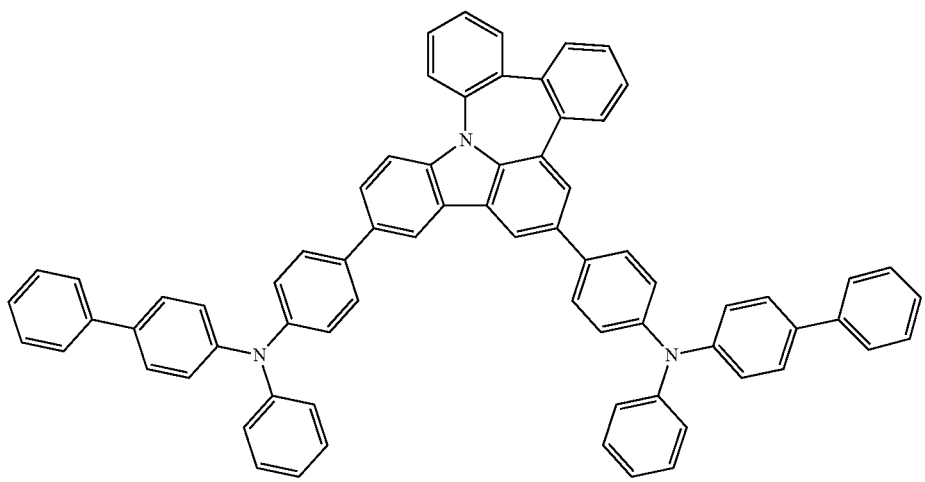
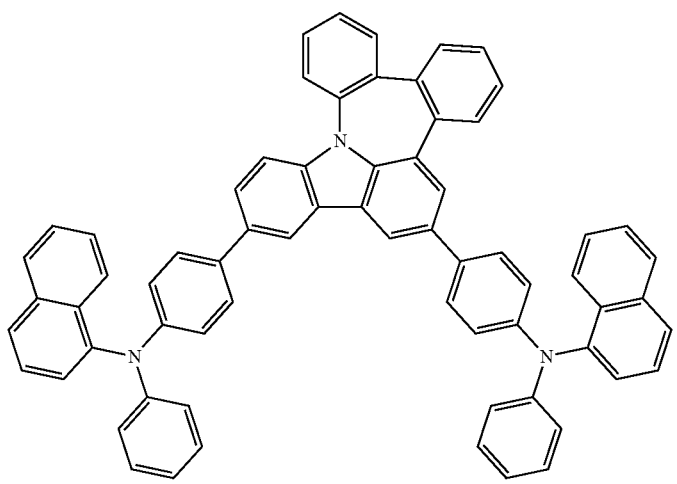

-continued
| 67 | 68 |
|---|---|
| 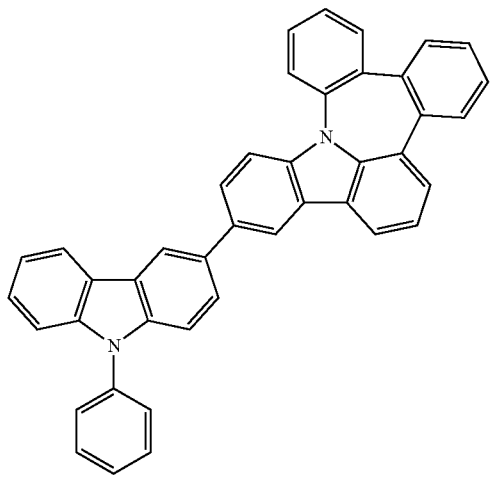 | 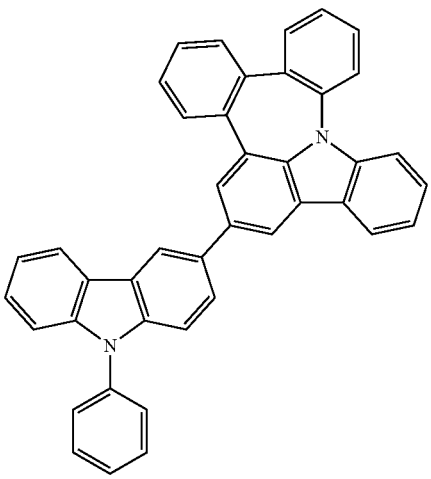 |
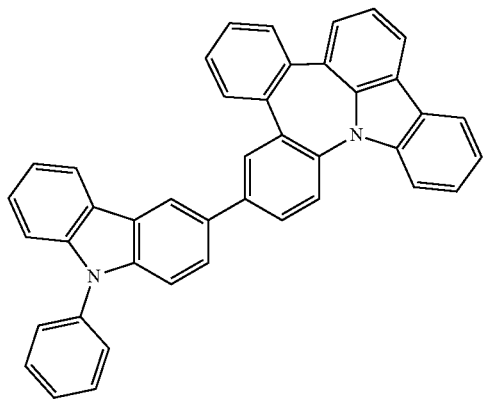
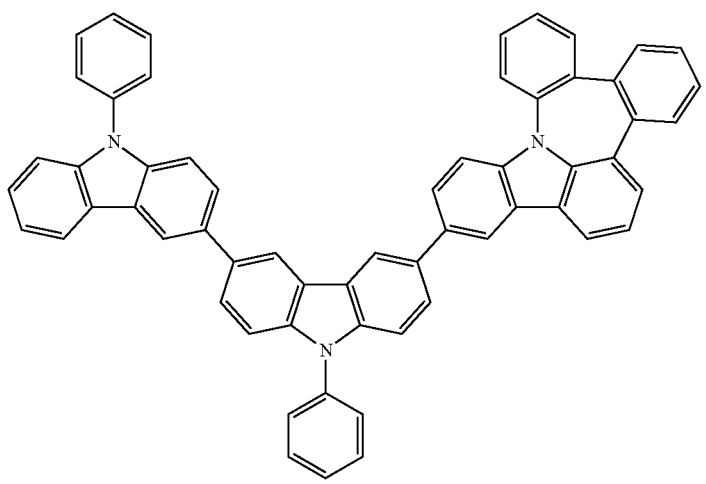

-continued
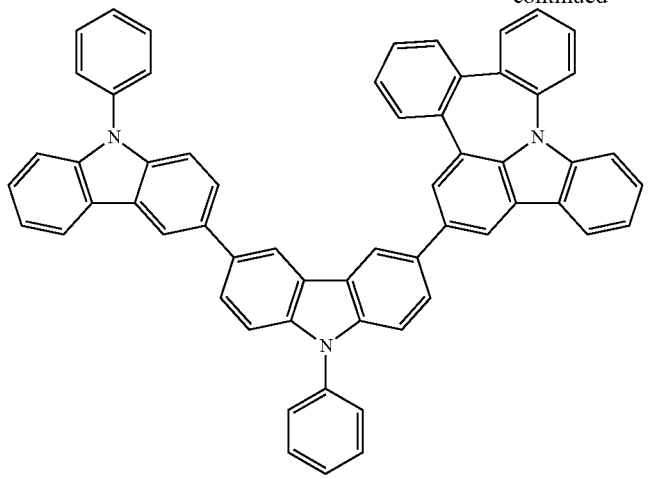
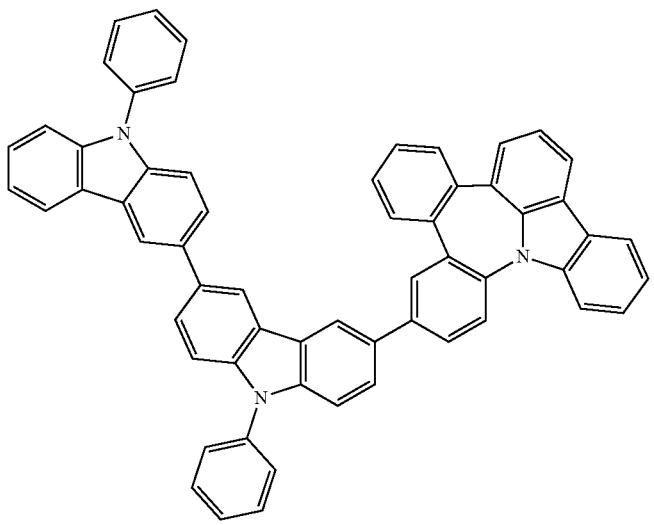
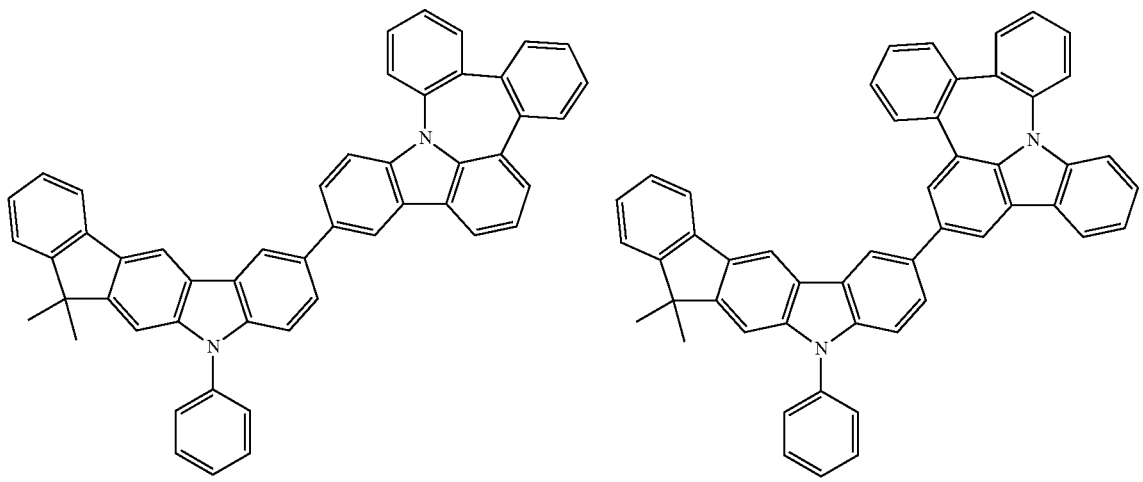

-continued
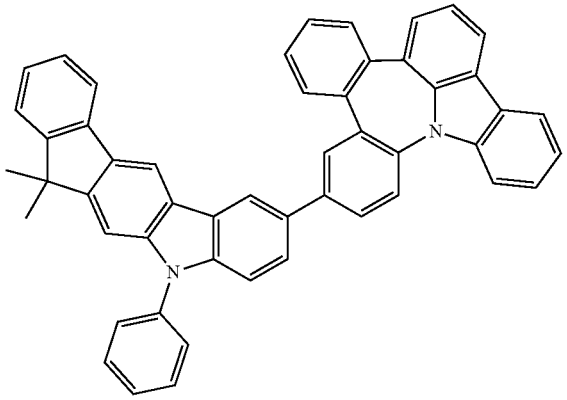
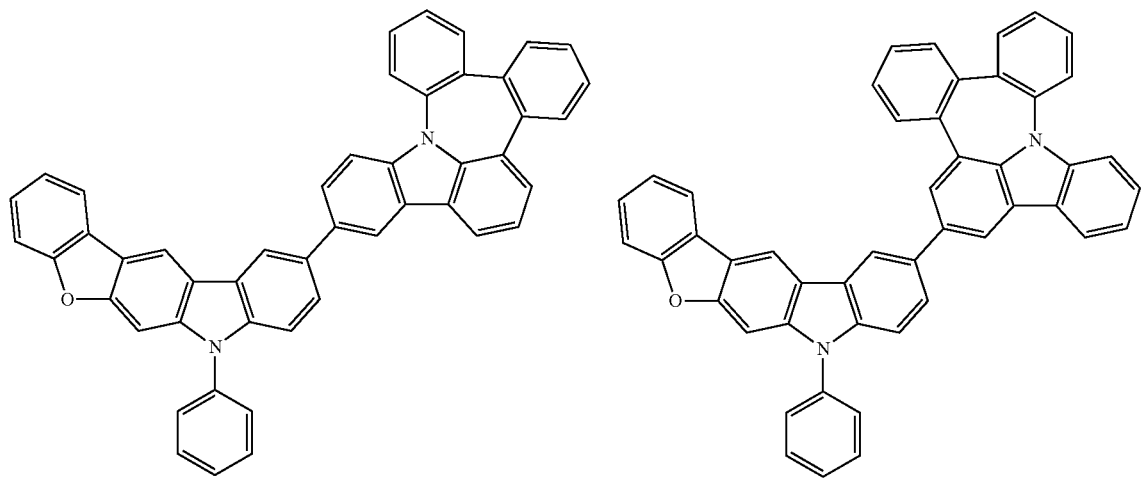
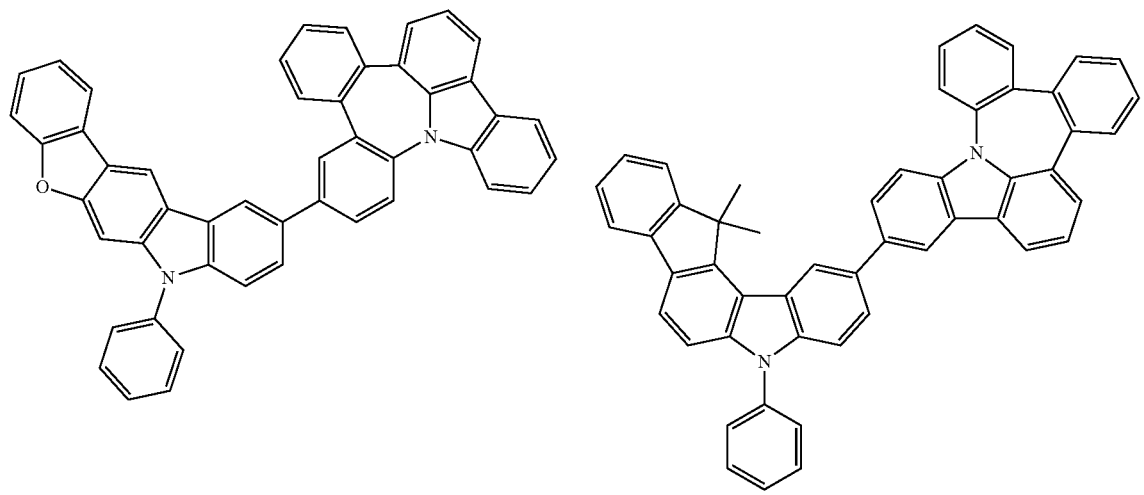

-continued
73
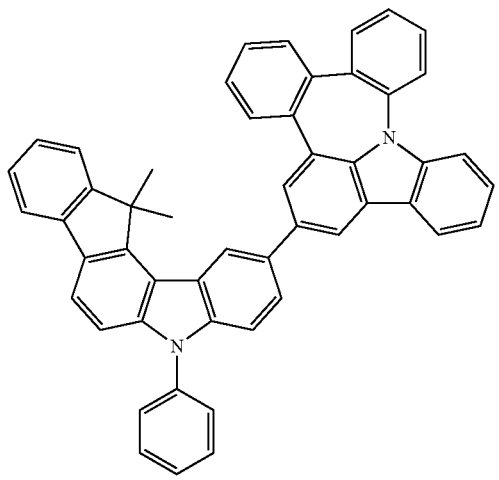
74
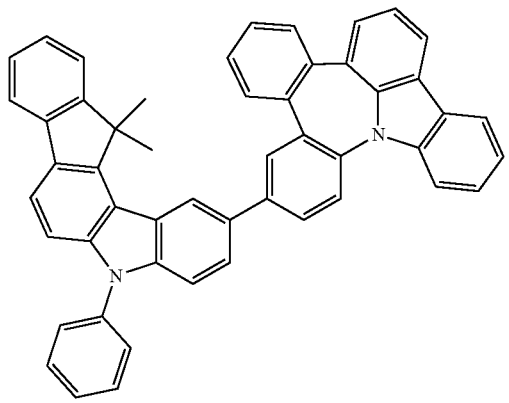
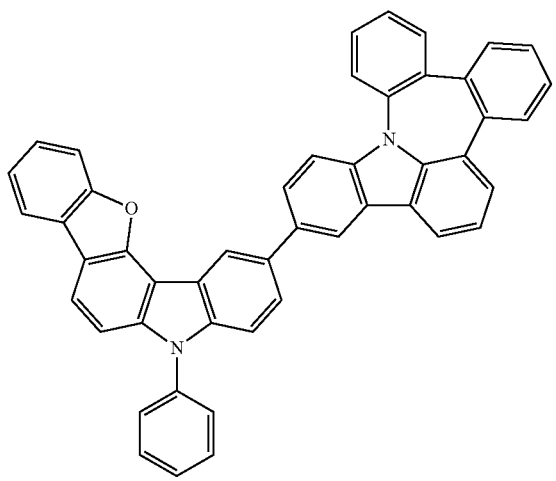
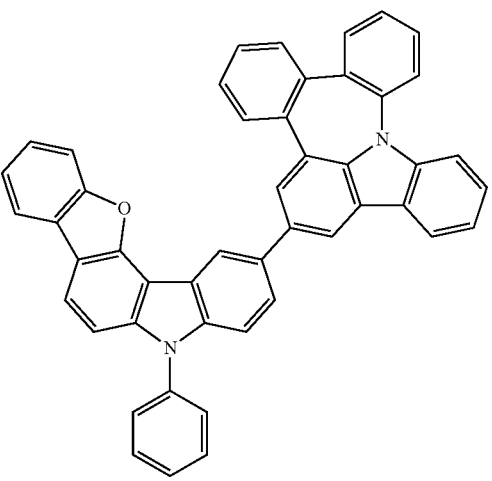
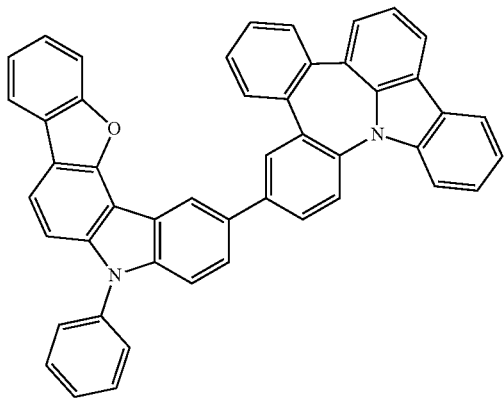
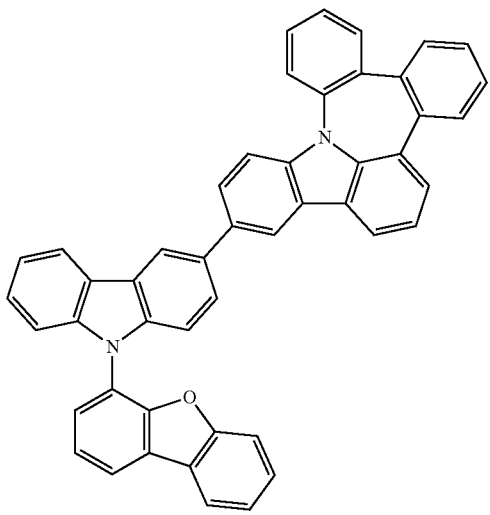

-continued
75
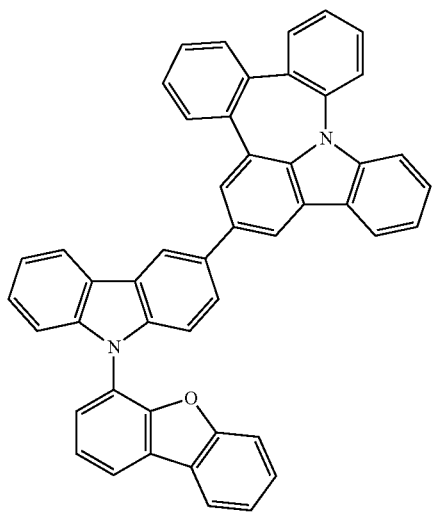
76
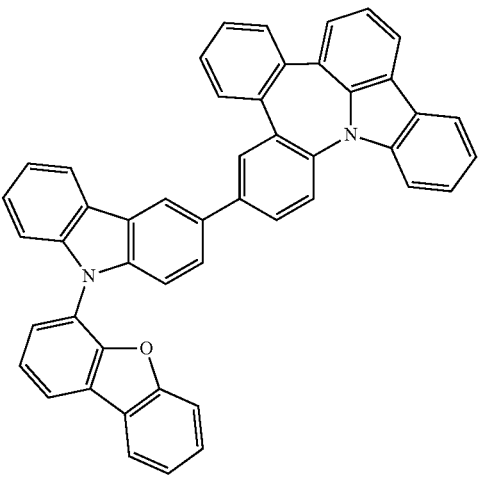
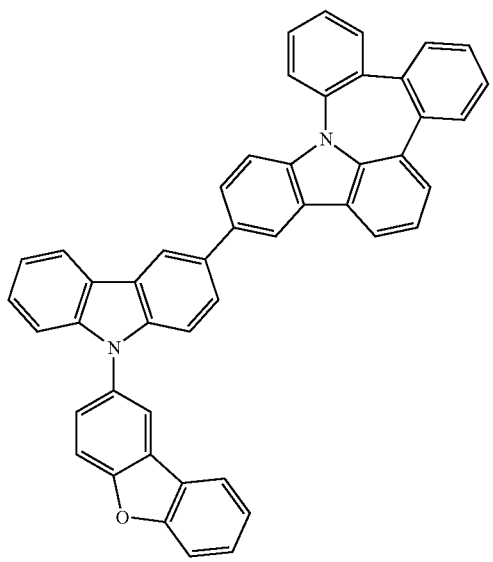
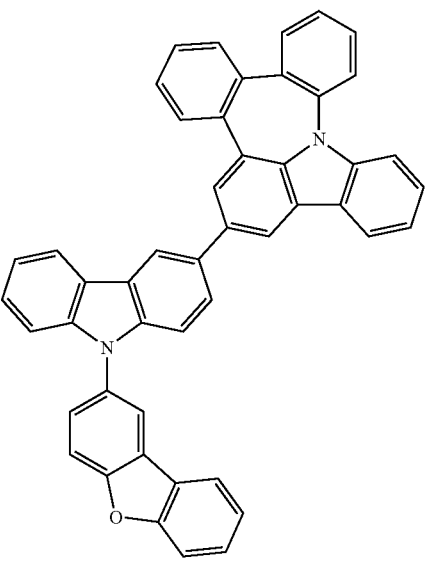
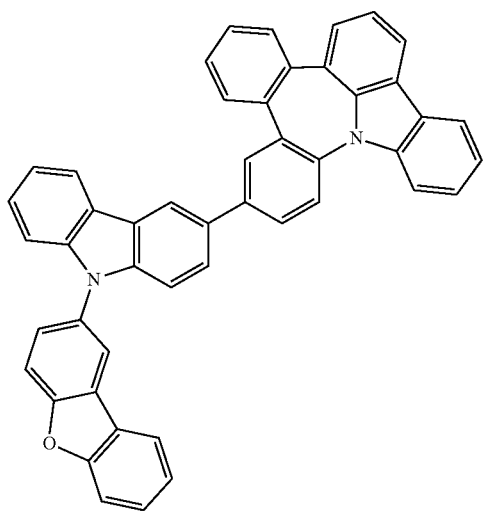
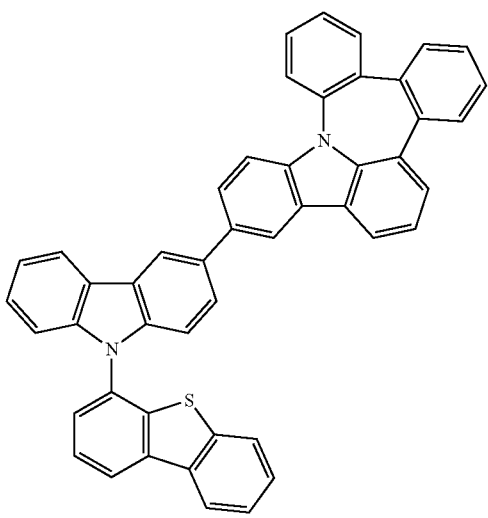

-continued
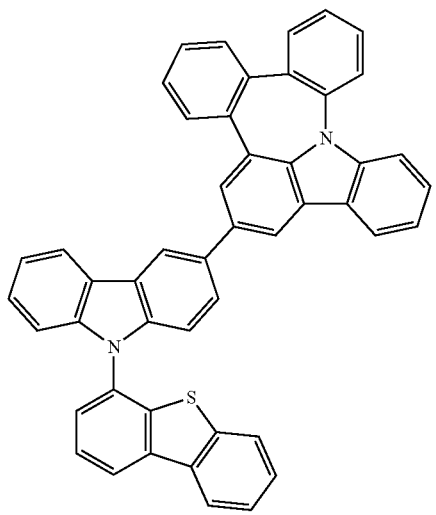
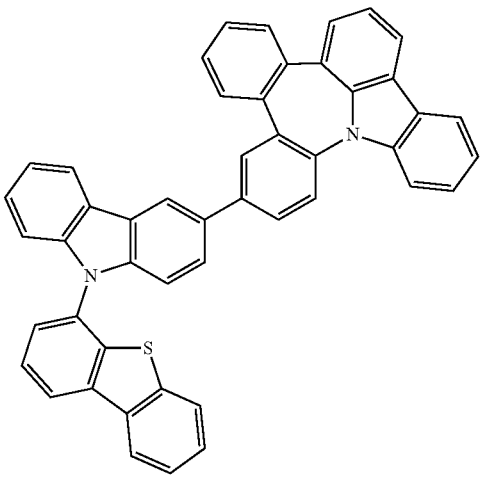
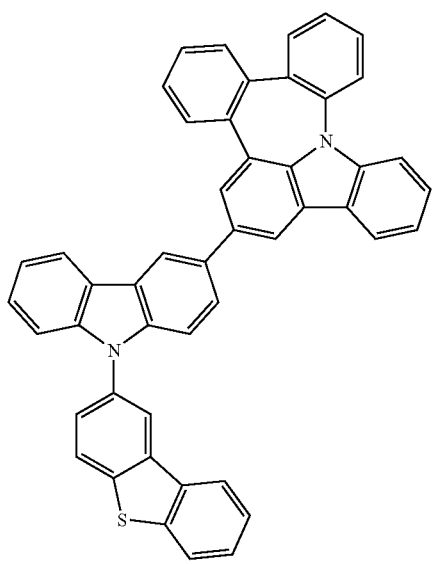
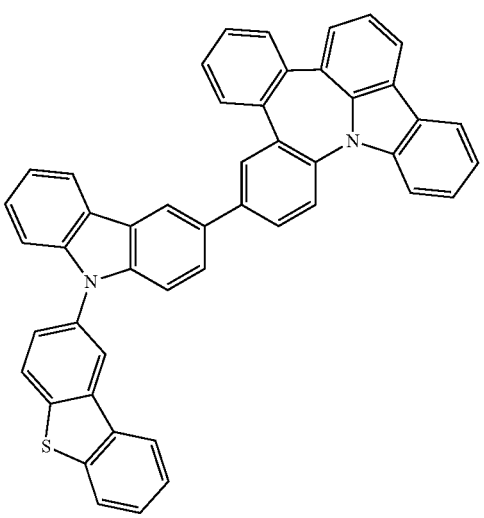
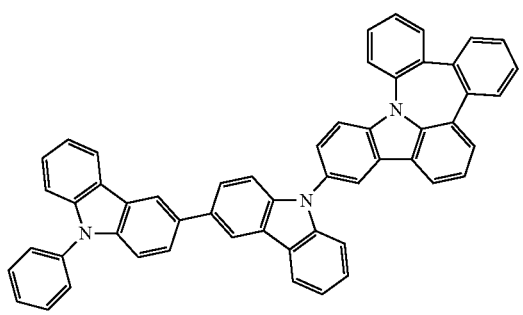

-continued
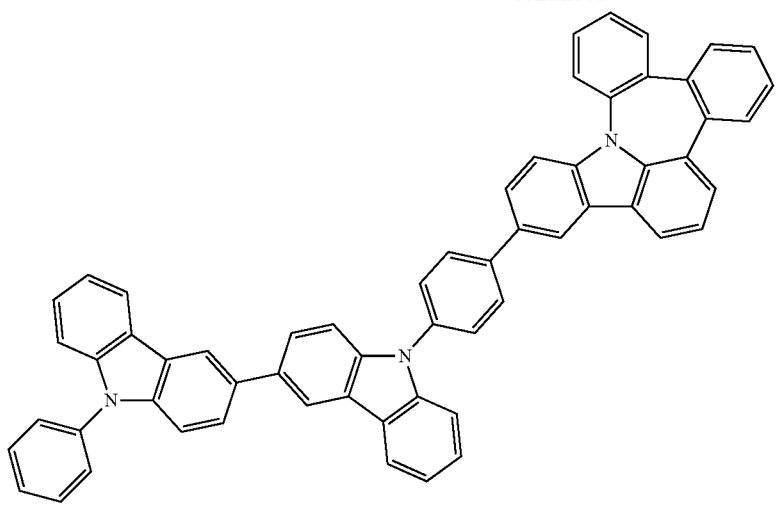
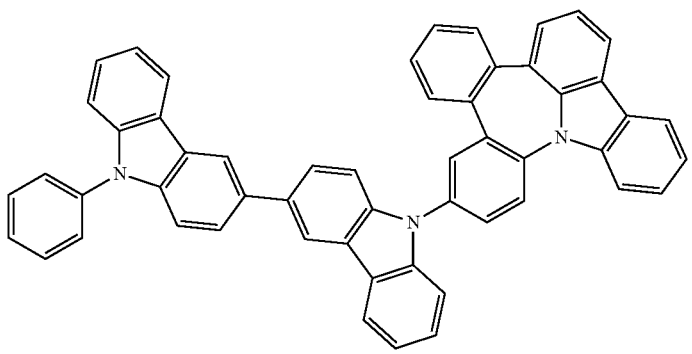
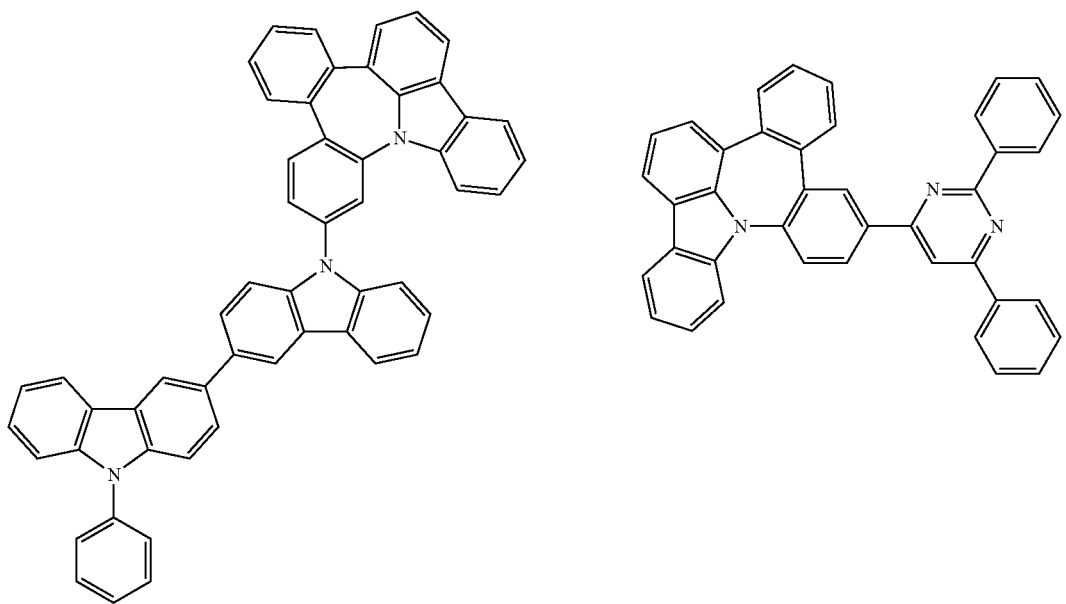

81
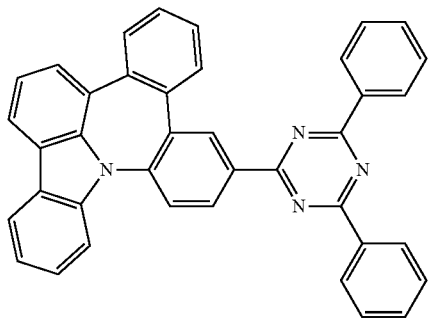
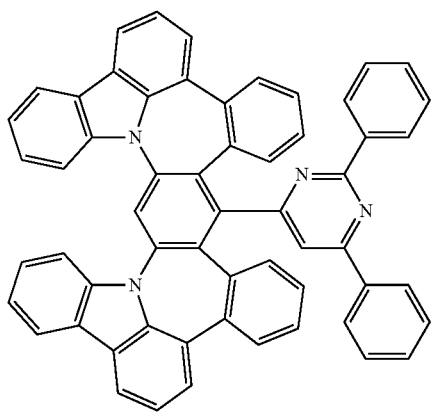
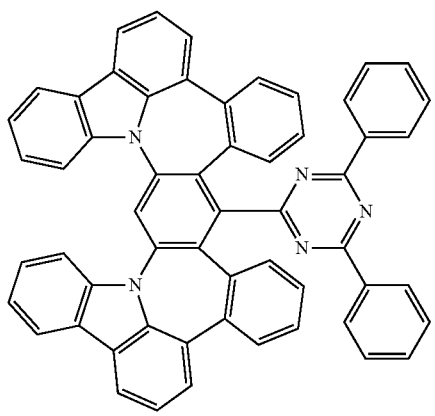
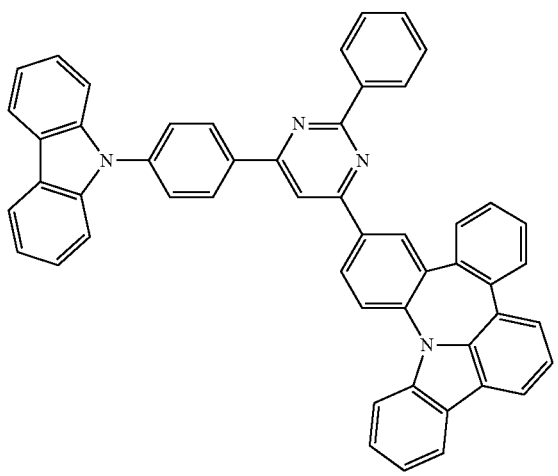
82
-continued
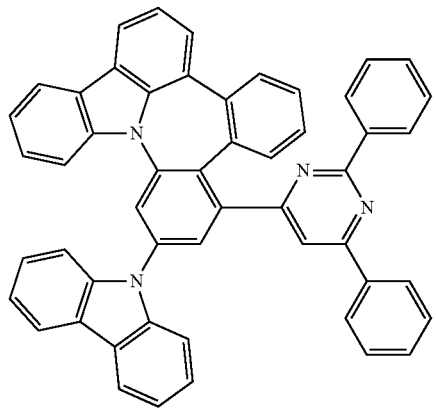
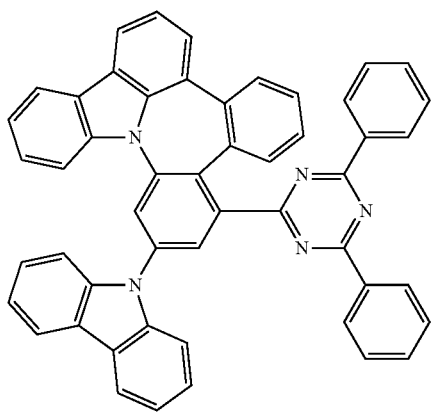
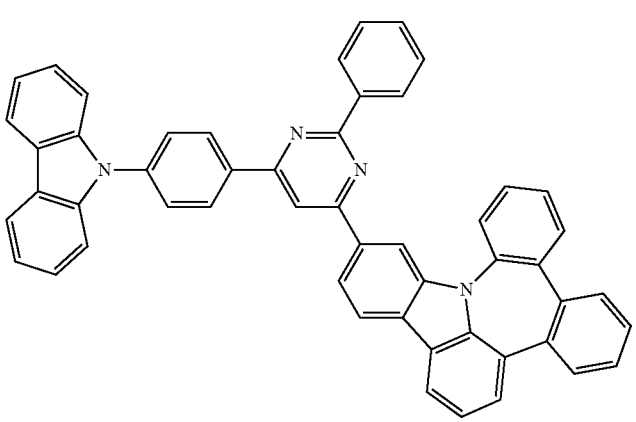

-continued
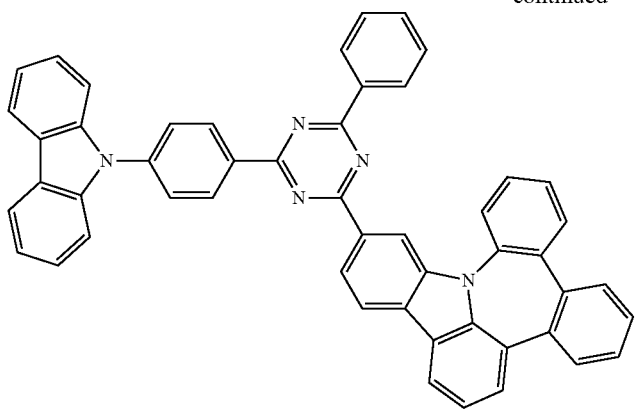
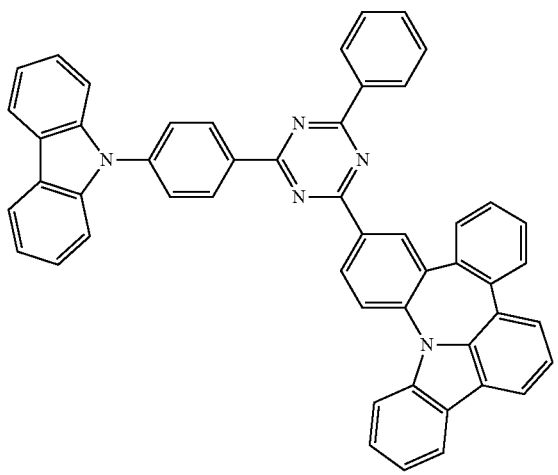
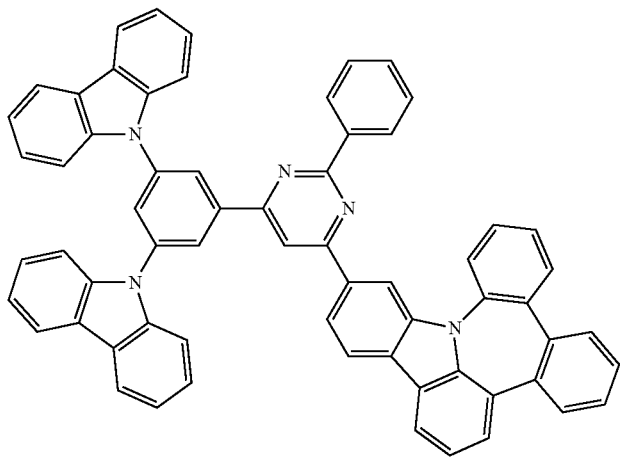

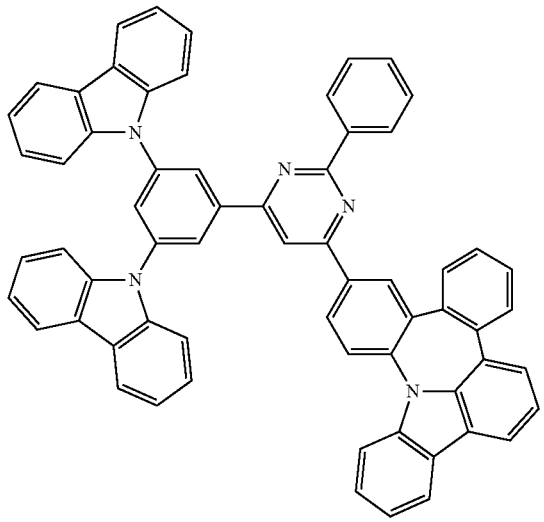
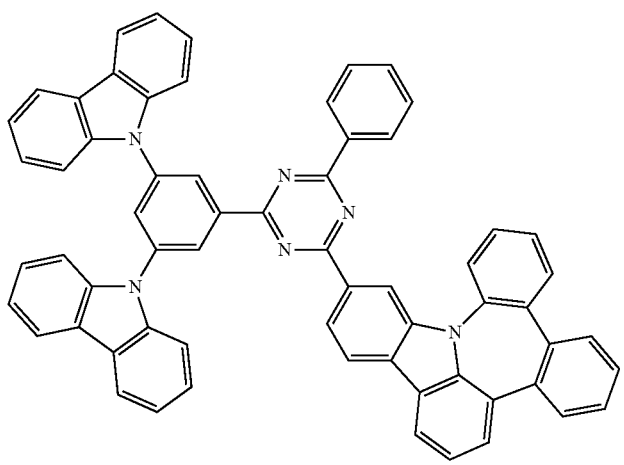
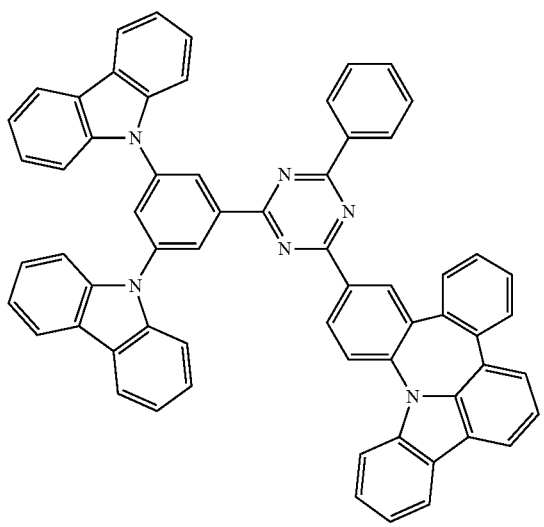

-continued
87
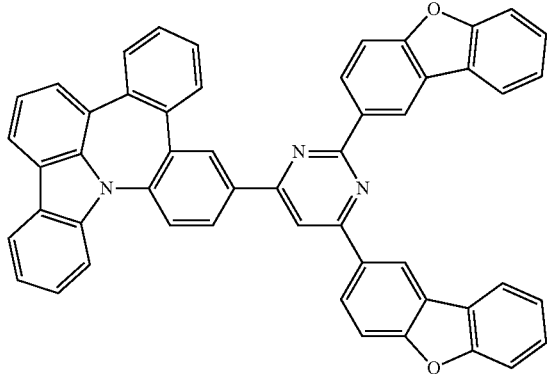
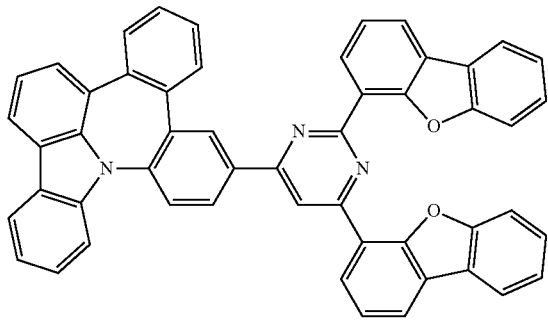
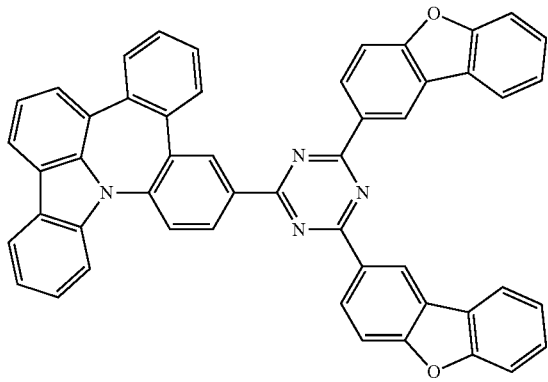
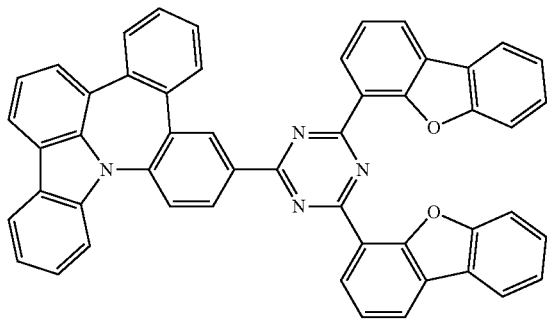
88
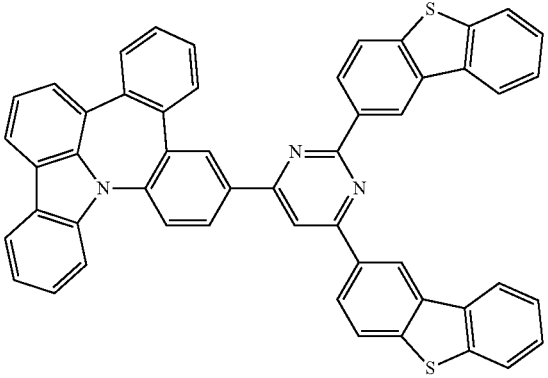
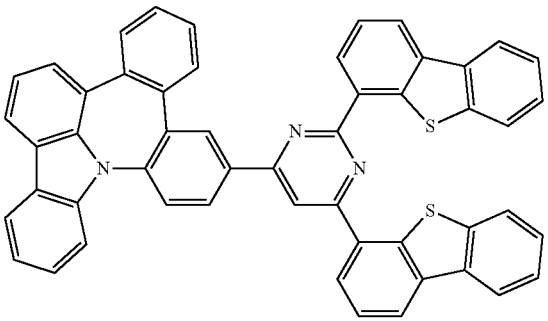
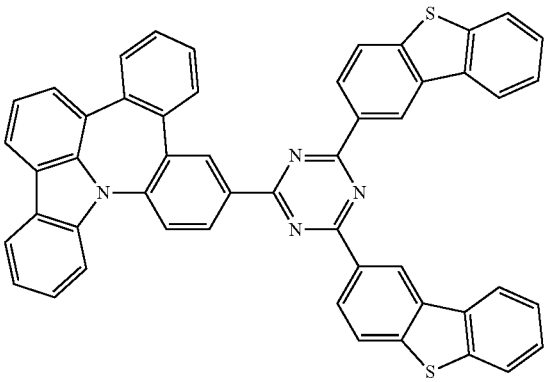
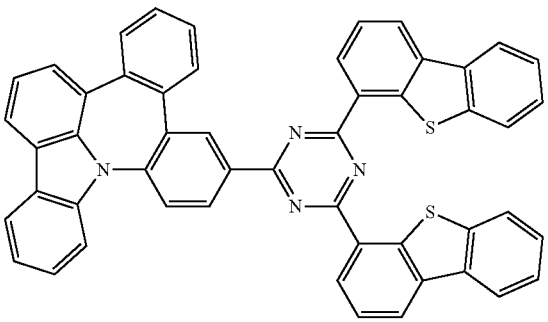

-continued
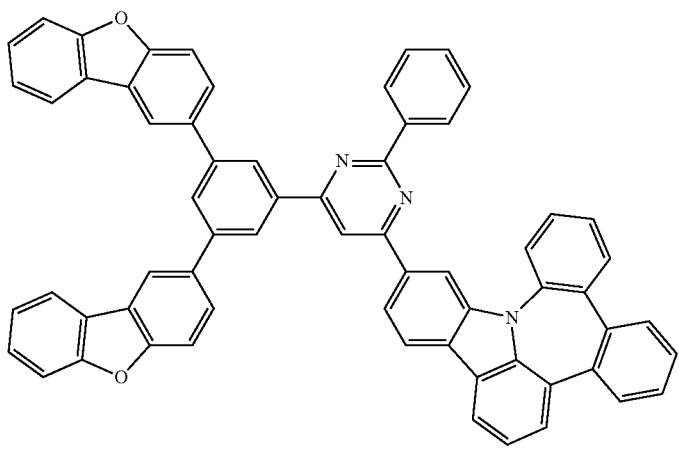
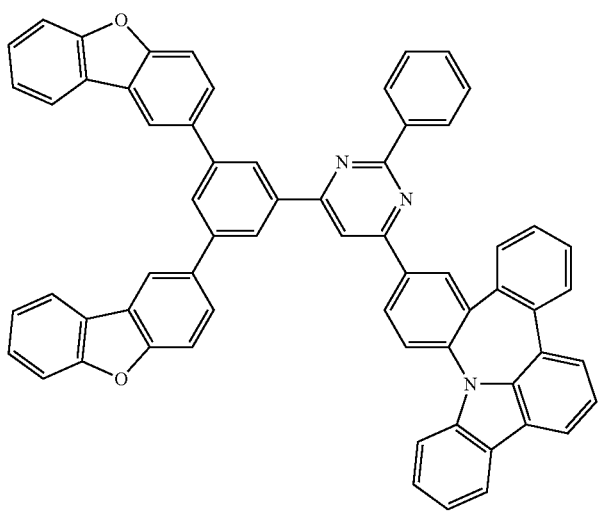
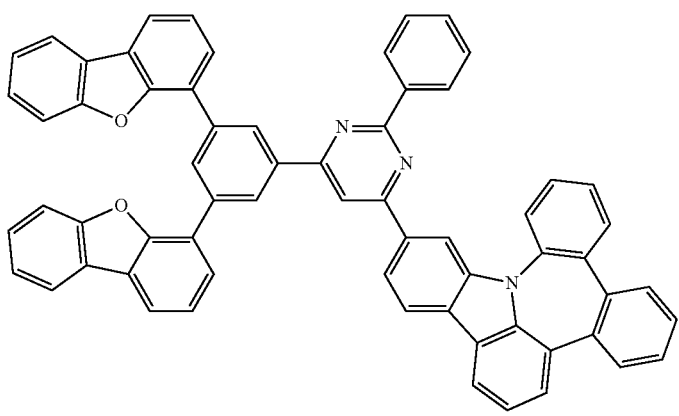

-continued
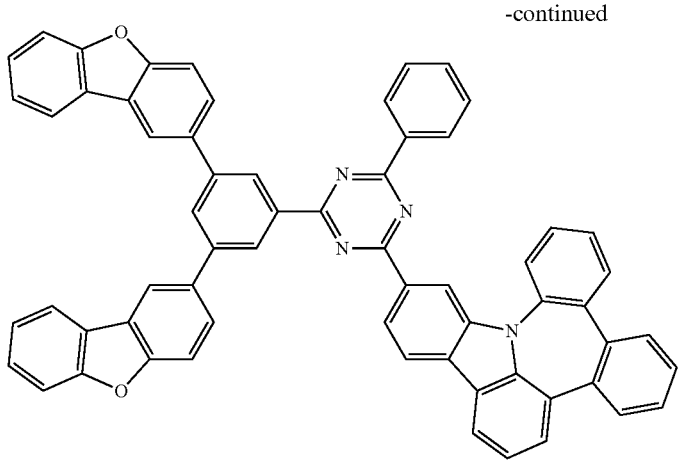
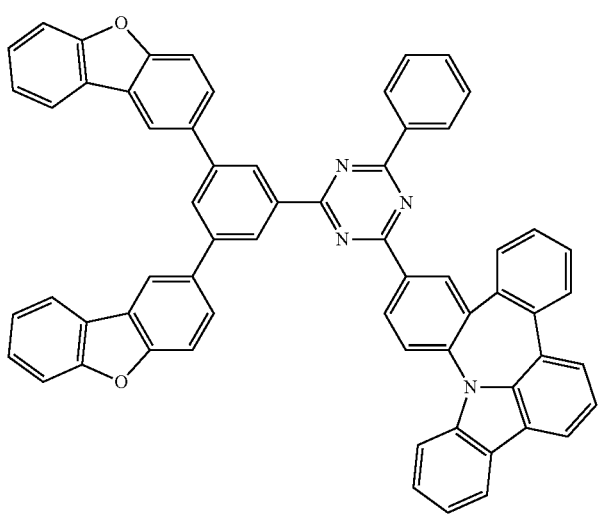
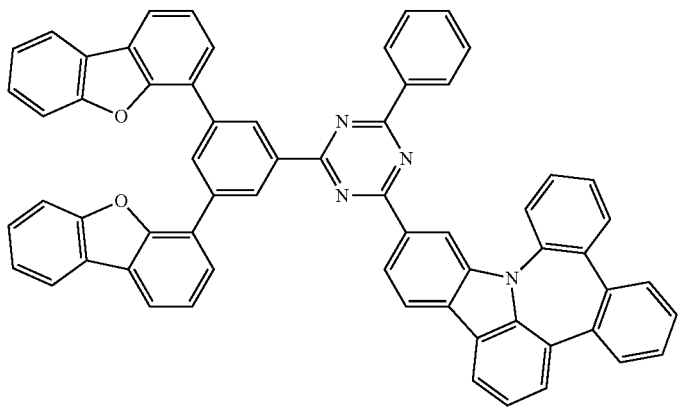

-continued
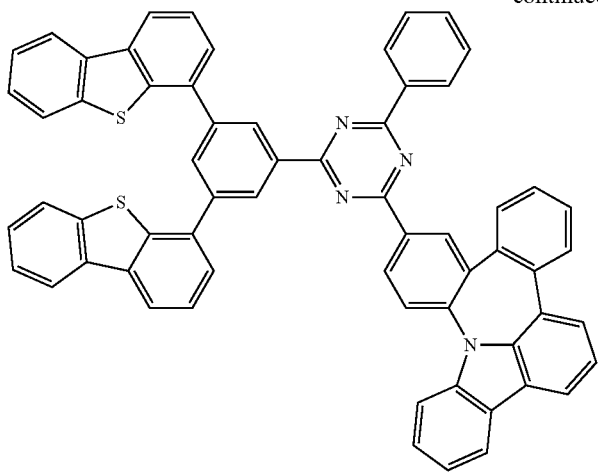
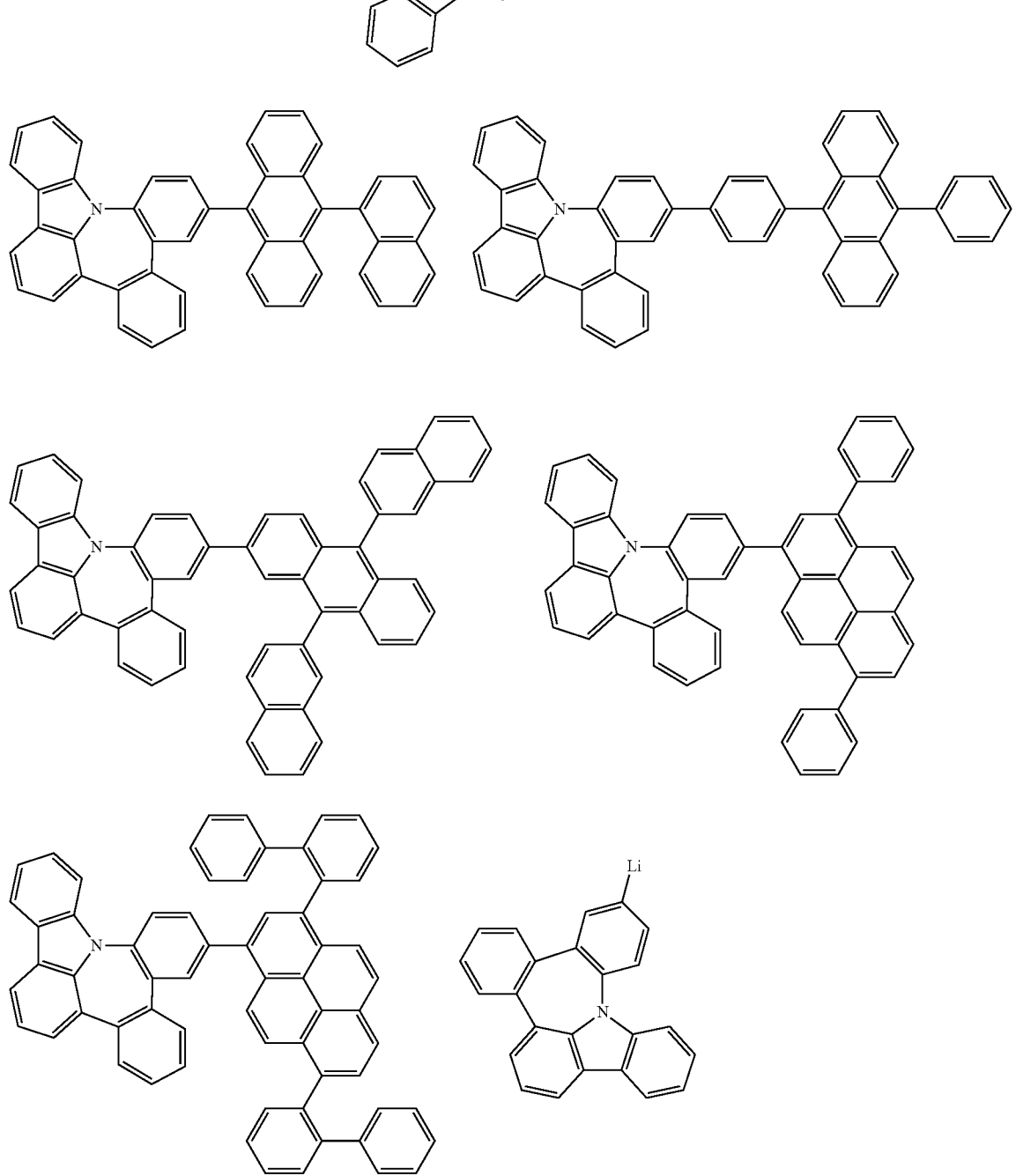

-continued
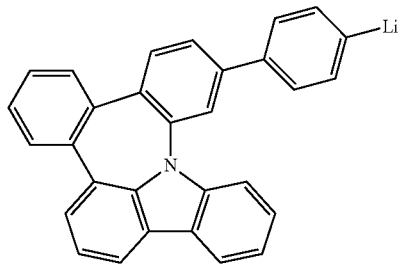
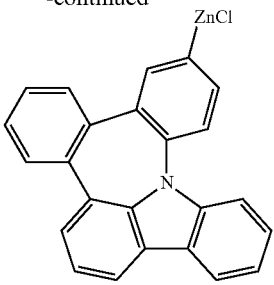
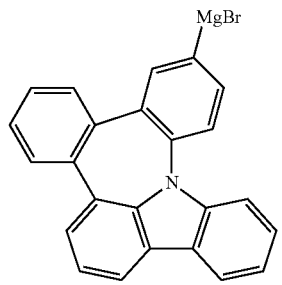
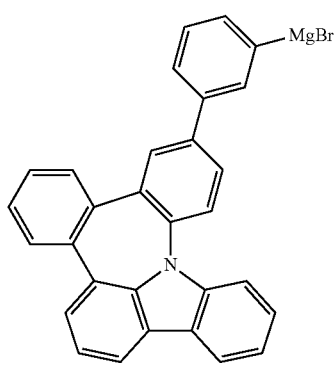
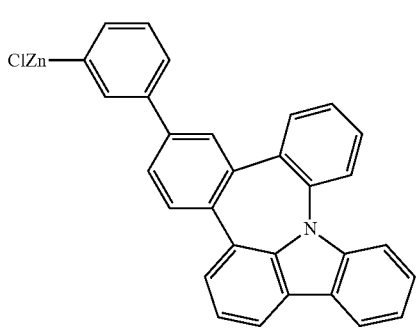
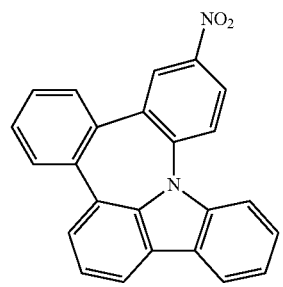
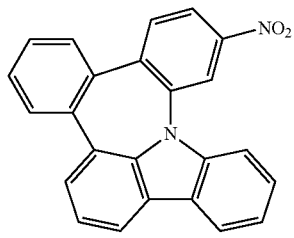
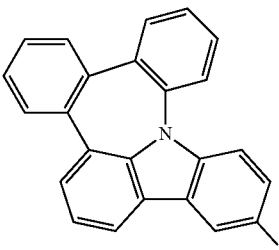
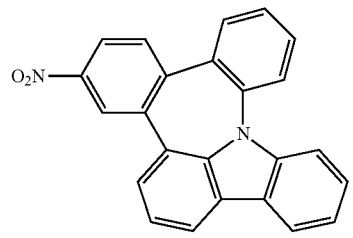
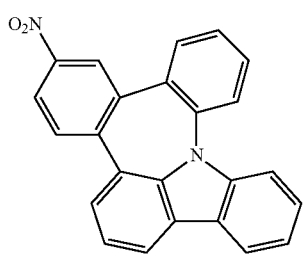
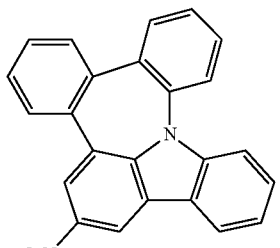
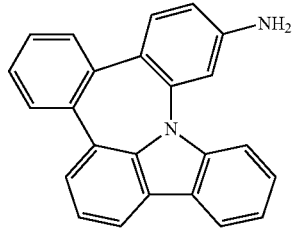
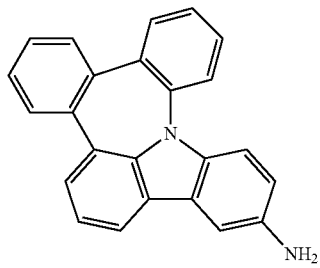
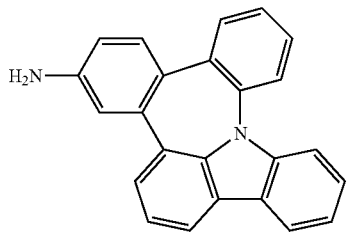
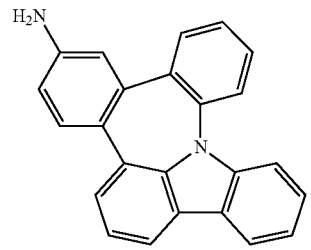

-continued
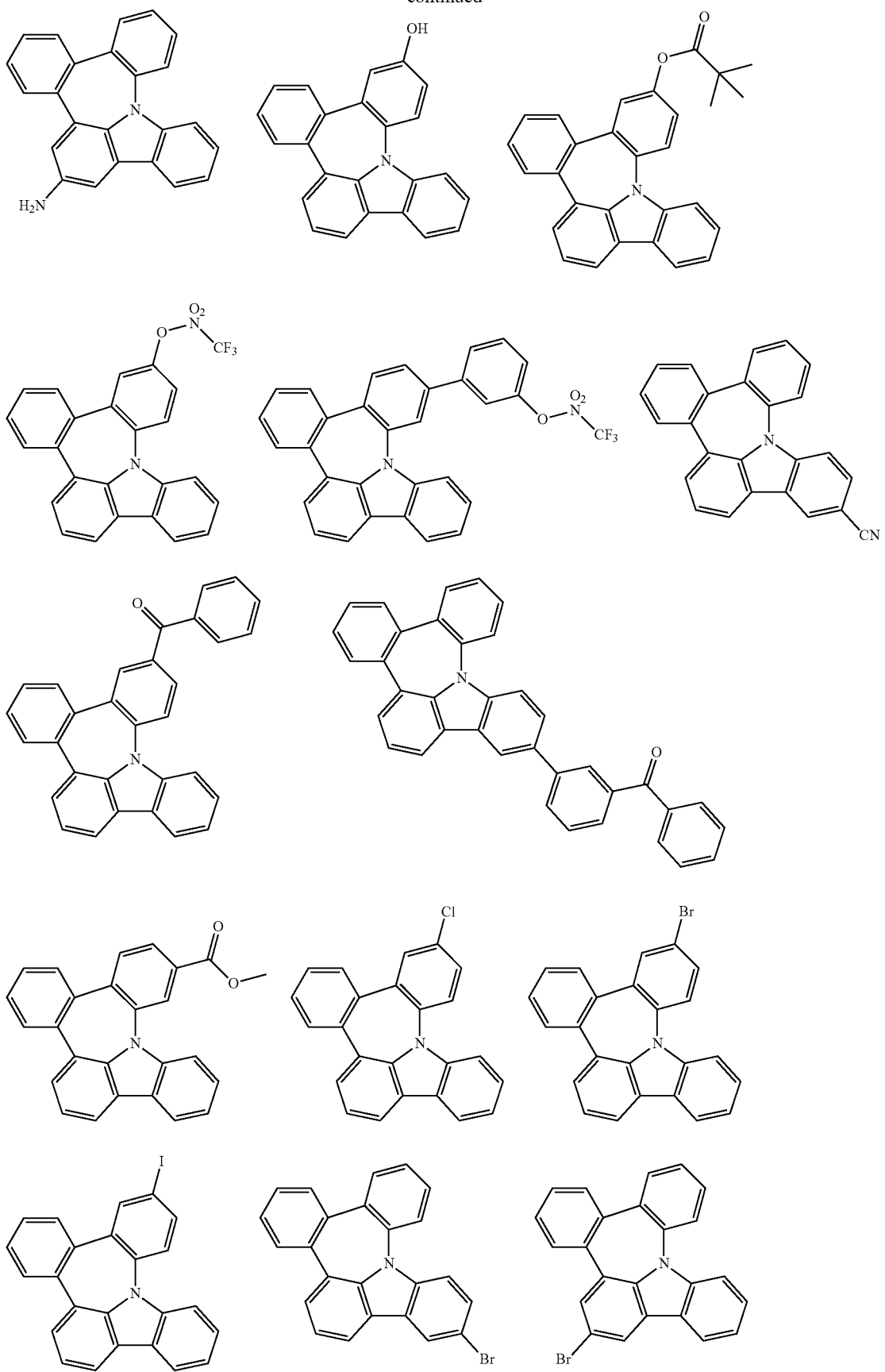

99      -continued      100
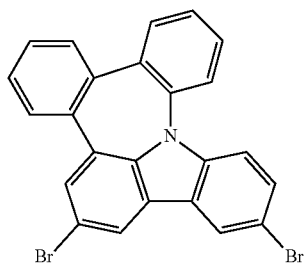 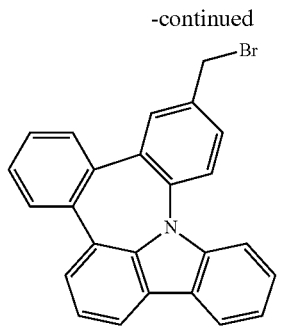 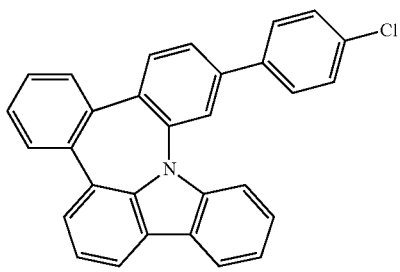
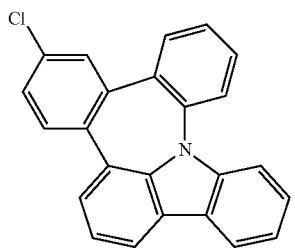 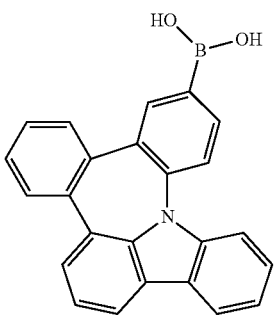 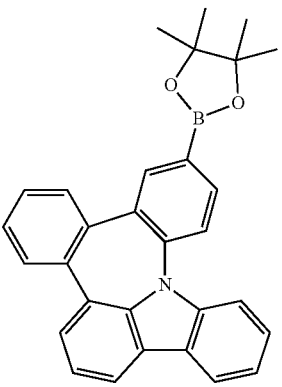
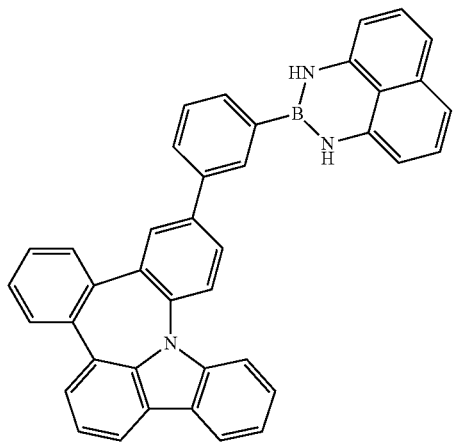 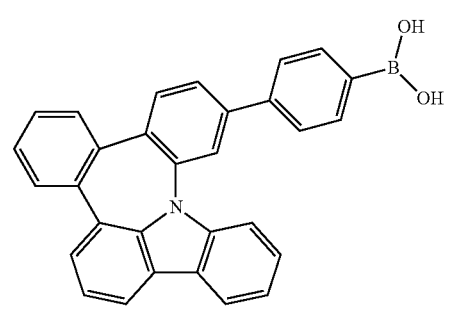
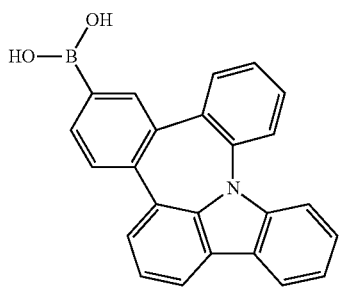 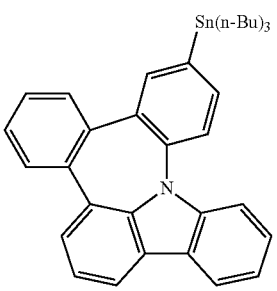 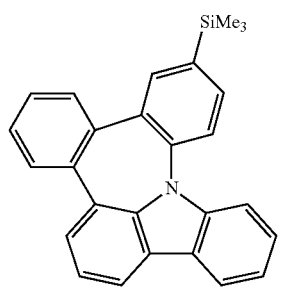

-continued
101
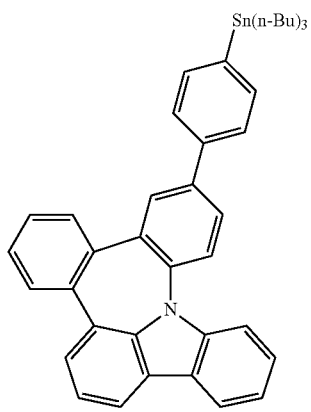
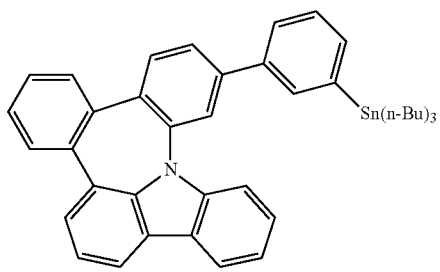
102
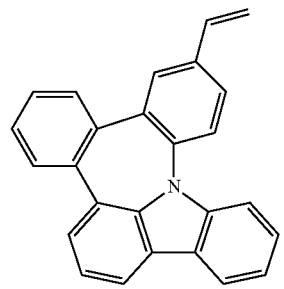
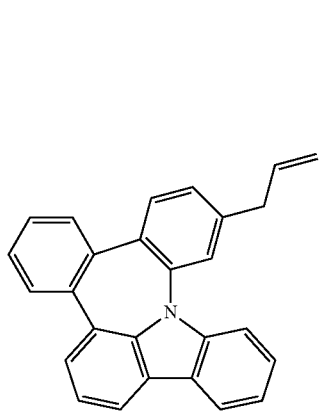
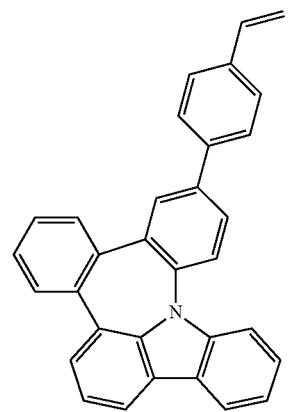
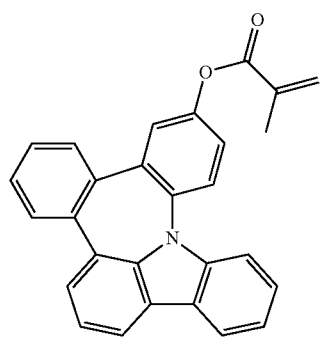
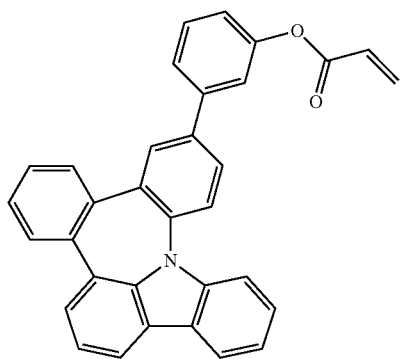
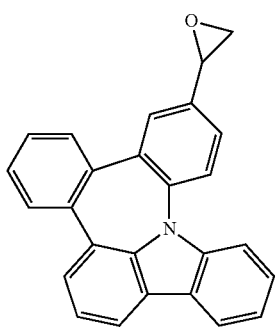
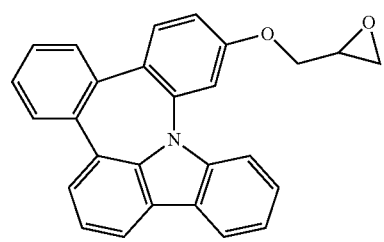
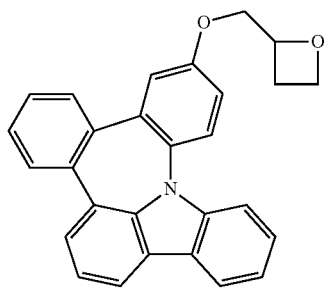
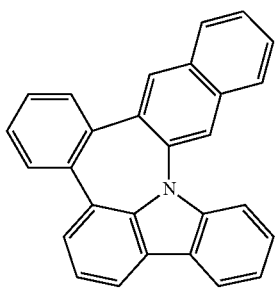
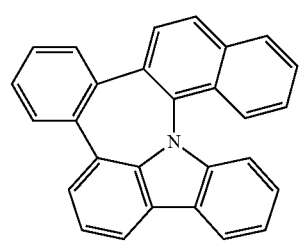

103
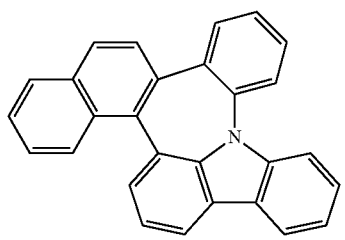
-continued
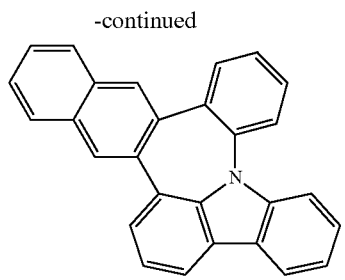
104
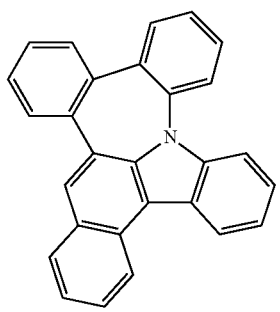
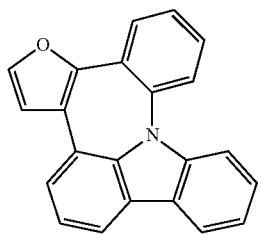
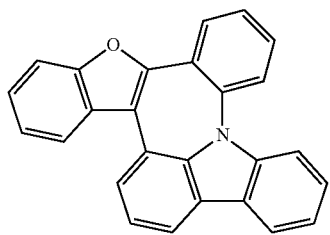
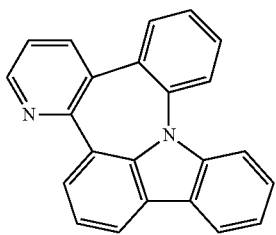
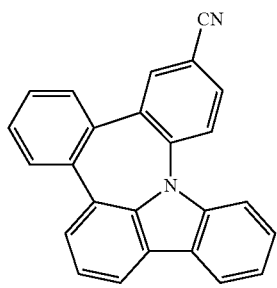
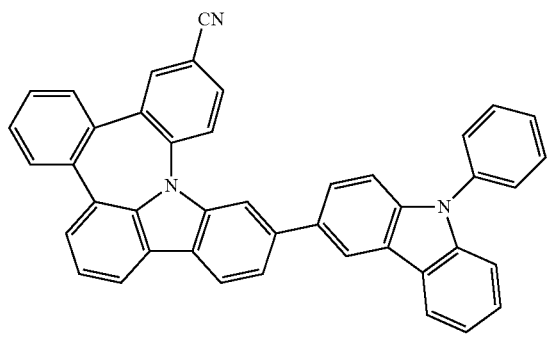
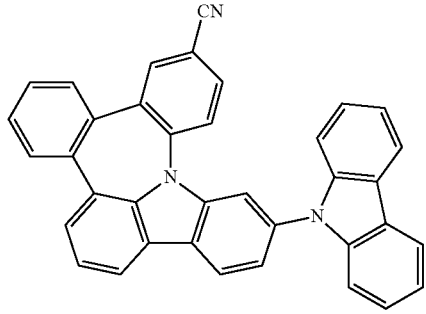
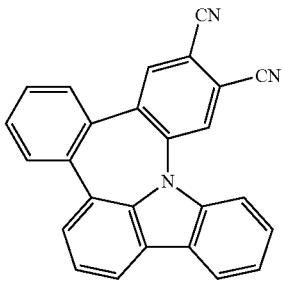
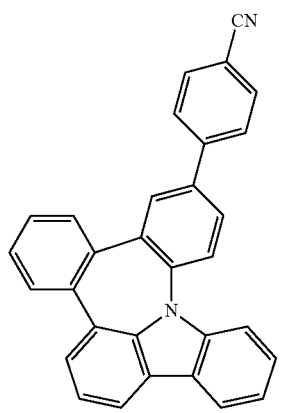

| 105 | 106 |
|---|---|
| 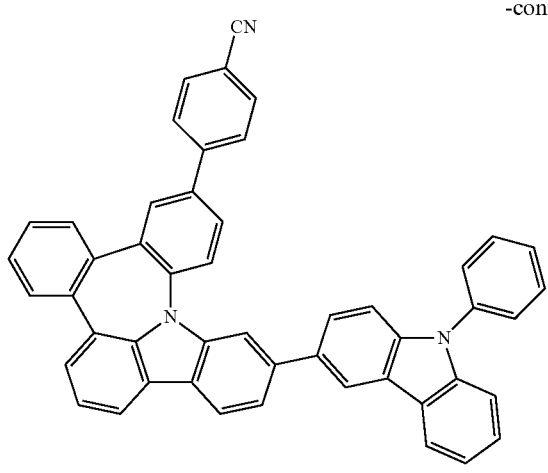 | 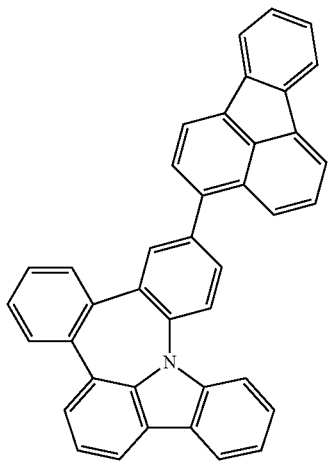 |
| 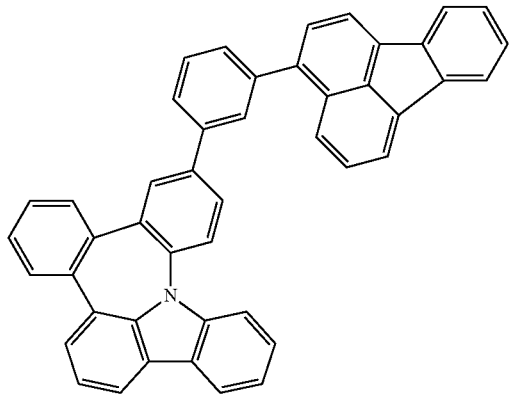 | 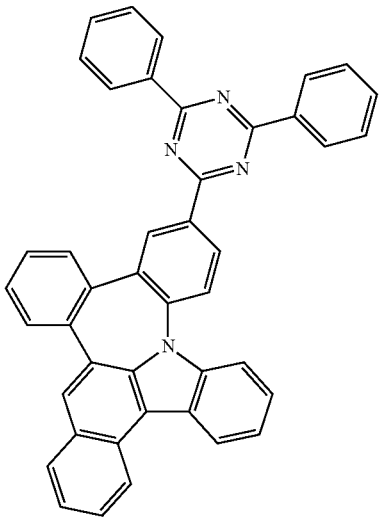 |
| 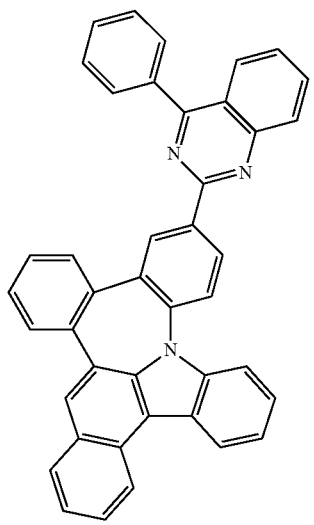 | 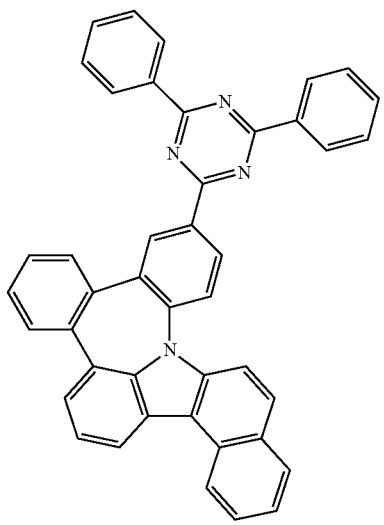 | 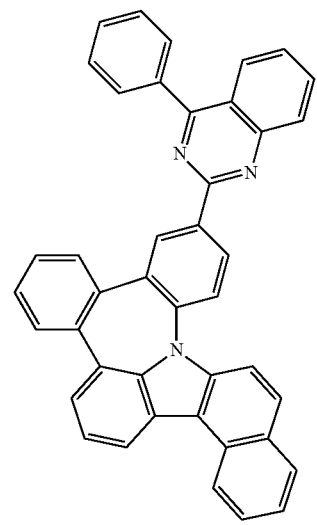 |

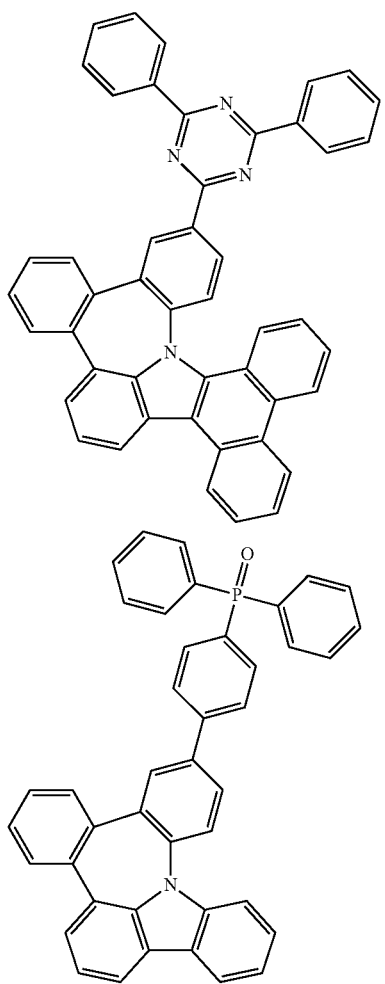

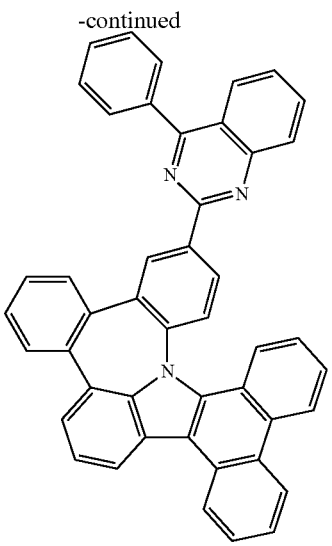

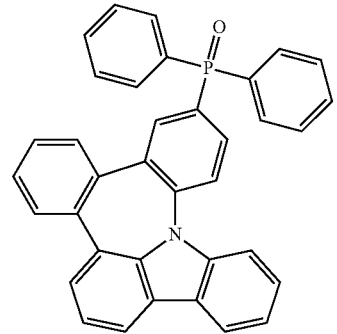

The nitrogen-containing heterocyclic compound A and the nitrogen-containing heterocyclic compound B are produced, for example, by the following synthesis route:

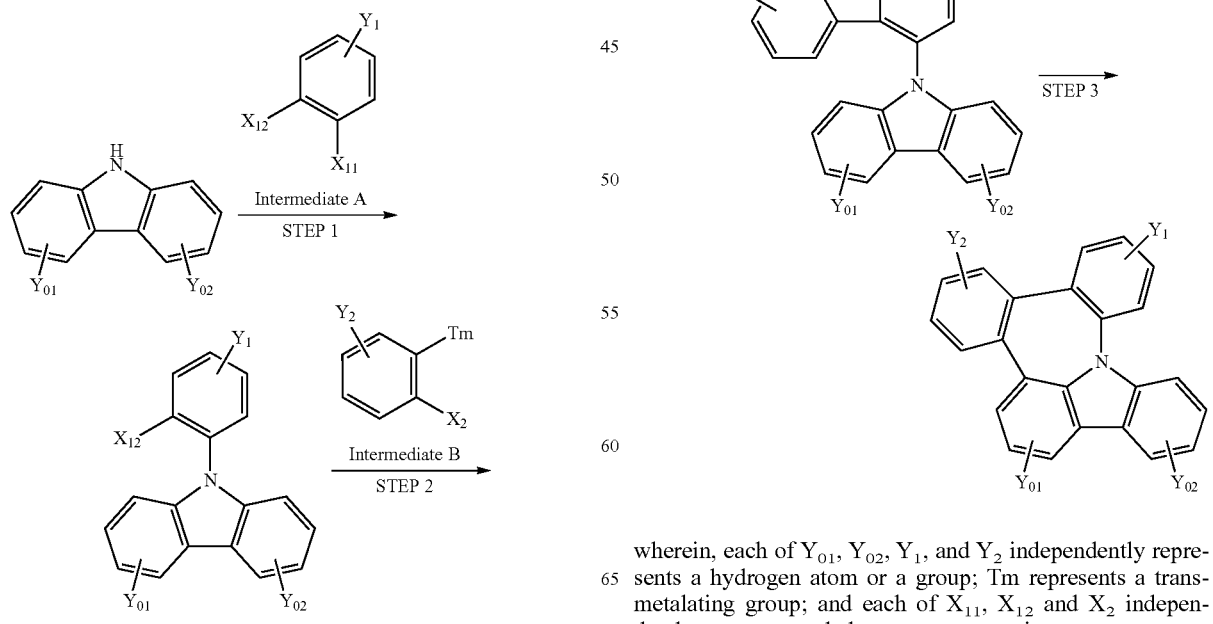

wherein, each of $Y_{01}$, $Y_{02}$, $Y_1$, and $Y_2$ independently represents a hydrogen atom or a group; Tm represents a transmetalating group; and each of $X_{11}$, $X_{12}$ and $X_2$ independently represents a halogen atom or a nitro group.

In STEP 1, a coupling reaction between a carbazole compound and the intermediate A wherein $X_{11}$ is a chlorine atom, a bromine atom or an iodine atom is carried out in the presence of cupper or palladium. Alternatively, a substitution reaction is carried out using a carbazole compound and the intermediate A wherein $X_{11}$ is a fluorine atom in the presence of a base.

If $X_{12}$ is a halogen atom, the obtained compound is used directly in STEP 2. If $X_{12}$ is a nitro group, the nitro group is converted to an amino group by a reduction reaction, and then, to a halogen atom by Sandmeyer reaction.

In STEP 2, the compound obtained in STEP 1 undergoes a coupling reaction. A compound having a transmetalating group (Tm) (intermediate B) can be used as the coupling partner. The coupling reaction is carried out typically by Suzuki-Miyaura reaction using a boronic acid.

If $X_2$ is a halogen atom, the obtained compound is used directly in STEP 3. If $X_2$ is a nitro group, the nitro group is converted to an amino group by a reduction reaction, and then, to a halogen atom by Sandmeyer reaction.

In STEP 3, the compound obtained in STEP 2 is converted to the material for organic EL device and the nitrogen-containing heterocyclic compound of the invention by an intramolecular Mizoroki-Heck reaction.

A compound wherein each of $Y_{01}$, $Y_{02}$, $Y_1$, and $Y_2$ is a group capable of participating in the oxidative addition of coupling reaction, such as a halogen atom, is useful as an intermediate, because a desired group can be introduced into desired position according to intended use. In addition, each of $Y_{01}$, $Y_{02}$, $Y_1$, and $Y_2$ can be converted to a group capable of participating in the transmetalation of coupling reaction, for example, a boronic acid group.

A compound wherein each of $Y_{01}$, $Y_{02}$, $Y_1$, and $Y_2$ is a group capable of participating in the transmetalation of coupling reaction, for example, a boronic acid group, is also useful. To obtain a compound to which a desired group is introduced into desired position according to intended use, the desired group may be introduced in advance as $Y_{01}$, $Y_{02}$, $Y_1$, and $Y_2$. In addition, a group which is convertible to a halogen atom, for example, a nitro group and an amino group, may be introduce.

Alternatively, the nitrogen-containing heterocyclic compound A and the nitrogen-containing heterocyclic compound B may be obtained by the following synthesis route:

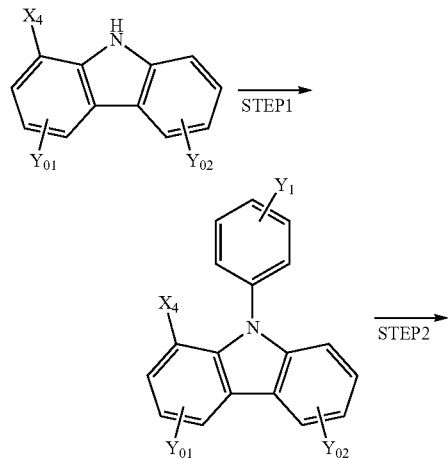

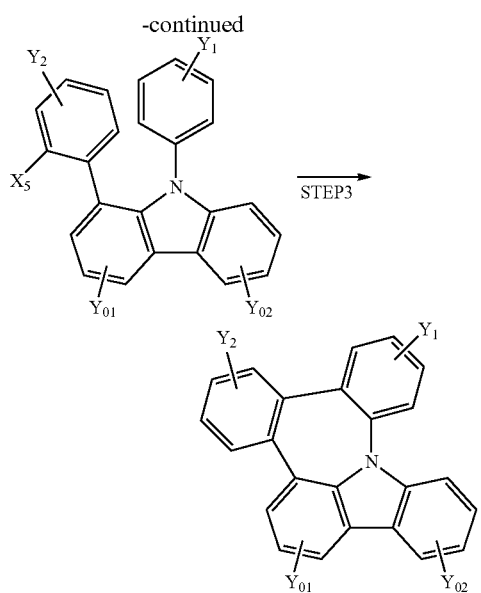

wherein each of $Y_{01}$, $Y_{02}$, $Y_1$, and $Y_2$ represents a hydrogen atom or a group and each of $X_4$ and $X_5$ represents a halogen atom.

In STEP 1, a coupling reaction of a 1-halocarbazole compound at the nitrogen atom is carried out. In STEP 2, the carbazole derivative is substituted at its position 1, for example, by Suzuki-Miyaura coupling reaction using a boronic acid compound. Finally, in STEP 3, the nitrogen-containing heterocyclic compound A and the nitrogen-containing heterocyclic compound B are obtained by an intramolecular Mizoroki-Heck reaction.

In the above, the synthesis of the compounds represented by formulae (3) and (3') is described as an example of the method of synthesizing the nitrogen-containing heterocyclic compound A and the nitrogen-containing heterocyclic compound B. Other nitrogen-containing heterocyclic compounds A and other nitrogen-containing heterocyclic compounds B can be synthesized by appropriately modifying the synthesizing methods mentioned above. For example, by changing the starting material from the carbazole compound used in the above synthesis route to an indole compound or using various heterocyclic compounds, etc. as the intermediate material in the coupling reactions in place of the aryl compounds, the nitrogen-containing heterocyclic compound having desired structure can be obtained.

Organic EL Device

The organic EL device of the invention will be described below.

The organic EL device comprises organic thin film layers (emission unit) between a cathode an anode. The organic thin film layers comprise a light emitting layer and at least one layer of the organic thin film layers comprises the material for organic EL device mentioned above.

Examples of the organic thin film layer comprising the material for organic EL device include an anode-side organic thin film layer formed between an anode and a light emitting layer (hole transporting layer, hole injecting layer, etc.), a light emitting layer, a cathode-side organic thin film layer formed between a cathode and a light emitting layer (electron transporting layer, electron injecting layer, etc.), a space layer, and a blocking layer, although not limited thereto. The material for organic EL device may be used in any of the above layers, for example, used in a light emitting layer of a fluorescent emitting unit as a host material or a dopant material, in a light emitting layer of a phosphorescent emitting unit as a host material, and in a hole transporting layer, an electron transporting layer, etc. of an emitting unit.

The organic EL device of the invention may be any of a single color emitting device of fluorescent or phosphorescent type, a white-emitting device of fluorescent-phosphorescent hybrid type, an emitting device of a simple type having a single emission unit, and an emitting device of a tandem type having two or more emission units, with the phosphorescent device being preferred. The "emission unit" referred to herein is the smallest unit for emitting light by the recombination of injected holes and injected electrons, which comprises one or more organic layers wherein at least one layer is a light emitting layer.

Representative device structures of the simple-type organic EL device are shown below.

(1) Anode/Emission Unit/Cathode

The emission unit may be a laminate comprising two or more layers selected from a phosphorescent light emitting layer and a fluorescent light emitting layer. A space layer may be disposed between the light emitting layers to prevent the diffusion of excitons generated in the phosphorescent light emitting layer into the fluorescent light emitting layer. Representative layered structures of the emission unit are shown below.

(a) hole transporting layer/light emitting layer (/electron transporting layer);
(b) hole transporting layer/first phosphorescent light emitting layer/second phosphorescent light emitting layer (/electron transporting layer);
(c) hole transporting layer/phosphorescent light emitting layer/space layer/fluorescent light emitting layer (/electron transporting layer);
(d) hole transporting layer/first phosphorescent light emitting layer/second phosphorescent light emitting layer/space layer/fluorescent light emitting layer (/electron transporting layer);
(e) hole transporting layer/first phosphorescent light emitting layer/space layer/second phosphorescent light emitting layer/space layer/fluorescent light emitting layer (/electron transporting layer);
(f) hole transporting layer/phosphorescent light emitting layer/space layer/first fluorescent light emitting layer/second fluorescent light emitting layer (/electron transporting layer);
(g) hole transporting layer/electron blocking layer/light emitting layer (/electron transporting layer);
(h) hole transporting layer/light emitting layer/hole blocking layer (/electron transporting layer); and
(i) hole transporting layer/fluorescent light emitting layer/triplet blocking layer (/electron transporting layer).

The emission color of the phosphorescent light emitting layer and that of the fluorescent light emitting layer may be different. For example, the layered structure of the laminated light emitting layer (d) may be hole transporting layer/first phosphorescent light emitting layer (red emission)/second phosphorescent light emitting layer (green emission)/space layer/fluorescent light emitting layer (blue emission)/electron transporting layer.

An electron blocking layer may be disposed between the light emitting layer and the hole transporting layer or between the light emitting layer and the space layer, if necessary. Also, a hole blocking layer may be disposed between the light emitting layer and the electron transporting layer, if necessary. With such a electron blocking layer or a hole blocking layer, electrons and holes are confined in the light emitting layer to increase the degree of charge recombination in the light emitting layer, thereby improving the lifetime.

Representative device structure of the tandem-type organic EL device is shown below.

(2) Anode/First Emission Unit/Intermediate Layer/Second Emission Unit/Cathode

The layered structure of the first emission unit and the second emission unit may be selected from those described above with respect to the emission unit.

Generally, the intermediate layer is also called an intermediate electrode, an intermediate conductive layer, a charge generation layer, an electron withdrawing layer, a connecting layer, or an intermediate insulating layer. The intermediate layer may be formed by known materials so as to supply electrons to the first emission unit and holes to the second emission unit.

A schematic structure of an example of the organic EL device of the invention is shown in FIG. 1 wherein the organic EL device 1 comprises a substrate 2, an anode 3, a cathode 4, and an emission unit (organic thin film layer) 10 disposed between the anode 3 and the cathode 4. The emission unit 10 comprises a light emitting layer 5 which comprises at least one phosphorescent emitting layer containing a phosphorescent host material and a phosphorescent dopant material (phosphorescent emitting material). A hole injecting/transporting layer (anode-side organic thin film layer) 6, etc. may be disposed between the light emitting layer 5 and the anode 3, and an electron injecting/transporting layer (cathode-side organic thin film layer) 7, etc. may be disposed between the light emitting layer 5 and the cathode 4. An electron blocking layer may be disposed on the anode 3 side of the light emitting layer 5, and a hole blocking layer may be disposed on the cathode 4 side of the light emitting layer 5. With these blocking layers, electrons and holes are confined in the light emitting layer 5 to increase the degree of exciton generation in the light emitting layer 5.

In the present invention, a host is referred to as a fluorescent host when combinedly used with a fluorescent dopant (fluorescent emitting material) and as a phosphorescent host when combinedly used with a phosphorescent dopant. Therefore, the fluorescent host and the phosphorescent host are not distinguished from each other merely by the difference in their molecular structures. Namely, in the present invention, the term "phosphorescent host" means a material for constituting a phosphorescent emitting layer containing a phosphorescent dopant and does not mean a material that cannot be utilized as a material for a fluorescent emitting layer. The same applies to the fluorescent host.

Substrate

The organic EL device of the invention is formed on a light-transmissive substrate. The light-transmissive substrate serves as a support for the organic EL device and preferably a flat substrate having a transmittance of 50% or more to 400 to 700 nm visible light. Examples of the substrate include a glass plate and a polymer plate. The glass plate may include a plate made of soda-lime glass, barium-strontium-containing glass, lead glass, aluminosilicate glass, borosilicate glass, barium borosilicate glass, or quartz. The polymer plate may include a plate made of polycarbonate, acryl, polyethylene terephthalate, polyether sulfide, or polysulfone.

Anode

The anode of the organic EL device injects holes to the hole transporting layer or the light emitting layer, and an anode having a work function of 4.5 eV or more is effective.

Examples of the material for anode include indium tin oxide alloy (ITO), tin oxide (NESA), indium zinc oxide alloy, gold, silver, platinum, and cupper. The anode is formed by making the electrode material into a thin film by a method, such as a vapor deposition method or a sputtering method. When getting the light emitted from the light emitting layer through the anode, the transmittance of anode to visible light is preferably 10% or more. The sheet resistance of anode is preferably several hundreds Ω/□ or less. The film thickness of anode depends upon the kind of material and generally 10 nm to 1 µm, preferably 10 to 200 nm.

Cathode

The cathode injects electrons to the electron injecting layer, the electron transporting layer or the light emitting layer, and formed preferably by a material having a small work function. Examples of the material for cathode include, but not limited to, indium, aluminum, magnesium, magnesium-indium alloy, magnesium-aluminum alloy, aluminum-lithium alloy, aluminum-scandium-lithium alloy, and magnesium-silver alloy. Like the anode, the cathode is formed by making the material into a thin film by a method, such as the vapor deposition method and the sputtering method. The emitted light may be taken through the cathode, if necessary.

Light Emitting Layer

The light emitting layer is an organic layer having a light emitting function and contains a host material and a dopant material when a doping system is employed. The major function of the host material is to promote the recombination of electrons and holes and confine excitons in the light emitting layer. The dopant material causes the excitons generated by recombination to emit light efficiently.

In case of a phosphorescent device, the major function of the host material is to confine the excitons generated on the dopant in the light emitting layer.

To control the carrier balance in the light emitting layer, the light emitting layer may be made into a double host (host/co-host) layer, for example, by combinedly using an electron transporting host and a hole transporting host.

The light emitting layer may be made into a double dopant layer, in which two or more kinds of dopant materials having high quantum yield are combinedly used and each dopant material emits light with its own color. For example, to obtain a yellow emission, a light emitting layer formed by co-depositing a host, a red-emitting dopant and a green-emitting dopant is used.

In a laminate of two or more light emitting layers, electrons and holes are accumulated in the interface between the light emitting layers, and therefore, the recombination region is localized in the interface between the light emitting layers, to improve the quantum efficiency.

The easiness of hole injection to the light emitting layer and the easiness of electron injection to the light emitting layer may be different from each other. Also, the hole transporting ability and the electron transporting ability each being expressed by mobility of holes and electrons in the light emitting layer may be different from each other.

The light emitting layer is formed, for example, by a known method, such as a vapor deposition method, a spin coating method, and LB method. The light emitting layer can be formed also by making a solution of a binder, such as resin, and the material for the light emitting layer in a solvent into a thin film by a method such as spin coating.

The light emitting layer is preferably a molecular deposit film. The molecular deposit film is a thin film formed by depositing a vaporized material or a film formed by solidifying a material in the state of solution or liquid. The molecular deposit film can be distinguished from a thin film formed by LB method (molecular build-up film) by the differences in the assembly structures and higher order structures and the functional difference due to the structural differences.

The phosphorescent dopant (phosphorescent emitting material) used in the light emitting layer is a compound which emits light by releasing the energy of excited triplet state and preferably a organometallic complex comprising at least one metal selected from Ir, Pt, Os, Au, Cu, Re, and Ru and a ligand, although not particularly limited thereto as long as emitting light by releasing the energy of excited triplet state. The ligand is preferably ortho-metallated. In view of obtaining a high phosphorescent quantum yield and further improving the external quantum efficiency of luminescent device, a metal complex comprising a metal selected from Ir, Os, and Pt is preferred, with a metal complex, particularly an ortho-metallated complex, such as an iridium complex, an osmium complex, and a platinum complex, being more preferred, an iridium complex and a platinum complex being still more preferred, and an ortho-metallated iridium complex being particularly preferred.

The content of the phosphorescent dopant in the light emitting layer is not particularly limited and selected according to the use of the device, and preferably 0.1 to 70% by mass, and more preferably 1 to 30% by mass. If being 0.1% by mass or more, the amount of light emission is sufficient. If being 70% by mass or less, the concentration quenching can be avoided.

Preferred examples of the organometallic complex for the phosphorescent dopant are shown below.

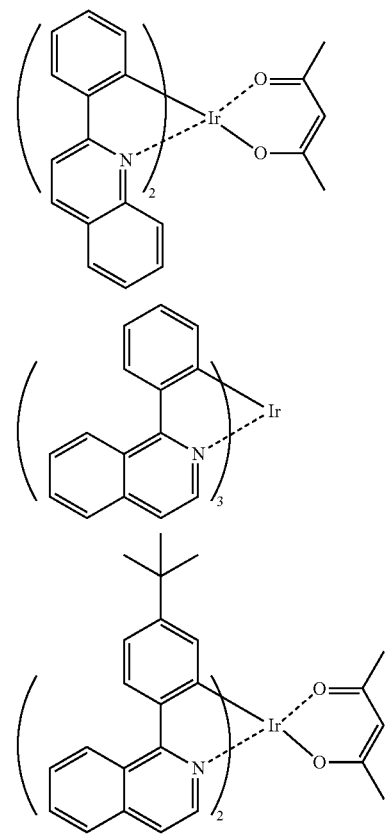

115
-continued
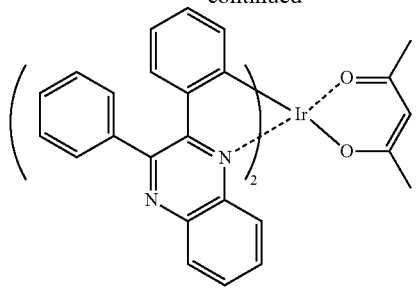
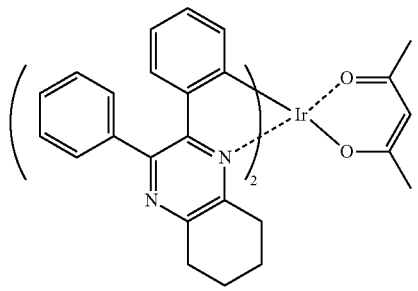
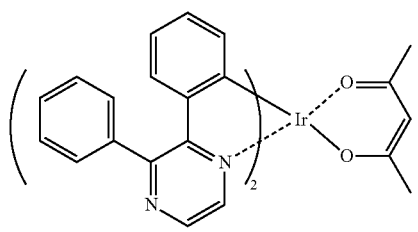
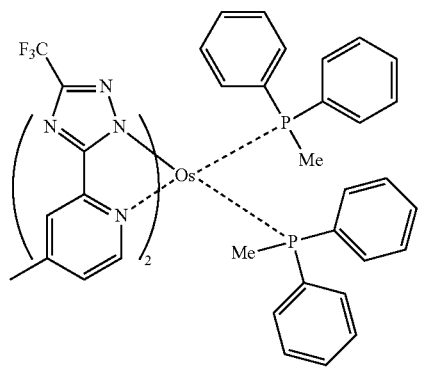
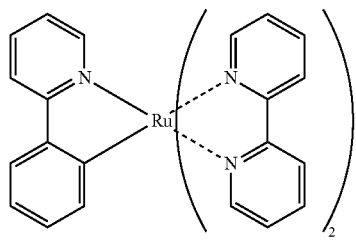
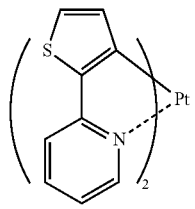
116
-continued
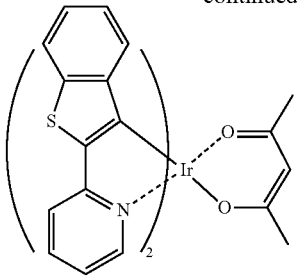
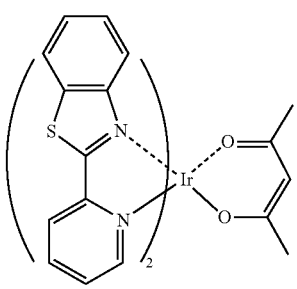
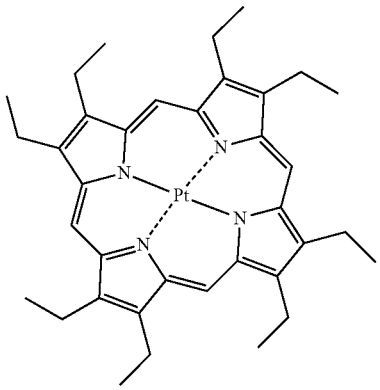
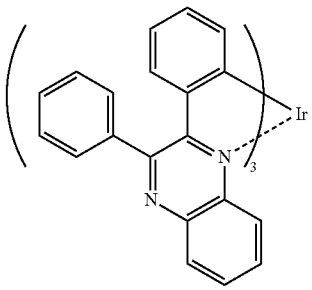
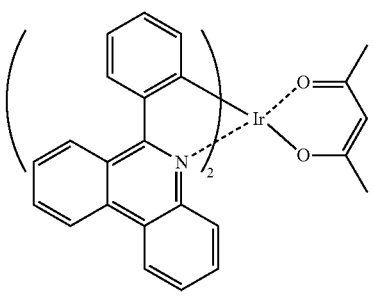

117
-continued
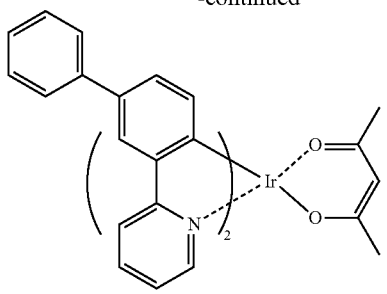
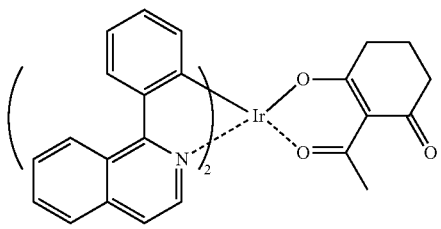
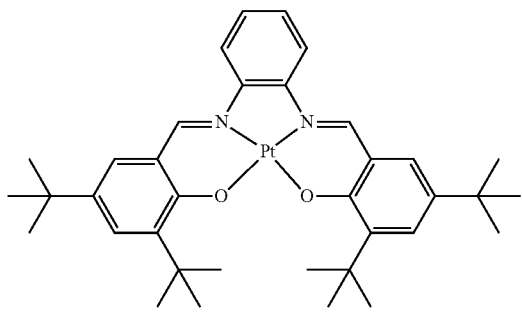
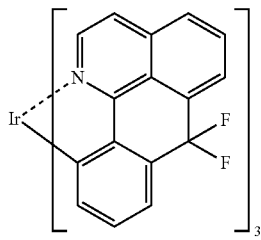
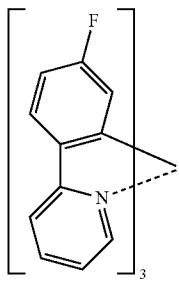
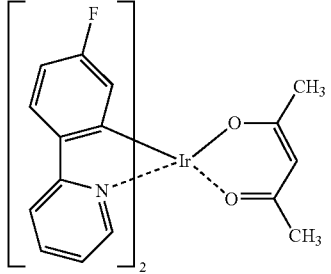
118
-continued
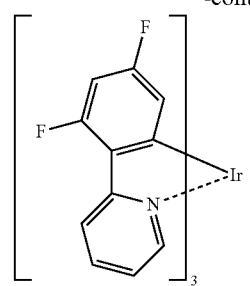
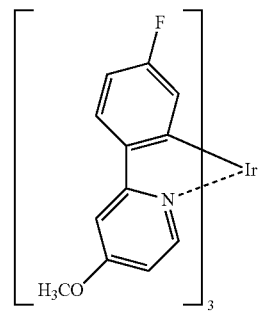
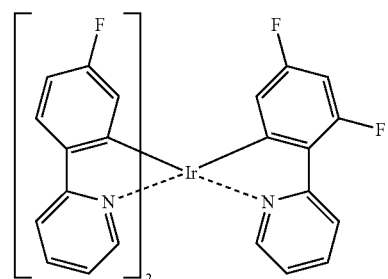
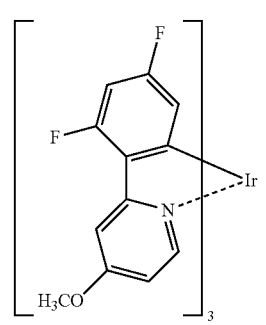
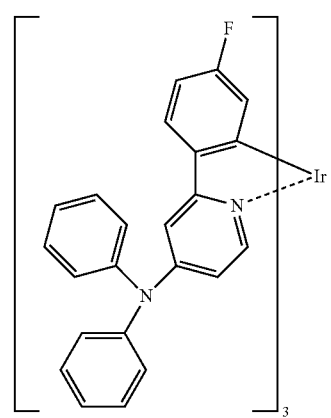

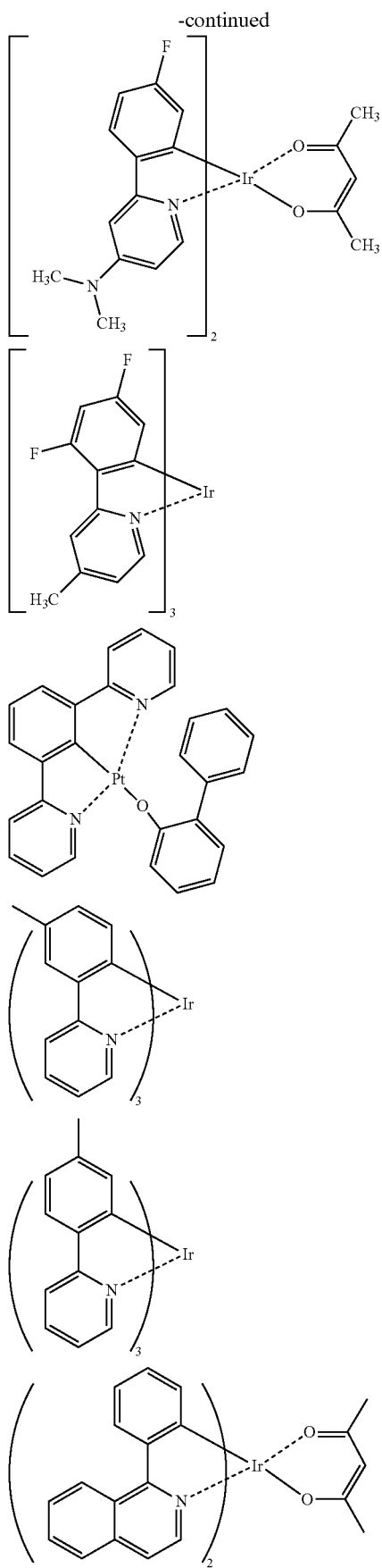
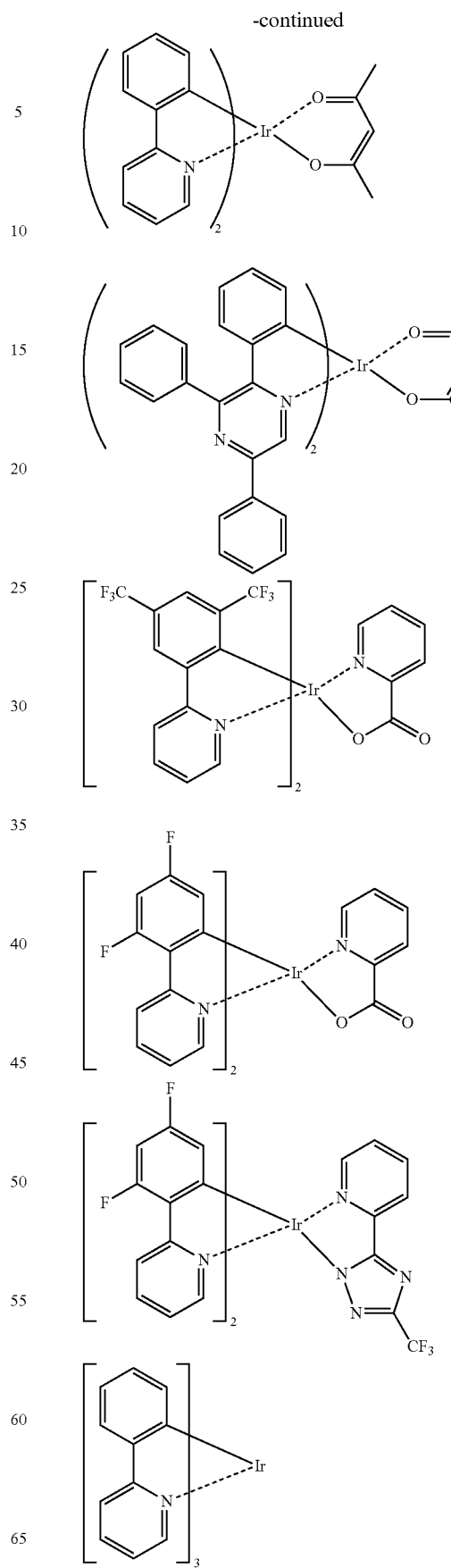

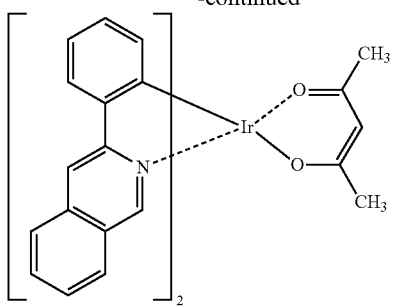
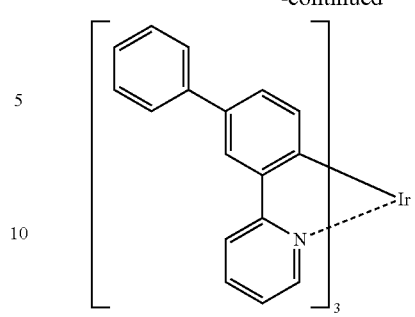
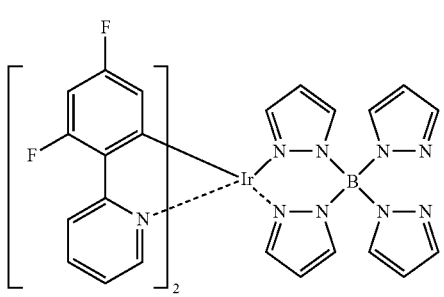
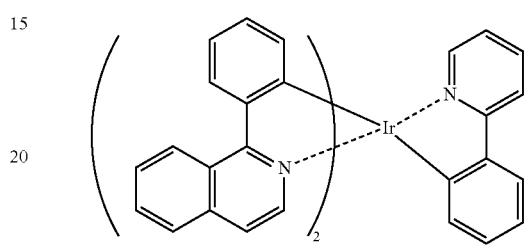
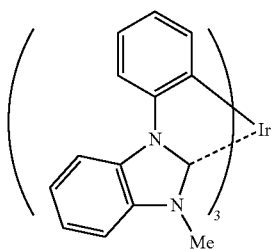
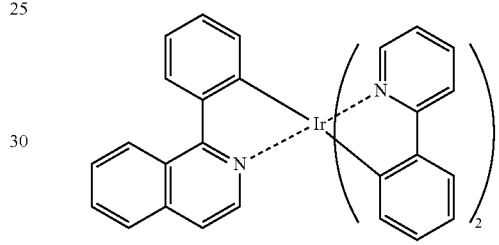
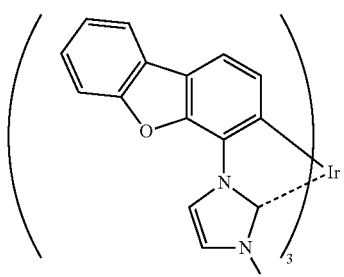
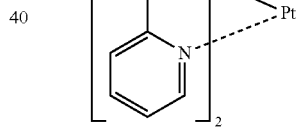
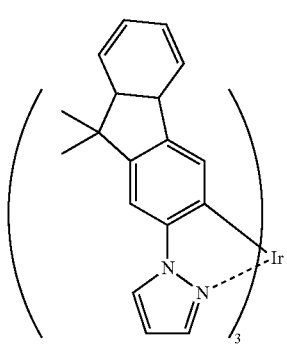
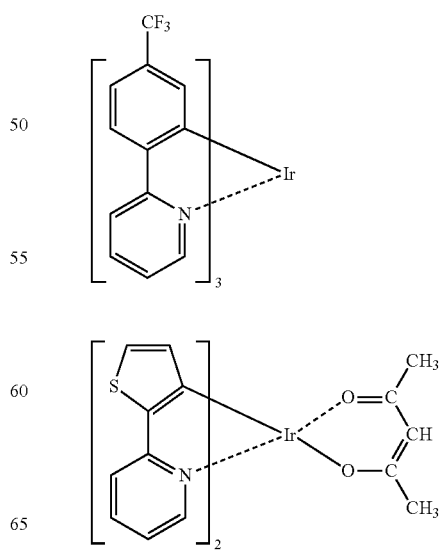

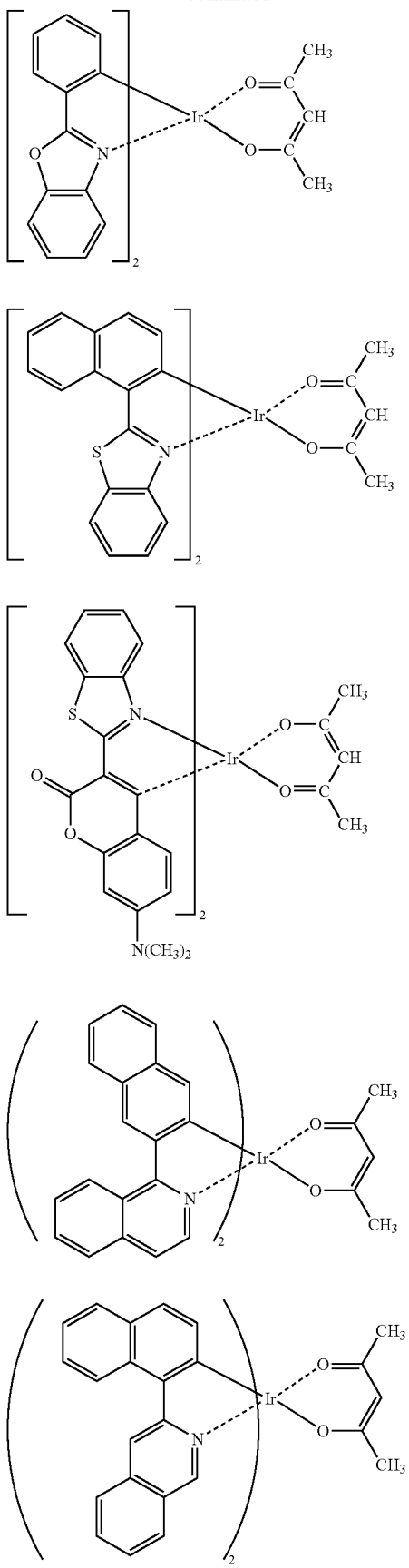
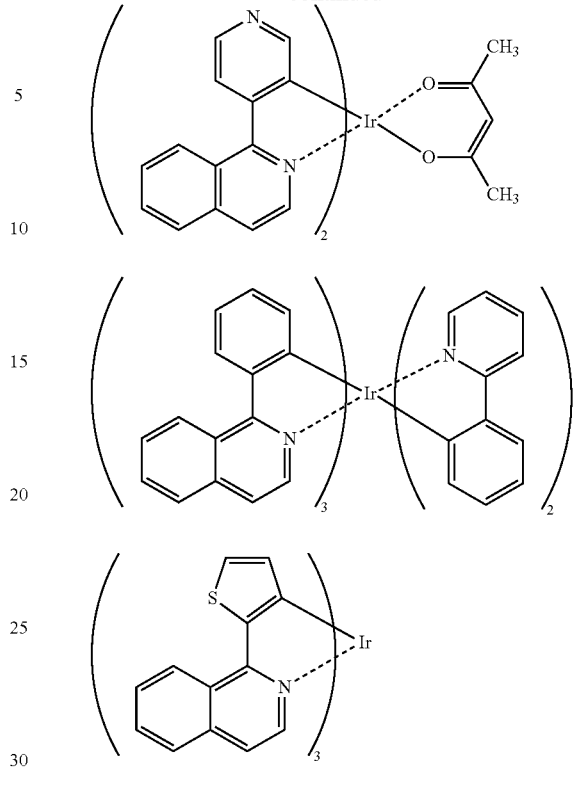

The phosphorescent host is a compound which confines the triplet energy of the phosphorescent dopant efficiently in the light emitting layer to cause the phosphorescent dopant to emit light efficiently. Although the material for organic EL device of the invention is useful as a phosphorescent host, a compound other than the material for organic EL device of the invention may be used as the phosphorescent host according to the use of the device.

The material for organic EL device of the invention and the compound other than it may be combinedly used in the same light emitting layer as the phosphorescent host material. If two or more light emitting layers are formed, the material for organic EL device of the invention can be used in one of the light emitting layers as the phosphorescent host material and a compound other than the material for organic EL device of the invention can be used in another light emitting layer as the phosphorescent host material. The material for organic EL device of the invention may be used in an organic layer other than the light emitting layer. In this case, a compound other than the material for organic EL device of the invention may be used as a phosphorescent host of the light emitting layer.

Examples of the preferred phosphorescent host other than the material for organic EL device of the invention include a carbazole derivative, a triazole derivative, a oxazole derivative, an oxadiazole derivative, an imidazole derivative, a polyarylalkane derivative, a pyrazoline derivative, a pyrazolone derivative, a phenylenediamine derivative, an arylamine derivative, an amino-substituted chalcone derivative, a styrylanthracene derivative, a fluorenone derivative, a hydrazone derivative, a stilbene derivative, a silazane derivative, an aromatic tertiary amine compound, a styrylamine compound, an aromatic methylidene compound, a porphyrin compound, an anthraquinodimethane derivative, an anthrone derivative, a diphenylquinone derivative, a thiopyran dioxide derivative, a carbodiimide derivative, a fluorenylidenemethane derivative, a distyrylpyrazine derivative, a tetracarboxylic anhydride of fused ring such as naphthalene and perylene, a phthalocyanine derivative, a metal complex of 8-quinolinol derivative, metal phthalocyanine, metal complexes having a ligand such as benzoxazole and benzothiazole, an electroconductive oligomer, such as a polysilane compound, a poly(N-vinylcarbazole) derivative, an aniline copolymer, thiophene oligomer, and a polythiophene, and a polymer such as a polythiophene derivative, a polyphenylene derivative, a polyphenylenevinylene derivative, and a polyfluorene derivative. These phosphorescent hosts may be used alone or in combination of two or more. Examples thereof are shown below.

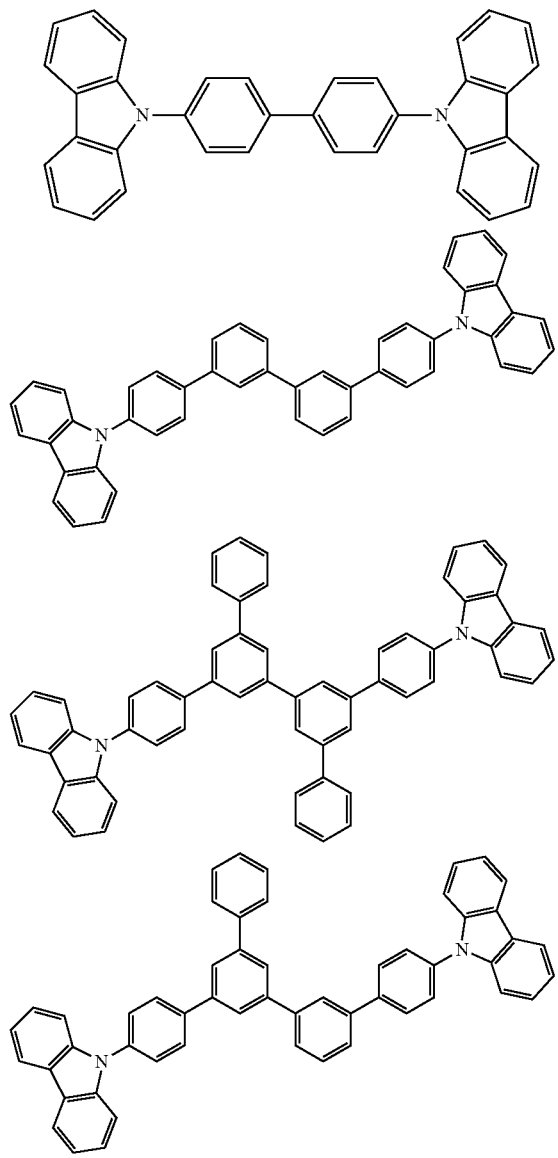

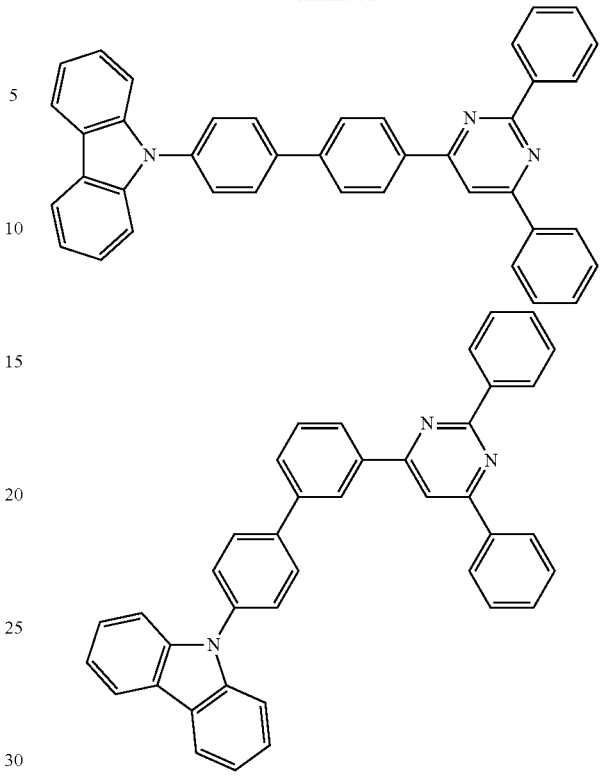

The organic EL device of the invention may comprise a light emitting layer comprising a fluorescent material, i.e., a fluorescent emitting layer. The fluorescent emitting layer may be formed from a known fluorescent material, for example, at least one material selected from an anthracene derivative, a fluoranthene derivative, a styrylamine derivative, and an arylamine derivative, with the anthracene derivative and the arylamine derivative being more preferred. In particular, the anthracene derivative is preferably used as the host material and the arylamine derivative is preferably used as the dopant. The materials described in WO 2010/134350 and WO 2010/134352 are preferably used. The material for organic EL device of the invention may be used in a fluorescent emitting layer as a fluorescent emitting material or a host material.

The anthracene derivative for use as a fluorescent material has preferably 26 to 100, more preferably 26 to 80, and still more preferably 26 to 60 ring carbon atoms. The anthracene derivative is preferably represented by formula (10):

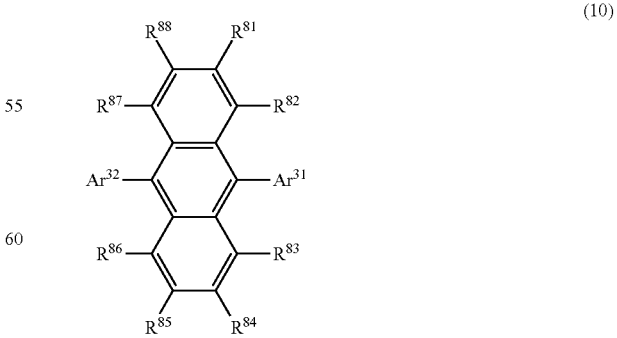

(10)

wherein:
each of $Ar^{31}$ and $Ar^{32}$ independently represents a substituted or unsubstituted aryl group having 6 to 50 ring carbon atoms or a substituted or unsubstituted heterocyclic group having 5 to 50 ring atoms; and each of $R^{81}$ to $R^{88}$ independently represents a hydrogen atom, a substituted or unsubstituted aryl group having 6 to 50 ring carbon atoms, a substituted or unsubstituted heterocyclic group having 5 to 50 ring atoms, a substituted or unsubstituted alkyl group having 1 to 50 carbon atoms, a substituted or unsubstituted alkoxy group having 1 to 50 carbon atoms, a substituted or unsubstituted aralkyl group having 7 to 50 carbon atoms, a substituted or unsubstituted aryloxy group having 6 to 50 ring carbon atoms, a substituted or unsubstituted arylthio group having 6 to 50 ring carbon atoms, a substituted or unsubstituted alkoxycarbonyl group having 2 to 50 carbon atoms, a substituted or unsubstituted silyl group, a carboxyl group, a halogen atom, a cyano group, a nitro group, or a hydroxyl group.

The aryl group having 6 to 50 ring carbon atoms is preferably an aryl group having 6 to 40 ring carbon atoms and more preferably an aryl group having 6 to 30 ring carbon atoms.

The heterocyclic group having 5 to 50 ring atoms is preferably a heterocyclic group having 5 to 40 ring atoms and more preferably a heterocyclic group having 5 to 30 ring atoms.

The alkyl group having 1 to 50 carbon atoms is preferably an alkyl group having 1 to 30 carbon atoms, more preferably an alkyl group having 1 to 10 carbon atoms, and still more preferably an alkyl group having 1 to 5 carbon atoms.

The alkoxy group having 1 to 50 carbon atoms is preferably an alkoxy group having 1 to 30 carbon atoms, more preferably an alkoxy group having 1 to 10 carbon atoms, and still more preferably an alkoxy group having 1 to 5 carbon atoms.

The aralkyl group having 7 to 50 carbon atoms is preferably an aralkyl group having 7 to 30 carbon atoms and more preferably an aralkyl group having 7 to 20 carbon atoms.

The aryloxy group having 6 to 50 ring carbon atoms is preferably an aryloxy group having 6 to 40 ring carbon atoms and more preferably an aryloxy group having 6 to 30 ring carbon atoms.

The arylthio group having 6 to 50 ring carbon atoms is preferably an arylthio group having 6 to 40 ring carbon atoms and more preferably an arylthio group having 6 to 30 ring carbon atoms.

The alkoxycarbonyl group having 2 to 50 carbon atoms is preferably an alkoxycarbonyl group having 2 to 30 carbon atoms, more preferably an alkoxycarbonyl group having 2 to 10 carbon atoms, and still more preferably an alkoxycarbonyl group having 2 to 5 carbon atoms.

Examples of the halogen atom include a fluorine atom, a chlorine atom, and a bromine atom.

Each of $Ar^{31}$ and $Ar^{32}$ particularly preferably represents a substituted or unsubstituted aryl group having 6 to 50 ring carbon atoms.

The anthracene derivative represented by formula (10) is preferably represented by formula (10-1):

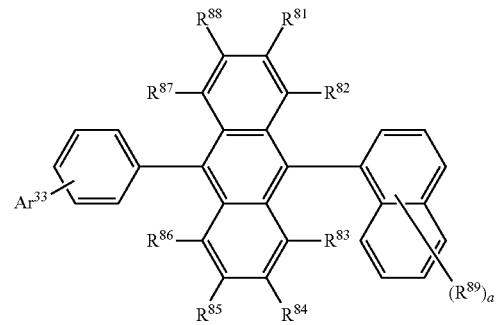

(10-1)

wherein:
$Ar^{33}$ represents a substituted or unsubstituted aryl group having 6 to 50 ring carbon atoms or a substituted or unsubstituted heterocyclic group having 5 to 50 ring atoms;
each of $R^{81}$ to $R^{88}$ is as defined above;
$R^{89}$ is defined in the same manner as in $R^{81}$ to $R^{88}$; and
a is an integer of 1 to 7.

Preferred examples of $R^{81}$ to $R^{88}$ are as described above. Preferred examples of $R^{89}$ are the same as those of $R^{81}$ to $R^{88}$. The subscript a is preferably an integer of 1 to 3 and more preferably 1 or 2.

The aryl group having 6 to 50 ring carbon atoms for $Ar^{33}$ is preferably an aryl group having 6 to 40 ring carbon atoms, more preferably an aryl group having 6 to 30 ring carbon atoms, still more preferably an aryl group having 6 to 20 ring carbon atoms, and particularly preferably an aryl group having 6 to 12 ring carbon atoms.

The arylamine derivative for use as the fluorescent material is preferably an aryldiamine derivative, more preferably an aryldiamine derivative comprising a pyrene skeleton, and still more preferably an aryldiamine derivative having a pyrene skeleton and a dibenzofuran skeleton.

The aryldiamine derivative is preferably an aryldiamine derivative represented by formula (11):

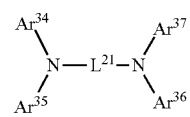

(11)

wherein:
each of $Ar_{34}$ to $Ar^{37}$ independently represents a substituted or unsubstituted aryl group having 6 to 50 ring carbon atoms or a substituted or unsubstituted heteroaryl group having 5 to 50 ring atoms; and
$L^{21}$ represents a substituted or unsubstituted arylene group having 6 to 50 ring carbon atoms or a substituted or unsubstituted heteroarylene group having 5 to 50 ring atoms.

The aryl group having 6 to 50 ring carbon atoms is preferably an aryl group having 6 to 30 ring carbon atoms, more preferably an aryl group having 6 to 20 ring carbon atoms, still more preferably an aryl group having 6 to 12 ring carbon atoms, with a phenyl group and a naphthyl group being particularly preferred.

The heteroaryl group having 5 to 50 ring atoms is preferably a heteroaryl group having 5 to 40 ring atoms, more preferably a heteroaryl group having 5 to 30 ring atoms, and still more preferably a heteroaryl group having 5 to 20 ring atoms, for example, a carbazolyl group, a dibenzofuranyl group and dibenzothiophenyl group, with a dibenzofuranyl group being preferred. Preferred examples of the substituent for the heteroaryl group include an aryl group having 6 to 30, preferably 6 to 20, and more preferably 6 to 12 ring carbon atoms, with a phenyl group and a naphthyl group being more preferred.

The arylene group having 6 to 50 ring carbon atoms is preferably an arylene group having 6 to 40 ring carbon atoms, more preferably an arylene group having 6 to 30 ring carbon atoms, and still more preferably an arylene group having 6 to 20 ring carbon atoms, with a pyrenyl group being particularly preferred.

A double host (host/co-host) system may be used for the light emitting layer. For example, to control the carrier balance in the light emitting layer, an electron transporting host and a hole transporting host may be combinedly used.

The light emitting layer may be also made into a double dopant layer. When two or more kinds of dopant materials having high quantum yield are used in the light emitting layer, each dopant emits light with its own color. For example, a yellow light emitting layer can be obtained by co-depositing a host, a red-emitting dopant and a green-emitting dopant.

The light emitting layer may further comprise a hole transporting material, a electron transporting material, and a polymer binder, if necessary.

The thickness of the light emitting layer is preferably 5 to 50 nm, more preferably 7 to 50 nm and most preferably 10 to 50 nm. If less than 5 nm, the light emitting layer may be difficult to form and the color may be difficult to control. If exceeding 50 nm, the driving voltage is likely to increase.

Electron-Donating Dopant

The organic EL device of the present invention preferably comprises an electron-donating dopant at an interfacial region between the cathode and the emitting unit. With such a construction, the organic EL device has an improved luminance and an elongated lifetime. The electron-donating dopant comprises a metal having a work function of 3.8 eV or less and examples thereof include at least one selected from alkali metal, alkali metal complex, alkali metal compound, alkaline earth metal, alkaline earth metal complex, alkaline earth metal compound, rare earth metal, rare earth metal complex, and rare earth metal compound.

Examples of the alkali metal include Na (work function: 2.36 eV), K (work function: 2.28 eV), Rb (work function: 2.16 eV), and Cs (work function: 1.95 eV), with those having a work function of 2.9 eV or less being particularly preferred. Of the above, preferred are K, Rb, and Cs, more preferred are Rb and Cs, and most preferred is Cs. Examples of the alkaline earth metal include Ca (work function: 2.9 eV), Sr (work function: 2.0 to 2.5 eV), and Ba (work function: 2.52 eV), with those having a work function of 2.9 eV or less being particularly preferred. Examples of the rare earth metal include Sc, Y, Ce, Tb, and Yb, with those having a work function of 2.9 eV or less being particularly preferred.

Examples of the alkali metal compound include alkali oxide, such as $Li_2O$, $Cs_2O$, $K_2O$, and alkali halide, such as LiF, NaF, CsF, and KF, with LiF, $Li_2O$, and NaF being preferred. Examples of the alkaline earth metal compound include BaO, SrO, CaO, and mixture thereof, such as $Ba_xSr_{1-x}O$ (0<x<1) and $Ba_xCA^1_{-x}O$ (0<x<1), with BaO, SrO, and CaO being preferred. Examples of the rare earth compound include $YbF_3$, $ScF_3$, $ScO_3$, $Y_2O_3$, $Ce_2O_3$, $GdF_3$, and $TbF_3$, with $YbF_3$, $ScF_3$, and $TbF_3$ being preferred.

Examples of the alkali metal complex, alkaline earth metal complex, and rare earth metal are not particularly limited as long as containing at least one metal ion selected from alkali metal ions, alkaline earth metal ions, rare earth metal ions, respectively. The ligand is preferably, but not limited to, quinolinol, benzoquinolinol, acridinol, phenanthridinol, hydroxyphenyloxazole, hydroxyphenylthiazole, hydroxydiaryloxadiazole, hydroxydiarylthiadiazole, hydroxyphenylpyridine, hydroxyphenylbenzimidazole, hydroxybenzotriazole, hydroxyfulborane, bipyridyl, phenanthroline, phthalocyanine, porphyrin, cyclopentadiene, β-diketones, azomethines, and derivative thereof.

The electron-donating dopant is added to the interfacial region preferably into a form of layer or island. The electron-donating dopant is added preferably by co-depositing the electron-donating dopant with the organic compound (light emitting material, electron injecting material) for forming the interfacial region by a resistance heating deposition method, thereby dispersing the electron-donating dopant into the organic material. The disperse concentration expressed by the molar ratio of the organic material and the electron-donating dopant is 100:1 to 1:100 and preferably 5:1 to 1:5.

When the electron-donating dopant is formed into a form of layer, a light emitting material or an electron injecting material is made into a layer which serves as an organic layer in the interface, and then, the electron-donating dopant alone is deposited by a resistance heating deposition method into a layer having a thickness preferably 0.1 to 15 nm. When the electron-donating dopant is formed into a form of island, a light emitting material or an electron injecting material is made into a form of island which serves as an organic layer in the interface, and then, the electron-donating dopant alone is deposited by a resistance heating deposition method into a form of island having a thickness preferably 0.05 to 1 nm.

The molar ratio of the main component and the electron-donating dopant in the organic electroluminescence device of the invention is preferably 5:1 to 1:5 and more preferably 2:1 to 1:2.

Electron Transporting Layer

The electron transporting layer is an organic layer disposed between the light emitting layer and the cathode and transports electrons from the cathode to the light emitting layer. If two or more electron transporting layers are provided, the organic layer closer to the cathode may be called an electron injecting layer in some cases. The electron injecting layer injects electrons from the cathode to the organic layer unit efficiently. The material for organic EL device of the invention may be used in the electron transporting layer as the electron transporting material.

An aromatic heterocyclic compound having one or more heteroatoms in a molecule thereof is preferably used as an electron transporting material used in the electron transporting layer, and a nitrogen-containing ring derivative is particularly preferred. In addition, the nitrogen-containing ring derivative is preferably an aromatic ring compound having a nitrogen-containing, 6- or 5-membered ring, or a fused aromatic ring compound having a nitrogen-containing, 6- or 5-membered ring.

The nitrogen-containing ring derivative is preferably, for example, a metal chelate complex of a nitrogen-containing ring represented by formula (A):

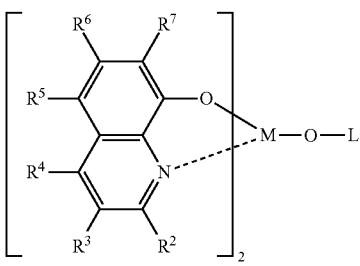
(A)

wherein each of $R^2$ to $R^7$ independently represents a hydrogen atom, a heavy hydrogen atom, a halogen atom, a hydroxyl group, an amino group, a hydrocarbon group having 1 to 40 carbon atoms, an alkoxy group having 1 to 40 carbon atoms, an aryloxy group having 6 to 50 carbon atoms, an alkoxycarbonyl group, or an aromatic heterocyclic group having 5 to 50 ring carbon atoms, each being optionally substituted.

The halogen atom may include fluorine, chlorine, bromine, and iodine.

The substituted amino group may include an alkylamino group, an arylamino group, and an aralkylamino group.

The alkylamino group and the aralkylamino group are represented by $-NQ^1Q^2$. Each of $Q^1$ and $Q^2$ independently represents an alkyl group having 1 to 20 carbon atoms or an aralkyl group having 1 to 20 carbon atoms. One of $Q^1$ and $Q^2$ may be a hydrogen atom or a heavy hydrogen atom.

The arylamino group is represented by $-NAr^1Ar^2$, wherein each of $Ar^1$ and $Ar^2$ independently represents a non-fused aromatic hydrocarbon groups or a fused aromatic hydrocarbon groups, each having 6 to 50 carbon atoms. One of $Ar^1$ and $Ar^2$ may be a hydrogen atom or a heavy hydrogen atom.

Examples of the hydrocarbon group having 1 to 40 carbon atoms include an alkyl group, an alkenyl group, a cycloalkyl group, an aryl group, and an aralkyl group.

The alkoxycarbonyl group is represented by $-COOY'$, wherein $Y'$ is an alkyl group having 1 to 20 carbon atoms.

M is aluminum (Al), gallium (Ga), or indium (In), with In being preferred.

L is a group represented by formula (A') or (A"):

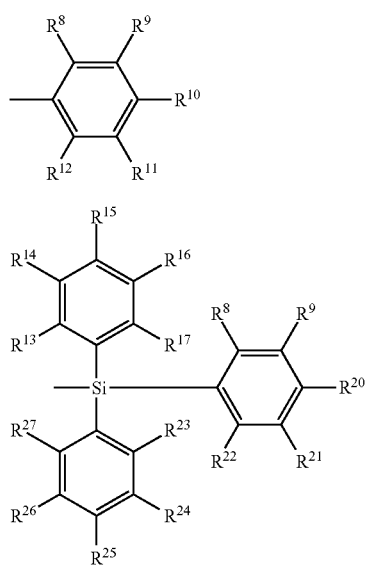
(A')

(A")

wherein each of $R^8$ to $R^{12}$ independently represents a hydrogen atom, a heavy hydrogen atom or a substituted or unsubstituted hydrocarbon group having 1 to 40 carbon atoms. The adjacent two groups may form a ring structure. Each of $R^{13}$ to $R^{27}$ independently represents a hydrogen atom, a heavy hydrogen atom or a substituted or unsubstituted hydrocarbon group having 1 to 40 carbon atoms. The adjacent two groups may form a ring structure.

Examples of the hydrocarbon group having 1 to 40 carbon atoms for $R^8$ to $R^{12}$ and $R^{13}$ to $R^{27}$ in formulae (A') and (A") are the same as those described above with respect to $R^2$ to $R^7$ of formula (A). Examples of the divalent group formed by the adjacent two groups of $R^8$ to $R^{12}$ and $R^{13}$ to $R^{27}$ which completes the ring structure include tetramethylene group, pentamethylene group, hexamethylene group, diphenylmethane-2,2'-diyl group, diphenylethane-3,3'-diyl group, and diphenylpropane-4,4'-diyl group.

The electron transporting compound for the electron transporting layer is preferably a metal complex including 8-hydroxyquinoline or its derivative, an oxadiazole derivative, and a nitrogen-containing heterocyclic derivative. Examples of the metal complex including 8-hydroxyquinoline or its derivative include a metal chelate oxinoid including a chelated oxine (generally, 8-quinolinol or 8-hydroxyquinoline), for example, tris(8-quinolinol)aluminum. Examples of the oxadiazole derivative are shown below:

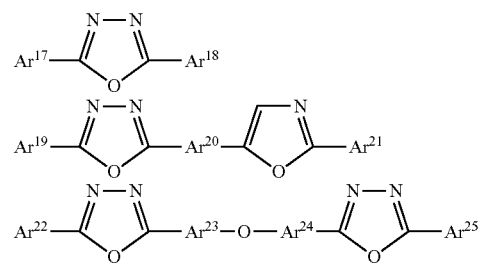

wherein each of $Ar^{17}$, $Ar^{18}$, $Ar^{19}$, $Ar^{21}$, $Ar^{22}$, and $Ar^{25}$ is a substituted or unsubstituted aromatic hydrocarbon group or a substituted or unsubstituted fused aromatic hydrocarbon group each having 6 to 50 carbon atoms, and $Ar^{17}$ and $Ar^{18}$, $Ar^{19}$ and $Ar^{21}$, and $Ar^{22}$ and $Ar^{25}$ may be the same or different. Examples of the aromatic hydrocarbon group and the fused aromatic hydrocarbon group include phenyl group, naphthyl group, a biphenyl group, anthranyl group, perylenyl group, and pyrenyl group. The optional substituent may be an alkyl group having 1 to 10 carbon atoms, an alkoxyl group having 1 to 10 carbon atoms or a cyano group.

Each of $Ar^{20}$, $Ar^{23}$, and $Ar^{24}$ is a substituted or unsubstituted bivalent aromatic hydrocarbon group or a substituted or unsubstituted bivalent fused aromatic hydrocarbon group each having 6 to 50 carbon atoms, and $Ar^{23}$ and $Ar^{24}$ may be the same or different. Examples of the bivalent aromatic hydrocarbon group or the bivalent fused aromatic hydrocarbon group include phenylene group, naphthylene group, biphenylene group, anthranylene group, perylenylene group, and pyrenylene group. The optional substituent may be an alkyl group having 1 to 10 carbon atoms, an alkoxyl group having 1 to 10 carbon atoms or a cyano group.

Electron transporting compounds which have a good thin film-forming property are preferably used. Examples of the electron transporting compound are shown below.

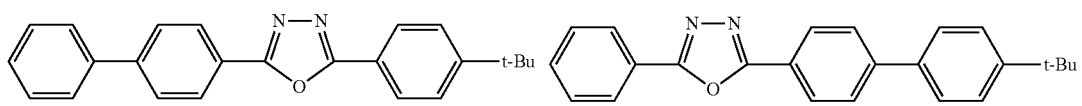
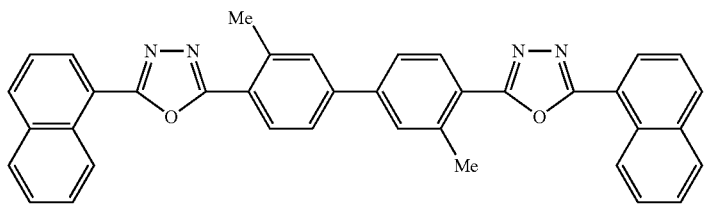
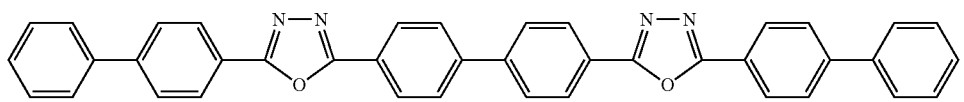
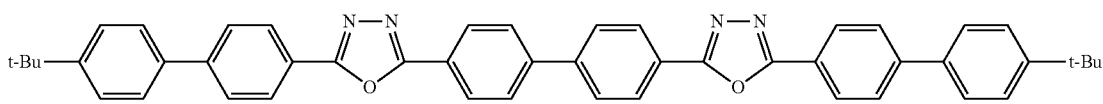
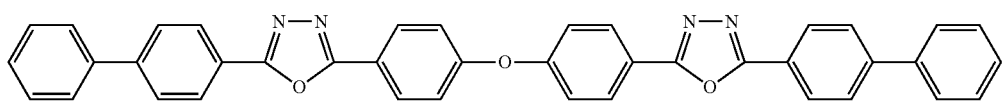

Examples of the nitrogen-containing heterocyclic derivative for use as the electron transporting compound include a nitrogen-containing heterocyclic derivative having the following formulae but exclusive of metal complex, for example, a compound having a 5- or 6-membered ring which has the skeleton represented by formula (B) or having the structure represented by formula (C):

  (B)

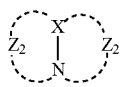  (C)

wherein X is a carbon atom or a nitrogen atom and each of $Z_1$ and $Z_2$ independently represents a group of atoms for completing the nitrogen-containing heteroring.

The nitrogen-containing heterocyclic derivative is more preferably an organic compound which has a nitrogen-containing aromatic polycyclic ring comprising a 5-membered ring or a 6-membered ring. If two or more nitrogen atoms are included, the nitrogen-containing aromatic polycyclic compound preferably has a skeleton of a combination of (B) and (C) or a combination of (B) and (D):

  (D)

The nitrogen-containing group of the nitrogen-containing aromatic polycyclic compound is selected, for example, from the nitrogen-containing heterocyclic groups shown below:

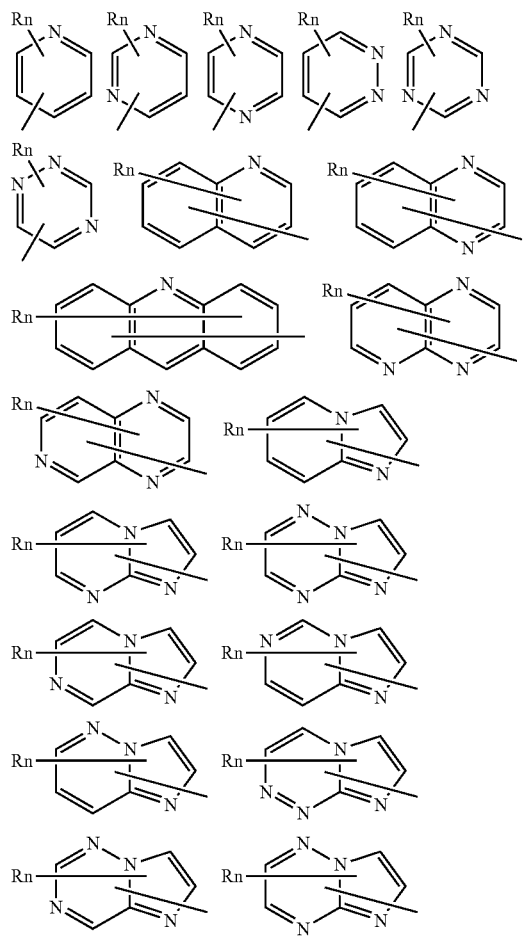

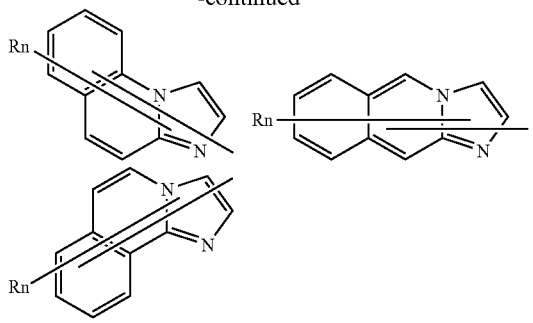

wherein R is an aromatic hydrocarbon group or a fused aromatic hydrocarbon group each having 6 to 40 carbon atoms, an aromatic heterocyclic group or a fused aromatic heterocyclic group each having 3 to 40 carbon atoms, an alkyl group having 1 to 20 carbon atoms, or an alkoxy group having 1 to 20 carbon atoms; and n is an integer of 0 to 5. If n is an integer of 2 or more, R groups may be the same or different.

More preferred is a nitrogen-containing heterocyclic derivative represented by formula (D1):

$$\text{HAr-L}^1\text{-Ar}^1\text{—Ar}^2 \qquad (D1)$$

wherein HAr is a substitute or unsubstituted nitrogen-containing heterocyclic group having 3 to 40 carbon atoms; $L^1$ is a single bond, a substituted or unsubstituted aromatic hydrocarbon group or fused aromatic hydrocarbon group each having 6 to 40 carbon atoms, or a substituted or unsubstituted aromatic heterocyclic group or fused aromatic heterocyclic group each having 3 to 40 carbon atoms; $Ar^1$ is a substitute or unsubstituted divalent aromatic hydrocarbon group having 6 to 40 carbon atoms; and $Ar^2$ is a substitute or unsubstituted aromatic hydrocarbon group or fused aromatic hydrocarbon group each having 6 to 40 carbon atoms or a substituted or unsubstituted aromatic heterocyclic group or fused aromatic heterocyclic group each having 3 to 40 carbon atoms.

HAr is selected, for example, from the following groups:

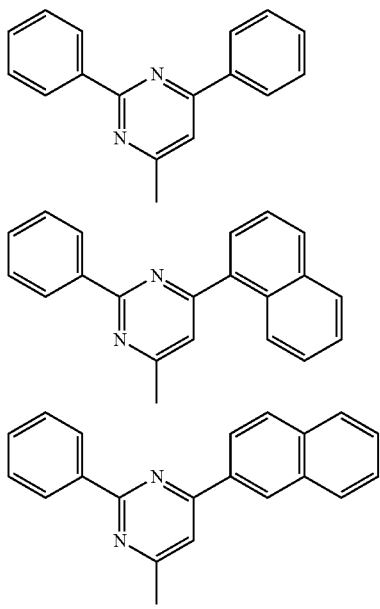

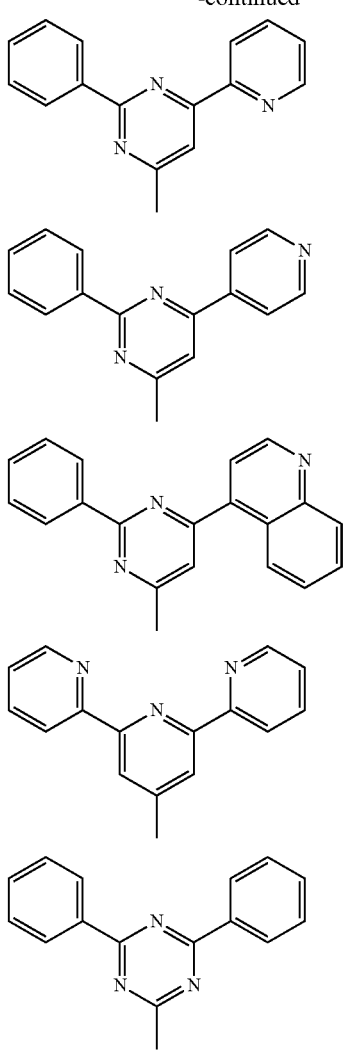

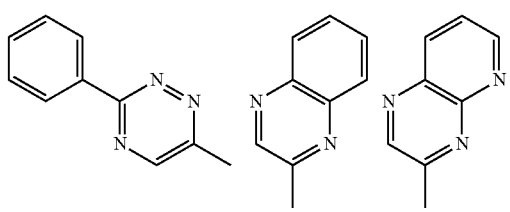

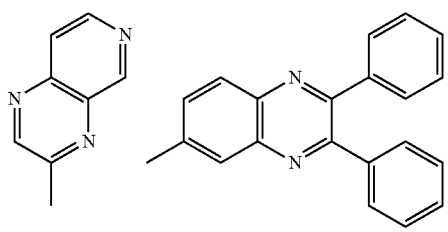

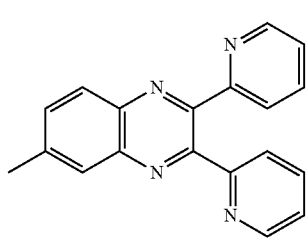

-continued

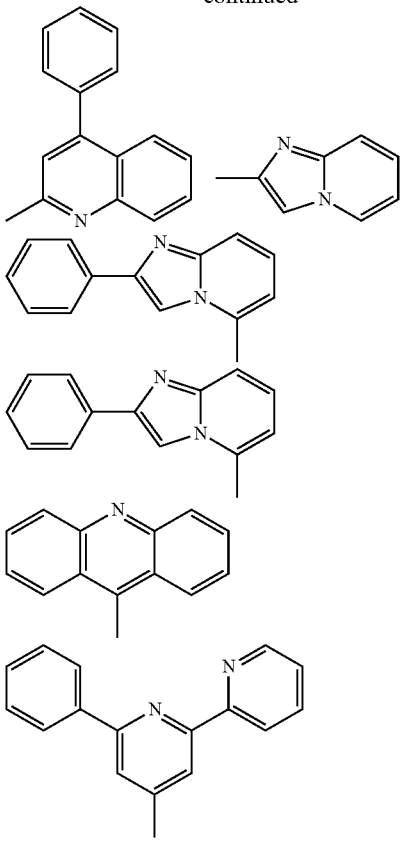

$L^1$ is selected, for example, from the following groups:

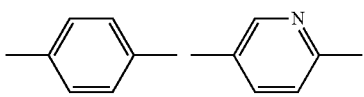

$Ar^1$ is selected, for example, from the following arylanthranyl group represented by formula (D2) or (D3):

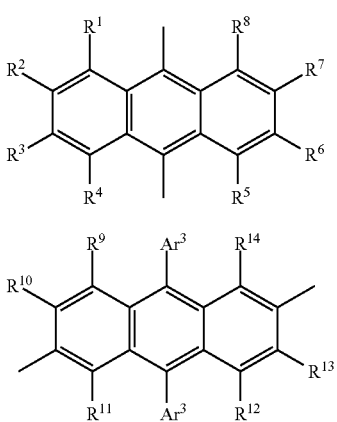

wherein $R^1$ to $R^{14}$ are each independently a hydrogen atom, a halogen atom, an alkyl group having 1 to 20 carbon atoms, an alkoxy group having 1 to 20 carbon atoms, an aryloxy group having 6 to 40 carbon atoms, a substituted or unsubstituted aromatic hydrocarbon group or fused aromatic hydrocarbon group each having 6 to 40 carbon atoms, or a substituted or unsubstituted aromatic heterocyclic group or fused aromatic heterocyclic group each having 3 to 40 carbon atoms; and $Ar^3$ is a substituted or unsubstituted aromatic hydrocarbon group or fused aromatic hydrocarbon group each having 6 to 40 carbon atoms or a substituted or unsubstituted aromatic heterocyclic group or fused aromatic heterocyclic group each having 3 to 40 carbon atoms. Each of $R^1$ to $R^8$ may be selected from a hydrogen atom and a heavy hydrogen atom.

$Ar^2$ is selected, for example, from the following groups:

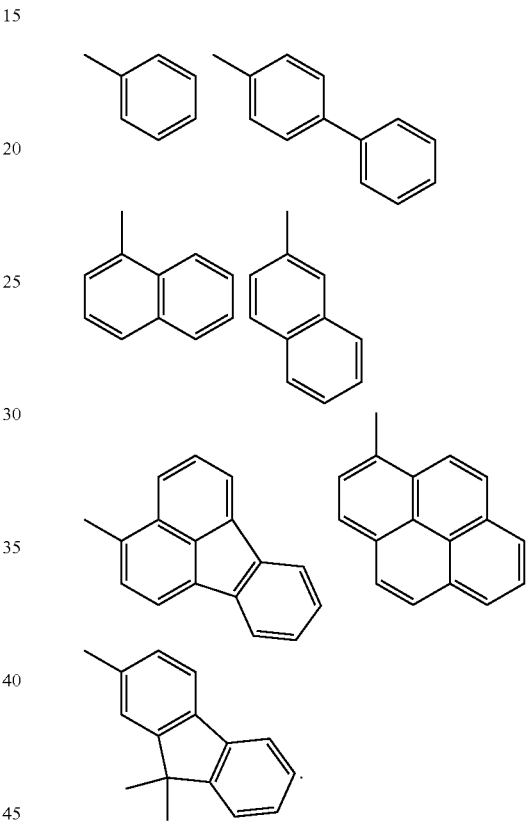

In addition, the following compound is preferably used as the nitrogen-containing aromatic polycyclic compound for use as the electron transporting compound:

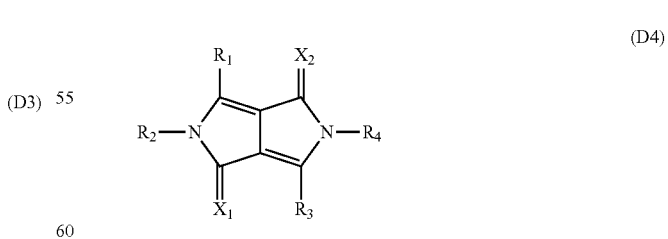

wherein $R_1$ to $R_4$ each independently represent a hydrogen atom, a heavy hydrogen atom, a substituted or unsubstituted aliphatic group having 1 to 20 carbon atoms, a substituted or unsubstituted alicyclic group having 3 to 20 carbon atoms, a substituted or unsubstituted aromatic ring group having 6 to 50 carbon atoms, or a substituted or unsubstituted heterocyclic group having 3 to 50 carbon atoms; and $X_1$ and $X_2$ each independently represent an oxygen atom, a sulfur atom, or dicyanomethylene group.

Further, the following compound is also suitable as the electron transporting compound:

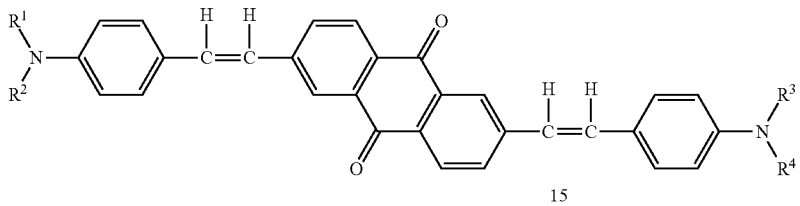

wherein $R^1$, $R^2$, $R^3$, and $R^4$ may be the same or different and each represents an aromatic hydrocarbon group or a fused aromatic hydrocarbon group each represented by formula (D6):

wherein $R^5$, $R^6$, $R^7$, $R^8$, and $R^9$ may be the same or different and each represents a hydrogen atom, a heavy hydrogen atom, a saturated or unsaturated alkoxyl group having 1 to 20 carbon atoms, a saturated or unsaturated alkyl group having 1 to 20 carbon atoms, an amino group, or an alkylamino group having 1 to 20 carbon atoms. At least one of $R^5$, $R^6$, $R^7$, $R^8$, and $R^9$ represents a group other than a hydrogen atom and a heavy hydrogen atom.

Further, a polymer having the nitrogen-containing heterocyclic group or the nitrogen-containing heterocyclic derivative is also usable as the electron transporting compound.

The electron transporting layer in the organic EL device of the invention preferably comprises at least one compound selected from the nitrogen-containing heterocyclic derivatives represented by formulae (E) to (G):

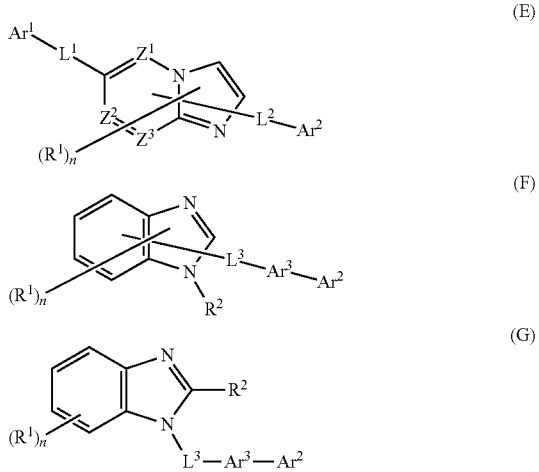

wherein $Z^1$, $Z^2$, and $Z^3$ each independently represent a nitrogen atom or a carbon atom;

$R^1$ and $R^2$ each independently represent a substituted or unsubstituted aryl group having 6 to 50 ring carbon atoms, a substituted or unsubstituted heteroaryl group having 5 to 50 ring atoms, a substituted or unsubstituted alkyl group having 1 to 20 carbon atoms, a substituted or unsubstituted haloalkyl group having 1 to 20 carbon atoms, or a substituted or unsubstituted alkoxyl group having 1 to 20 carbon atoms;

n is an integer of 0 to 5, when n is an integer of 2 or more, $R^1$ groups may be the same or different, and the adjacent two $R^1$ groups may bond to each other to form a substituted or unsubstituted hydrocarbon ring;

$Ar^1$ represents a substituted or unsubstituted aryl group having 6 to 50 ring carbon atoms or a substituted or unsubstituted heteroaryl group having 5 to 50 ring atoms;

$Ar^2$ represents a hydrogen atom, a substituted or unsubstituted alkyl group having 1 to 20 carbon atoms, a substituted or unsubstituted haloalkyl group having 1 to 20 carbon atoms, a substituted or unsubstituted alkoxyl group having 1 to 20 carbon atoms, a substituted or unsubstituted aryl group having 6 to 50 ring carbon atoms, or a substituted or unsubstituted heteroaryl group having 5 to 50 ring atoms;

provided that one of $Ar^1$ and $Ar^2$ is a substituted or unsubstituted condensed aromatic hydrocarbon ring group having 10 to 50 ring carbon atoms or a substituted or unsubstituted condensed aromatic heterocyclic group having 9 to 50 ring atoms;

$Ar^3$ represents a substituted or unsubstituted arylene group having 6 to 50 ring carbon atoms or a substituted or unsubstituted heteroarylene group having 5 to 50 ring atoms; and $L^1$, $L^2$, and $L^3$ each independently represent a single bond, a substituted or unsubstituted arylene group having 6 to 50 ring carbon atoms or a substituted or unsubstituted divalent condensed aromatic heterocyclic group having 9 to 50 ring atoms.

Examples of the aryl group having 6 to 50 ring carbon atoms include phenyl group, naphthyl group, anthryl group, phenanthryl group, naphthacenyl group, chrysenyl group, pyrenyl group, a biphenyl group, terphenyl group, tolyl group, fluoranthenyl group, and fluorenyl group.

Examples of the heteroaryl group having 5 to 50 ring atoms include pyrrolyl group, furyl group, thiophenyl group, silolyl group, pyridyl group, quinolyl group, isoquinolyl group, benzofuryl group, imidazolyl group, pyrimidyl group, carbazolyl group, selenophenyl group, oxadiazolyl group, triazolyl group, pyrazinyl group, pyridazinyl group, triazinyl group, quinoxalinyl group, acridinyl group, imidazo[1,2-a]pyridinyl group, and imidazo[1,2-a]pyrimidinyl.

Examples of the alkyl group having 1 to 20 carbon atoms include methyl group, ethyl group, propyl group, butyl group, pentyl group, and hexyl group.

Examples of the haloalkyl group having 1 to 20 carbon atoms include the groups obtained by replacing one or more hydrogen atoms of the alkyl group mentioned above with at least one halogen atom selected from fluorine, chlorine, iodine, and bromine.

Examples of the alkyl moiety of the alkoxyl group having 1 to 20 carbon atoms include the alkyl group mentioned above.

Examples of the arylene groups include the groups obtained by removing one hydrogen atom from the aryl group mentioned above.

Examples of the divalent condensed aromatic heterocyclic group having 9 to 50 ring atoms include the groups obtained by removing one hydrogen atom from the condensed aromatic heterocyclic group mentioned above as the heteroaryl group.

The thickness of the electron transporting layer is preferably, but not particularly limited to, 1 to 100 nm.

Preferred examples of the material for a electron injecting layer optionally formed adjacent to the electron transporting layer include, in addition to the nitrogen-containing ring derivative, an inorganic compound, such as an insulating material and a semiconductor. The electron injecting layer containing the insulating material or the semiconductor effectively prevents the leak of electric current to enhance the electron injecting properties.

The insulating material is preferably at least one metal compound selected from the group consisting of alkali metal chalcogenides, alkaline earth metal chalcogenides, alkali metal halides and alkaline earth metal halides. The alkali metal chalcogenide, etc. mentioned above are preferred because the electron injecting properties of the electron injecting layer are further enhanced. Examples of preferred alkali metal chalcogenide include $Li_2O$, $K_2O$, $Na_2S$, $Na_2Se$ and $Na_2O$, and examples of preferred alkaline earth metal chalcogenide include CaO, BaO, SrO, BeO, BaS and CaSe. Examples of preferred alkali metal halide include LiF, NaF, KF, LiCl, KCl and NaCl. Examples of the alkaline earth metal halide include fluorides, such as $CaF_2$, $BaF_2$, $SrF_2$, $MgF_2$ and $BeF_2$, and halides other than fluorides.

Examples of the semiconductor include oxides, nitrides or oxynitrides of at least one element selected from the group consisting of Ba, Ca, Sr, Yb, Al, Ga, In, Li, Na, Cd, Mg, Si, Ta, Sb and Zn. The semiconductor may be used alone or in combination of two or more. The inorganic compound included in the electron injecting layer preferably forms a microcrystalline or amorphous insulating thin film. If the electron injecting layer is formed from such an insulating thin film, the pixel defects, such as dark spots, can be decreased because a more uniform thin film is formed. Examples of such inorganic compound include the alkali metal chalcogenide, the alkaline earth metal chalcogenide, the alkali metal halide and the alkaline earth metal halide.

When using the insulating material or the semiconductor, the thickness of its layer is preferably about 0.1 to 15 nm. The electron injecting layer in the invention may contain the electron-donating dopant mentioned above.

Hole Transporting Layer

The hole injecting/transporting layer is an organic layer formed between the light emitting layer and the anode and has a function of transporting holes from the anode to the light emitting layer. When the hole transporting layer is formed by two or more layers, the layer closer to the anode may be defined as the hole injecting layer in some cases. The hole injecting layer has a function of efficiently injecting holes from the anode to the organic layer unit. The material for organic EL device of the invention may be used in the hole transporting layer as a hole transporting material.

Another preferred material for the hole transporting layer may include an aromatic amine compound, for example, an aromatic amine derivative represented by formula (H):

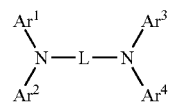

(H)

wherein each of $Ar^1$ to $Ar^4$ represents a substituted or unsubstituted aromatic hydrocarbon group or fused aromatic hydrocarbon group having 6 to 50 ring carbon atoms, a substituted or unsubstituted aromatic heteroaryl group or fused aromatic heteroaryl group having 5 to 50 ring atoms, or a group wherein the aromatic hydrocarbon group or fused aromatic hydrocarbon group is bonded to the aromatic heteroaryl group or fused aromatic heteroaryl group.

L represents a substituted or unsubstituted aromatic hydrocarbon group or fused aromatic hydrocarbon group having 6 to 50 ring carbon atoms or a substituted or unsubstituted aromatic heteroaryl group or fused aromatic heteroaryl group having 5 to 50 ring atoms.

Examples of the compound represented by formula (H) are shown below.

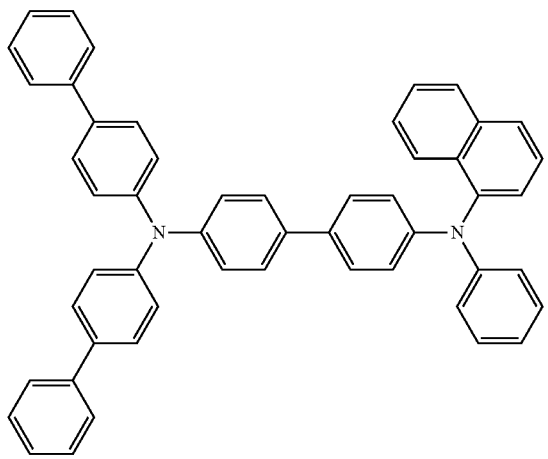

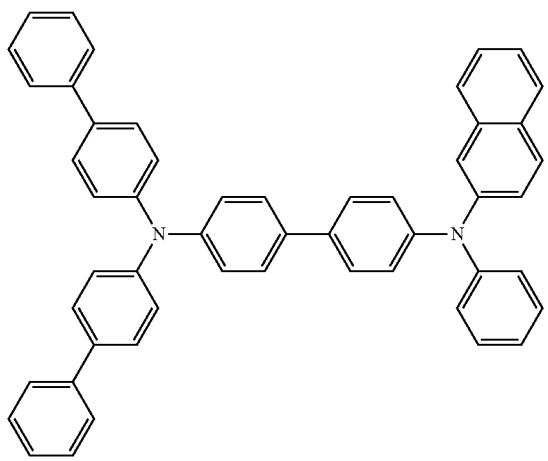

143
-continued
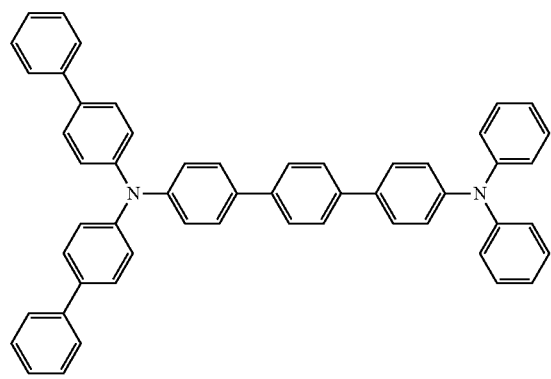
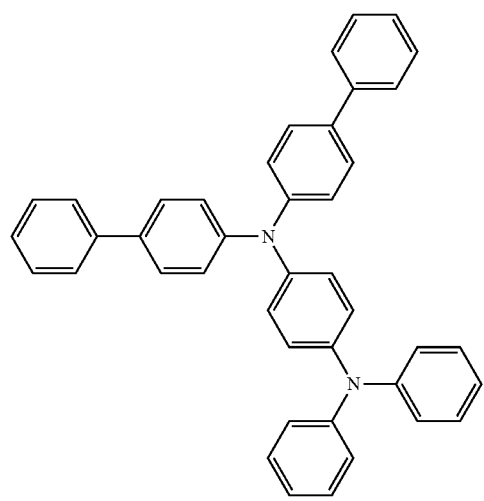
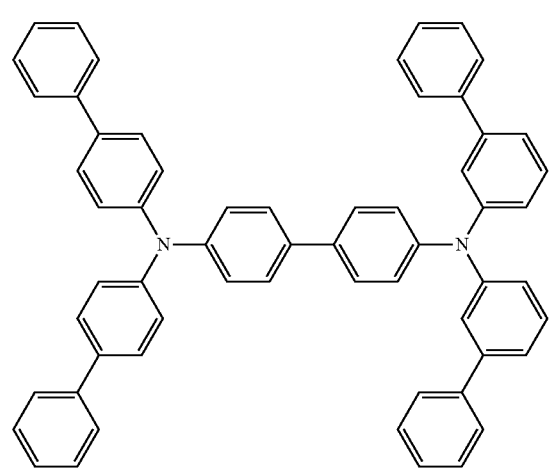
144
-continued
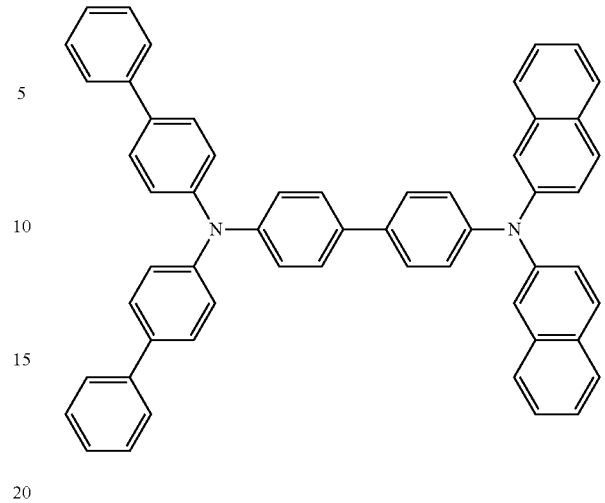
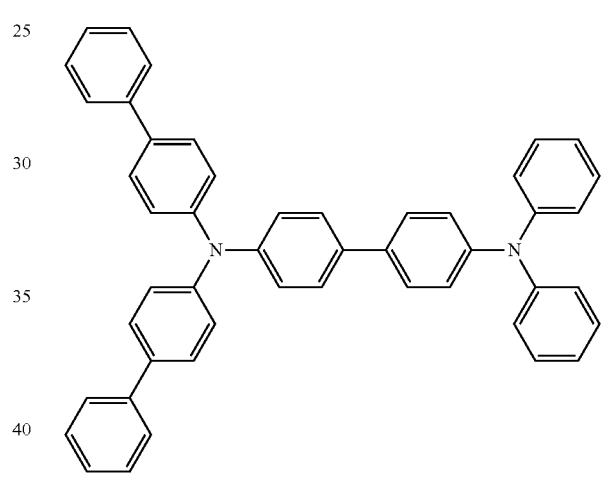
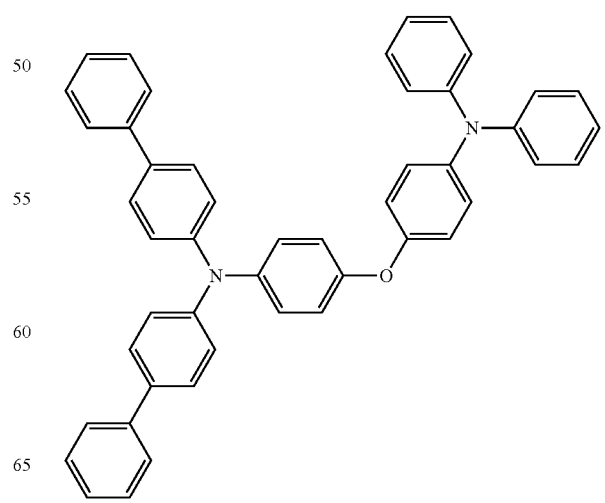

145
-continued
146
-continued
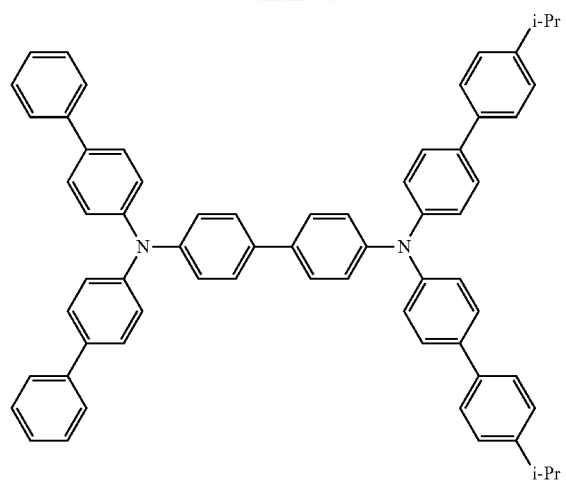
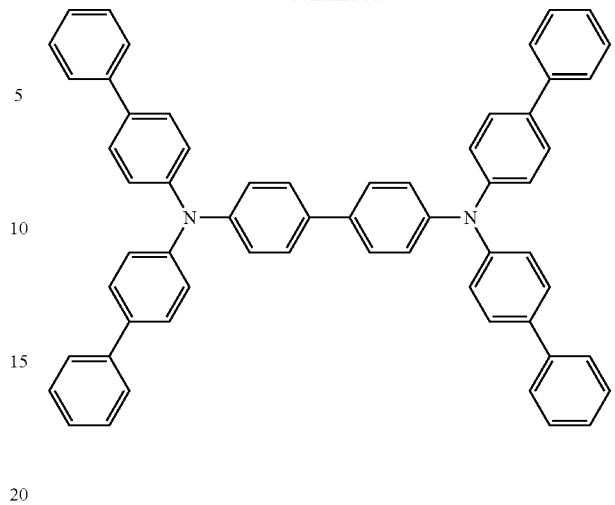
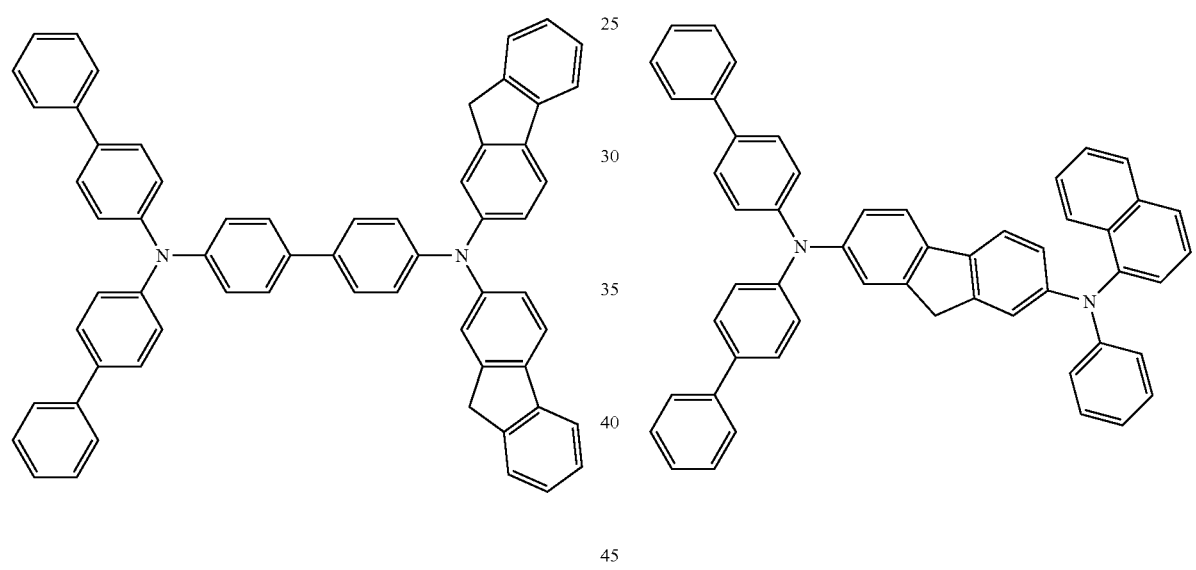
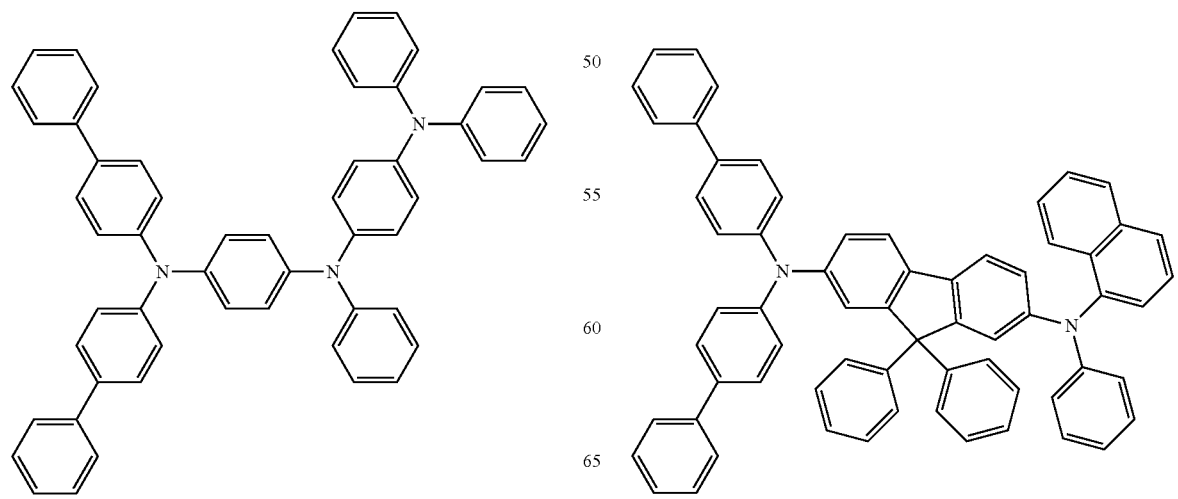

147
-continued
148
-continued
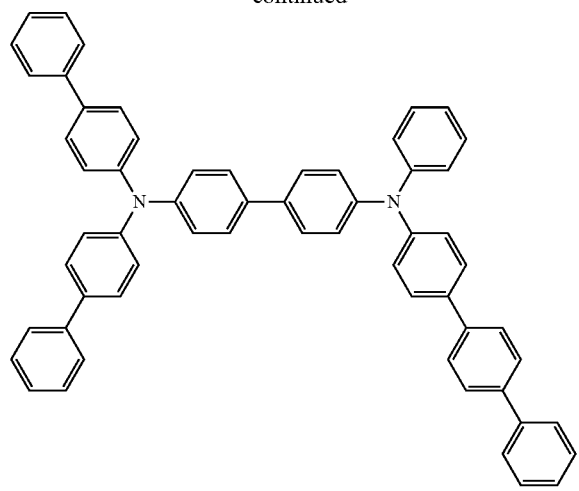
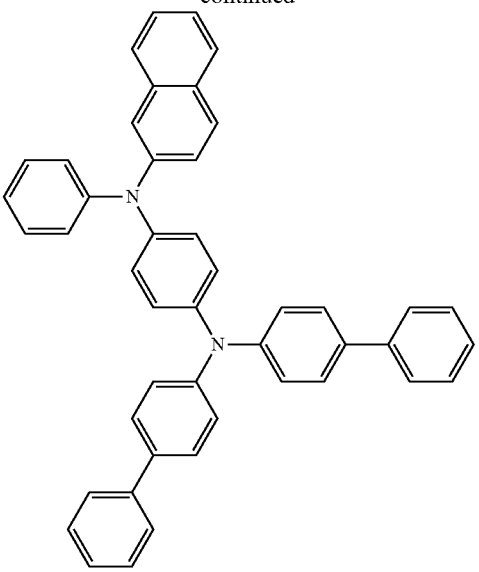
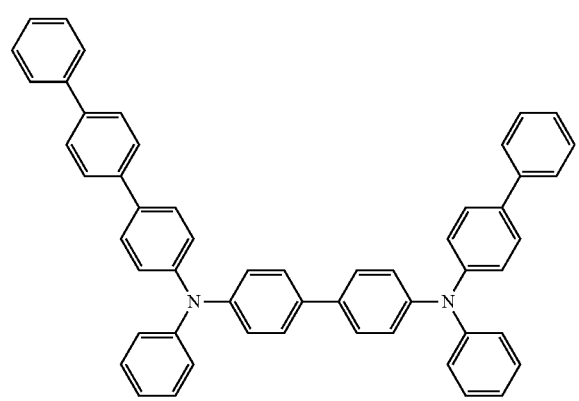
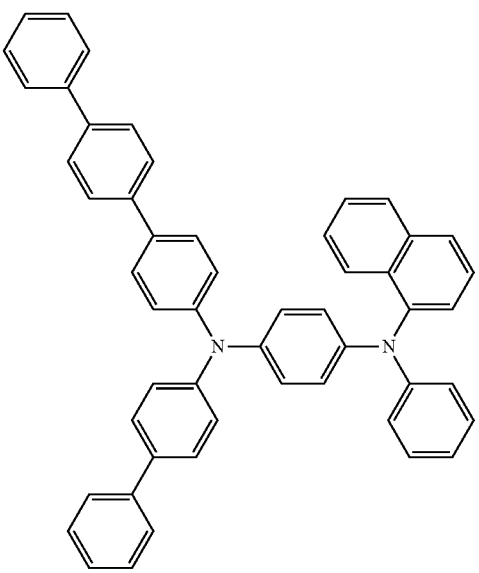
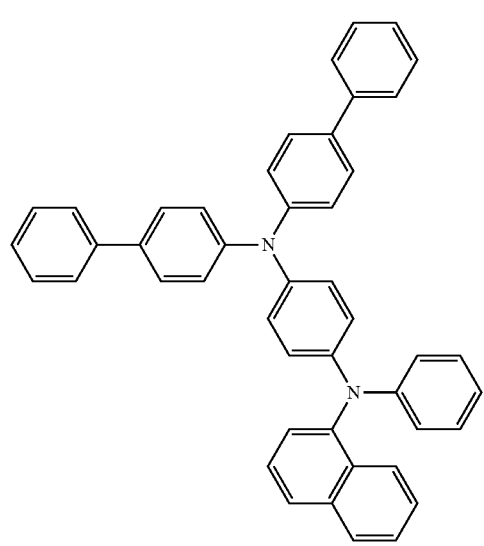
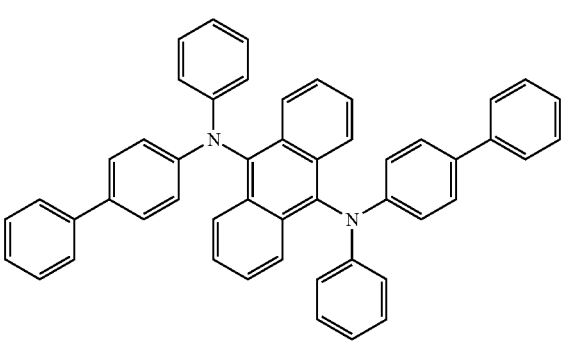

149
-continued
150
-continued
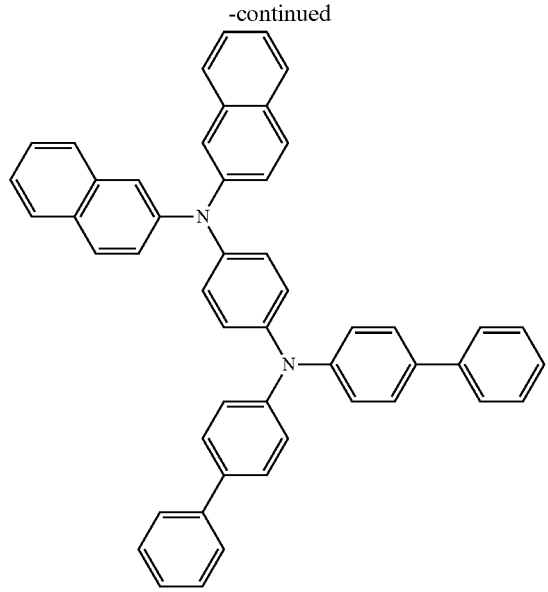
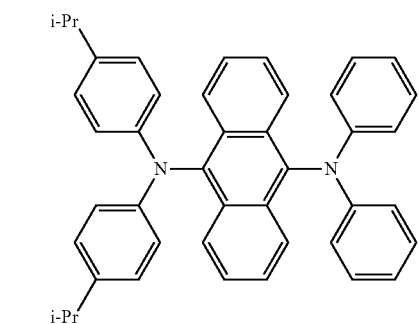
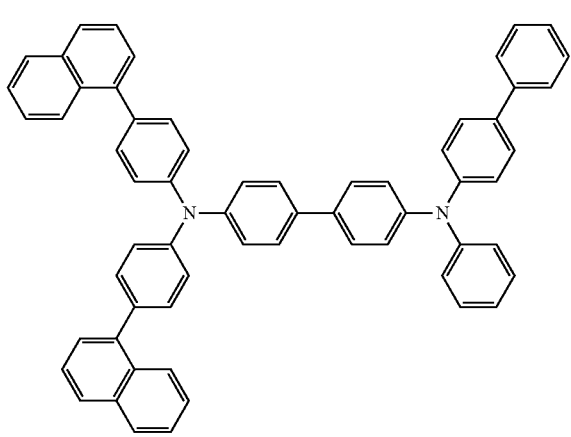
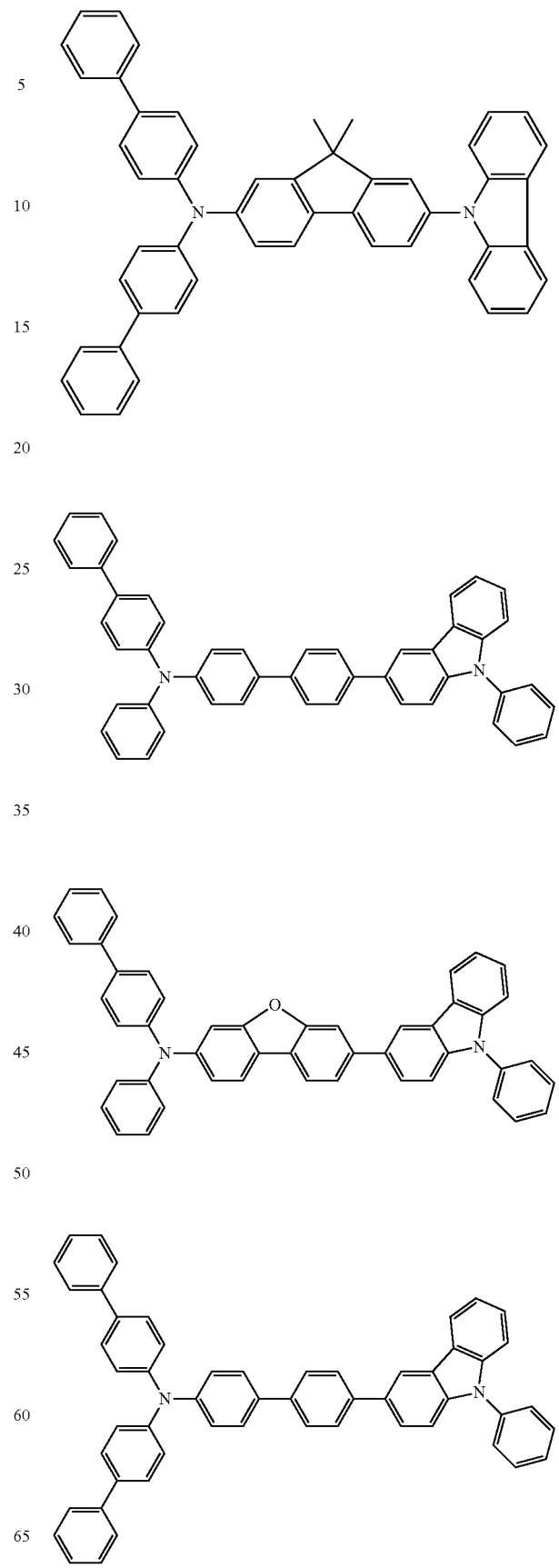

-continued
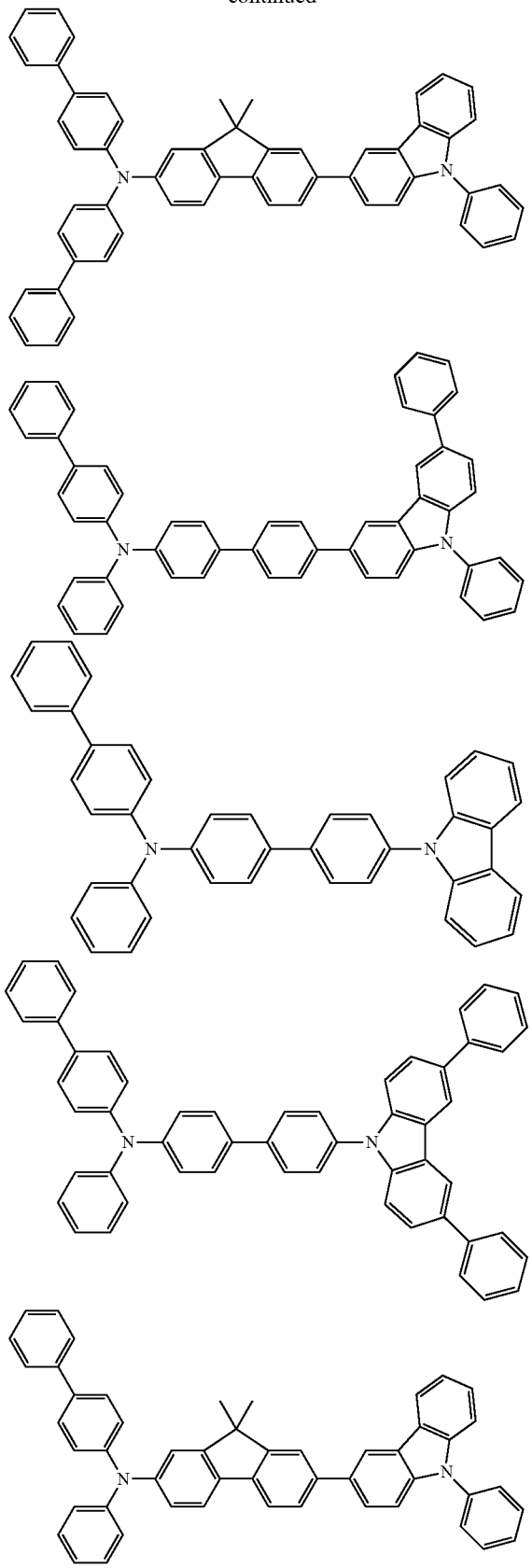
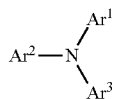
wherein $Ar^1$ to $Ar^3$ are the same as defined with respect to $A^1$ to $Ar^4$ of formula (H). Examples of the compound represented by formula (J) are shown below, although not limited thereto.
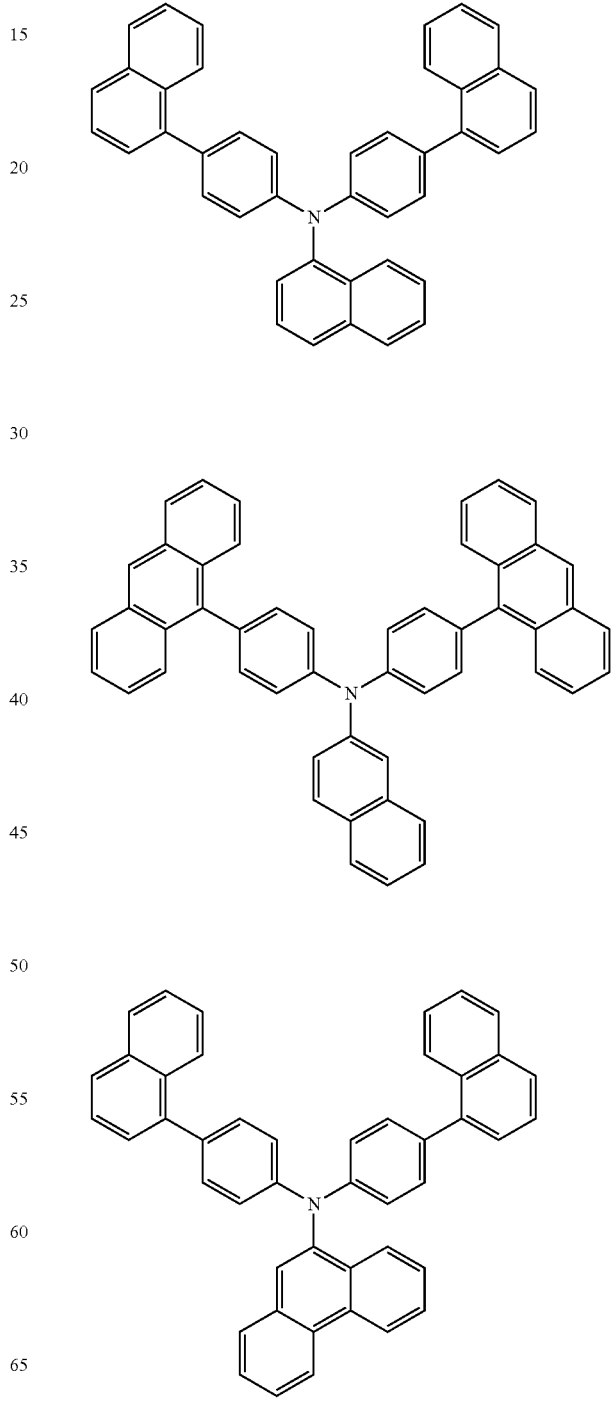
An aromatic amine represented by formula (J) is also preferably used to form the hole transporting layer:

153
-continued
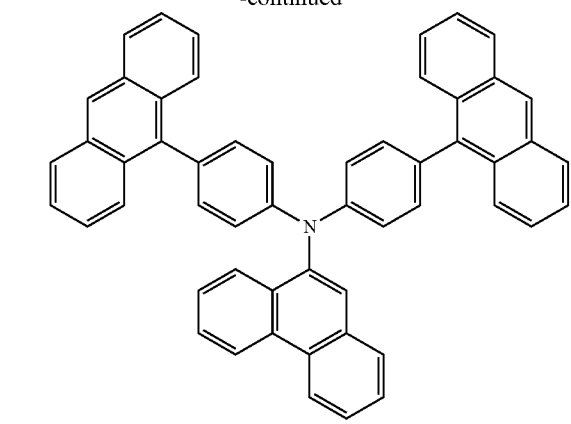
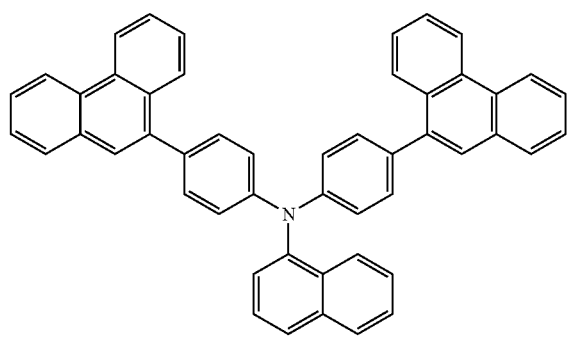
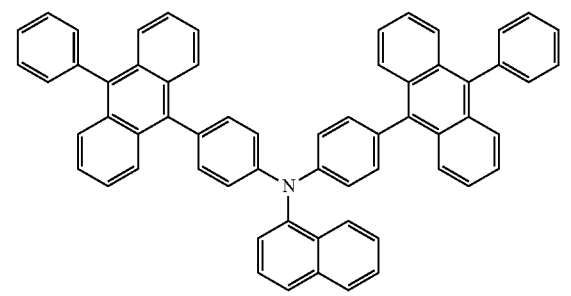
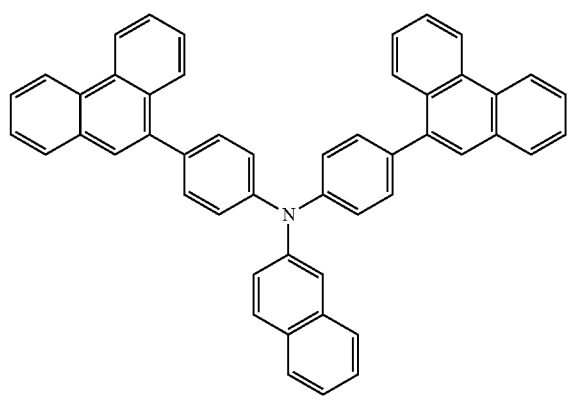
154
-continued
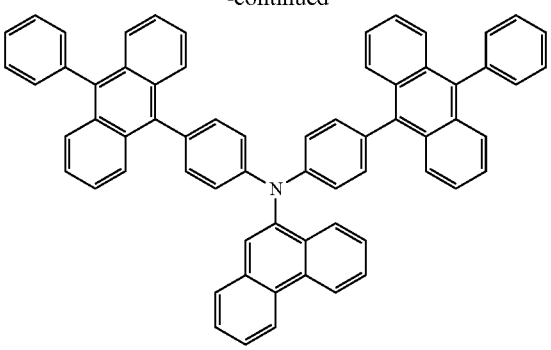
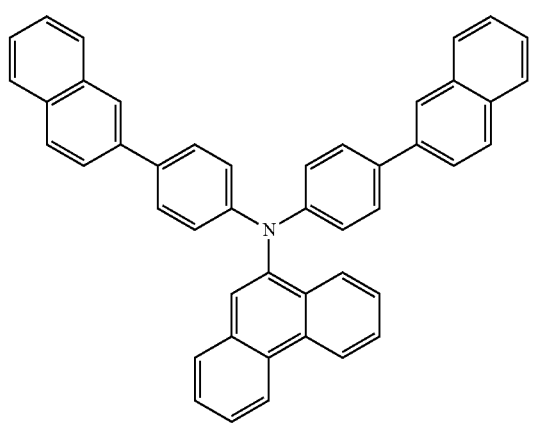
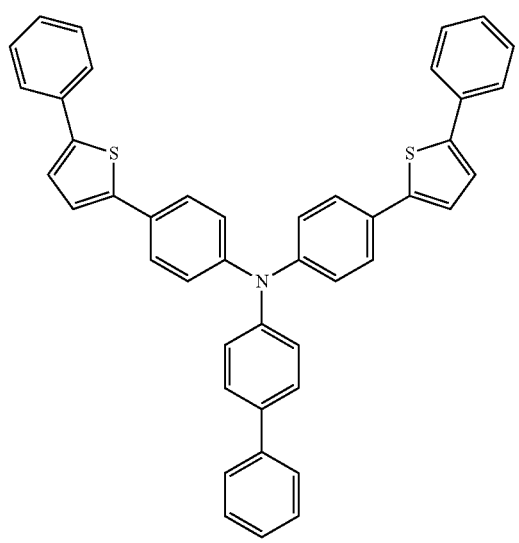
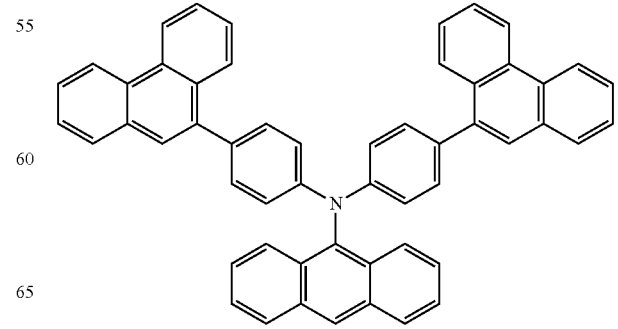

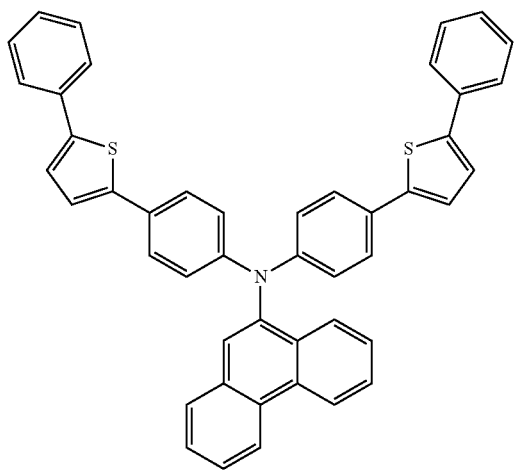
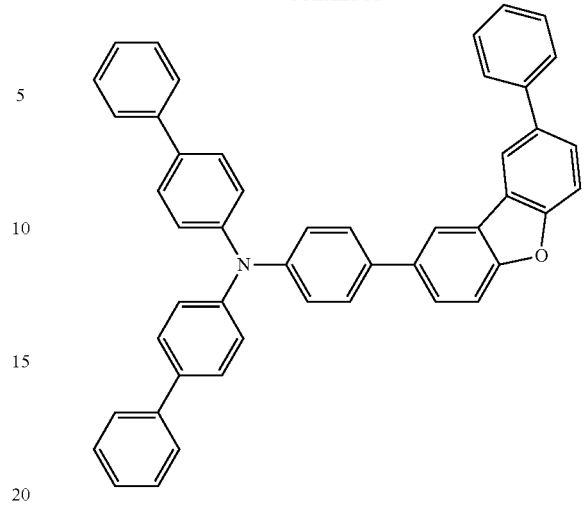
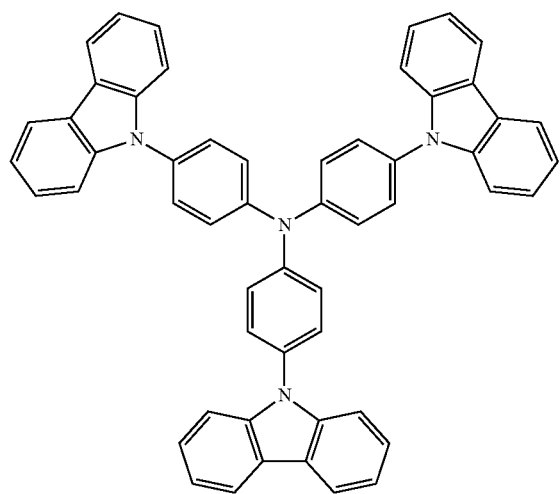
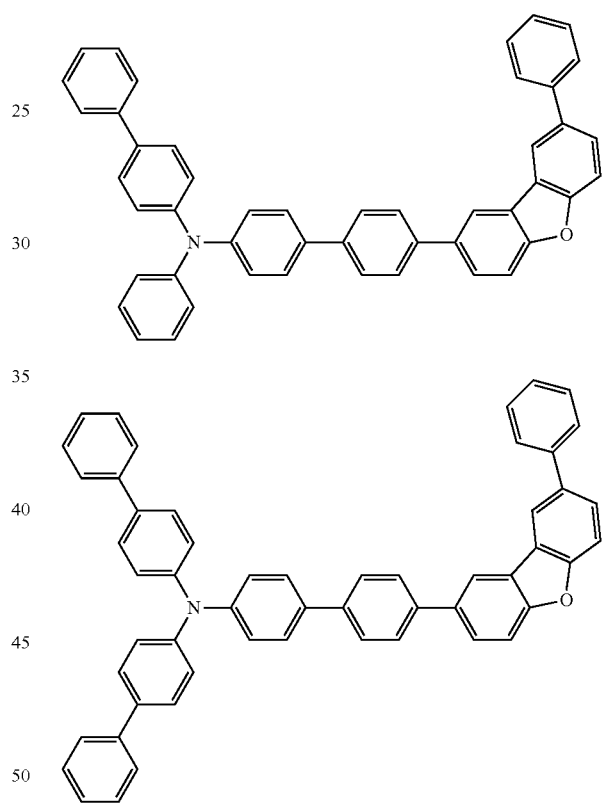
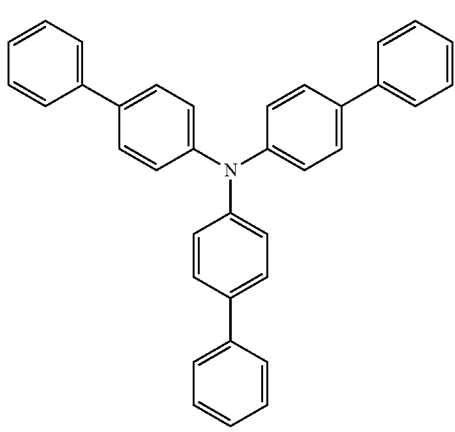

The hole transporting layer may be made into two-layered structure of a first hole transporting layer (anode side) and a second hole transporting layer (cathode side).

The thickness of the hole transporting layer is preferably 10 to 200 nm, although not particularly limited thereto.

The organic EL device of the invention may have a layer comprising an acceptor material which is disposed in contact with the anode side of each of the hole transporting layer and the first hole transporting layer. With such a layer, it is expected that the driving voltage is lowered and the production cost is reduced.

The acceptor material is preferably a compound represented by formula (K):

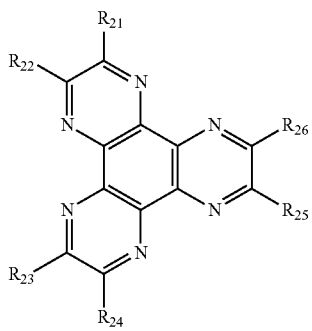

(K)

wherein $R_{21}$ to $R_{26}$ may be the same or different and each independently represent a cyano group, —$CONH_2$, a carboxyl group, or —$COOR_{27}$ wherein $R_{27}$ represents an alkyl group having 1 to 20 carbon atoms or a cycloalkyl group having 3 to 20 carbon atoms. One or more of a pair of $R_{21}$ and $R_{22}$, a pair of $R_{23}$ and $R_{24}$, and a pair of $R_{25}$ and $R_{26}$ may bond to each other to form a group represented by —CO—O—CO—.

Examples of $R_{27}$ include methyl group, ethyl group, n-propyl group, isopropyl group, n-butyl group, isobutyl group, t-butyl group, cyclopentyl group, and cyclohexyl group.

The thickness of the layer comprising the acceptor material is preferably 5 to 20 nm, although not particularly limited thereto.

N/P Doping

The carrier injecting properties of the hole transporting layer and the electron transporting layer can be controlled by, as described in JP 3695714B, the doping (n) with a donor material or the doping (p) with an acceptor material.

A typical example of the n-doping is an electron transporting material doped with a metal, such as Li and Cs, and a typical example of the p-doping is a hole transporting material doped with an acceptor material, such as $F_4TCNQ$ (2,3,5,6-Tetrafluoro-7,7,8,8-tetracyanoquinodimethane).

Space Layer

For example, in an organic EL device wherein a fluorescent light emitting layer and a phosphorescent light emitting layer are laminated, a space layer is disposed between the fluorescent light emitting layer and the phosphorescent light emitting layer to prevent the diffusion of excitons generated in the phosphorescent light emitting layer to the fluorescent light emitting layer or to control the carrier balance. The space layer may be disposed between two or more phosphorescent light emitting layers.

Since the space layer is disposed between the light emitting layers, a material combining the electron transporting ability and the hole transporting ability is preferably used for forming the space layer. To prevent the diffusion of triplet energy in the adjacent phosphorescent light emitting layer, the triplet energy of the material for the space layer is preferably 2.6 eV or more. The materials described with respect to the hole transporting layer are usable as the material for the space layer. The material for organic EL device of the invention may be used as the material for the space layer.

Blocking Layer

The organic EL device of the invention preferably has a blocking layer, such as an electron blocking layer, a hole blocking layer, and a triplet blocking layer, which is disposed adjacent to the light emitting layer. The electron blocking layer is a layer which prevents the diffusion of electrons from the light emitting layer to the hole transporting layer. The hole blocking layer is a layer which prevents the diffusion of holes from the light emitting layer to the electron transporting layer. The material for organic EL device of the invention may be used as the material for the hole blocking layer.

The triplet blocking layer prevents the diffusion of triplet excitons generated in the light emitting layer to adjacent layers and has a function of confining the triplet excitons in the light emitting layer, thereby preventing the deactivation of energy on molecules other than the emitting dopant of triplet excitons, for example, on molecules in the electron transporting layer.

If a phosphorescent device having a triplet blocking layer satisfies the following energy relationship:

$E^T_d < E^T_{TB}$ wherein $E^T_d$ is the triplet energy of the phosphorescent dopant in the light emitting layer and $E^T_{TB}$ is the triplet energy of the compound forming the triplet blocking layer, the triplet excitons of phosphorescent dopant are confined (not diffuse to other molecules). Therefore, the energy deactivation process other than the emission on the phosphorescent dopant may be prevented to cause the emission with high efficiency. However, even in case of satisfying the relationship of $E^T_d < E^T_{TB}$, the triplet excitons may move into other molecules if the energy difference ($\Delta E^T = E^T_{TB} - E^T_d$) is small, because the energy difference $\Delta E^T$ may be overcome by the absorption of ambient heat energy when driving a device at around room temperature as generally employed in practical drive of device. As compared with the fluorescent emission, the phosphorescent emission is relatively likely to be affected by the diffusion of excitons due to the heat absorption because the lifetime of triplet excitons is longer. Therefore, as for the energy difference $\Delta E^T$, the larger as compared with the heat energy of room temperature, the better. The energy difference $\Delta E^T$ is more preferably 0.1 eV or more and particularly preferably 0.2 eV or more. In fluorescent devices, the material for organic EL device of the invention is usable as the material for triplet blocking layer of the TTF device described in WO 2010/134350A1.

The electron mobility of the material for the triplet blocking layer is preferably $10^{-6}$ $cm^2$/Vs or more at an electric field strength in a range of 0.04 to 0.5 MV/cm. There are several methods for measuring the electron mobility of organic material, for example, Time of Flight method. In the present invention, the electron mobility is determined by impedance spectroscopy.

The electron mobility of the electron injecting layer is preferably $10^{-6}$ $cm^2$/Vs or more at an electric field strength in a range of 0.04 to 0.5 MV/cm. Within the above range, the injection of electrons from the cathode to the electron transporting layer is promoted and the injection of electrons to the adjacent blocking layer and light emitting layer is also promoted, thereby enabling to drive a device at lower voltage.

The organic electroluminescence device of the invention usable in electronic equipment, for example, as display parts, such as organic EL panel module, display devices of television sets, mobile phones, personal computer, etc., and light emitting sources of lighting equipment and vehicle lighting equipment.

EXAMPLES

The present invention will be described in more detail with reference to the examples. However, it should be noted that the scope of the invention is not limited to the following examples.

Synthesis Example 1

Synthesis of Compound 1

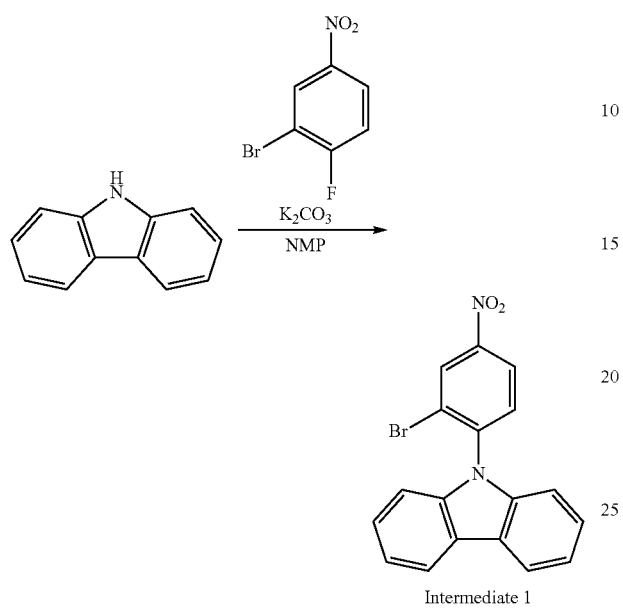

Intermediate 1

Carbazole (19 g), 2-bromo-1-fluoro-4-nitrobenzene (25 g), and potassium carbonate (31 g) were added to 200 ml of 1-methyl-2-pyrrolidone (NMP), and the resultant mixture was stirred at 150° C. for 9 h. The reaction solution was added with water and extracted with hexane, and the extract was dried over anhydrous sodium sulfate. After removing the solvent by evaporation, the residue was purified by column chromatography to obtain the intermediate 1 as yellow solid (17 g).

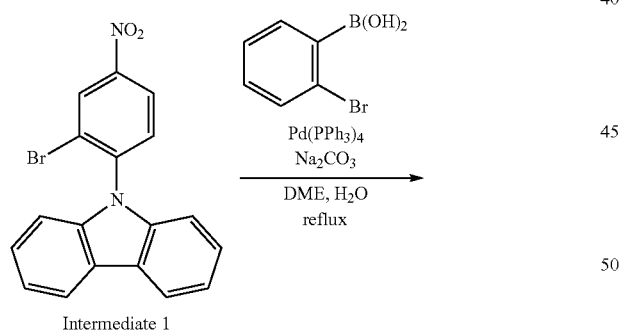

Intermediate 1

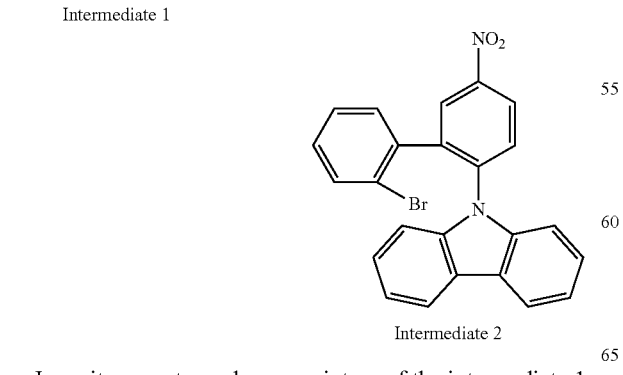

Intermediate 2

In a nitrogen atmosphere, a mixture of the intermediate 1 (12 g), 2-bromophenylboronic acid (6.5 g), tetrakis(triphenylphosphine)palladium (0.37 g), and sodium carbonate (14 g) in 100 ml of 1,2-dimethoxyethane (DME) and 50 ml of water was refluxed under heating for 0.5 h. The reaction solution was added with water and extracted with methylene dichloride. The extract was dried over anhydrous sodium sulfate. After removing the solvent by evaporation, the residue was purified by column chromatography to obtain the intermediate 2 as yellow solid (11 g).

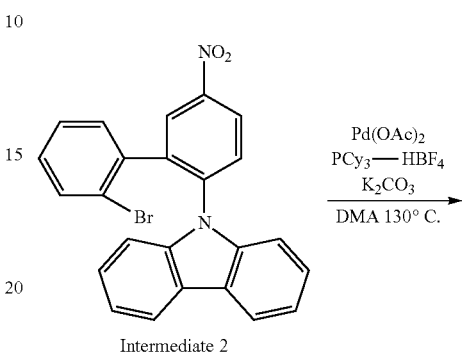

Intermediate 2

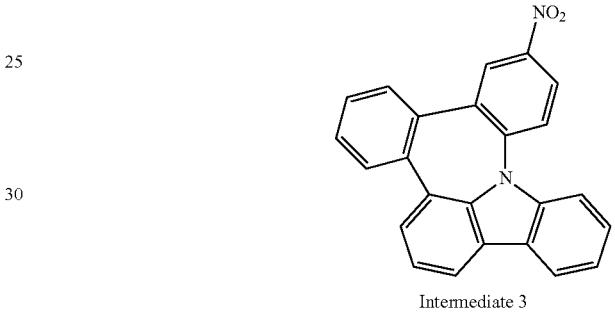

Intermediate 3

In a nitrogen atmosphere, a mixture of the intermediate 2 (11 g), palladium acetate (0.11 g), tricyclohexylphosphonium tetrafluoroborate (0.37 g), and potassium carbonate (6.9 g) in 100 ml of N,N-dimethylacetamide (DMA) was stirred at 140° C. for 8. The reaction solution was added with water and extracted with methylene dichloride, and the extract was dried over anhydrous sodium sulfate. After removing the solvent by evaporation, the residue was purified by column chromatography to obtain the intermediate 3 as yellow solid (6.4 g).

$^1$H-NMR (400 MHz, CDCl$_3$, TMS):

δ 7.38-7.44 (3H, m), 7.47-7.52 (3H, m), 7.56 (1H, d, J=9 Hz), 7.64 (1H, dd, J=5 Hz, 4 Hz), 7.70 (1H, d, J=8 Hz), 7.77 (1H, d, J=8 Hz), 7.86 (1H, dd, J=7 Hz, 1 Hz), 8.02 (1H, d, J=7 Hz), 8.04 (1H, dd, J=9 Hz, 3 Hz), 8.38 (1H, d, J=3 Hz).

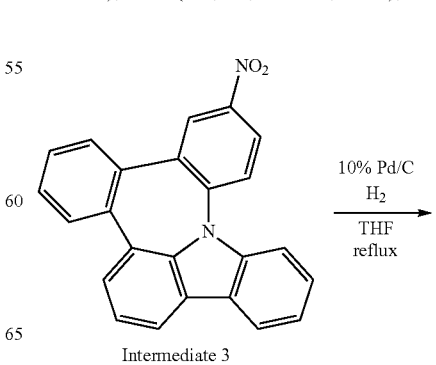

Intermediate 3

-continued

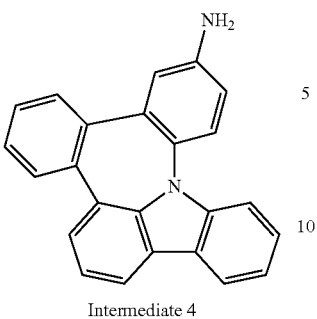
Intermediate 4

In a hydrogen atmosphere, a mixture of the intermediate 3 (5.5 g) and an activated carbon carrying 10% palladium (1.6 g) in 150 ml of tetrahydrofuran (THF) was refluxed under heating for 8 h. The reaction solution was filtered. After removing the solvent by evaporation, the residue was purified by column chromatography to obtain the intermediate 4 as yellow solid (5.0 g).

$^1$H-NMR (400 MHz, CDCl$_3$, TMS):

δ 6.53 (1H, dd, J=9 Hz, 2 Hz), 6.82 (1H, d, J=2 Hz), 7.16 (1H, d, J=8 Hz), 7.29 (1H, ddd, J=8 Hz, 8 Hz, 1 Hz), 7.34 (1H, dd, J=8 Hz, 8 Hz), 7.38-7.45 (4H, m), 7.62-7.65 (1H, m), 7.67 (1H, dd, J=8 Hz, 1 Hz), 7.76 (1H, d, J=8 Hz), 7.84 (1H, dd, J=8 Hz, 1 Hz), 8.00 (1H, d, J=8 Hz).

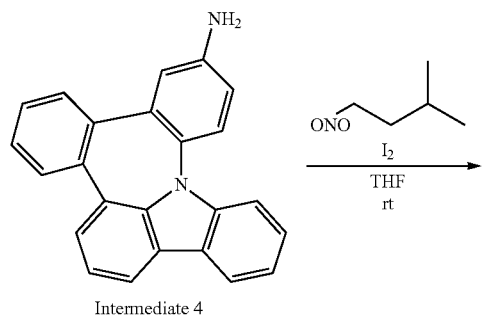
Intermediate 4

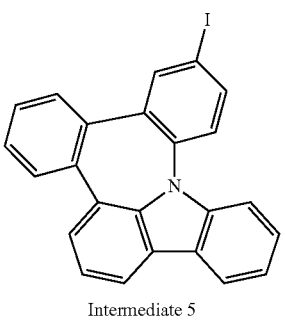
Intermediate 5

A mixture of the intermediate 4 (4.8 g) and 10 ml of THF was added with isopentyl nitrite (2.0 g) at room temperature and successively with a solution of iodine (5.5 g) in 10 ml of THF at room temperature. The reaction solution was added with water and sodium sulfite, and extracted with methylene dichloride. The extract was dried over anhydrous sodium sulfate. After removing the solvent by evaporation, the residue was purified by column chromatography to obtain the intermediate 5 (4.0 g).

$^1$H-NMR (400 MHz, CDCl$_3$, TMS):

δ 7.13 (1H, d, J=9 Hz), 7.32-7.48 (7H, m), 7.58-7.60 (1H, m), 7.68 (1H, dd, J=8 Hz, 1 Hz), 7.74 (1H, d, J=8 Hz), 7.79 (1H, d, J=3 Hz), 7.84 (1H, dd, J=8 Hz, 1 Hz), 8.00 (1H, d, J=8 Hz).

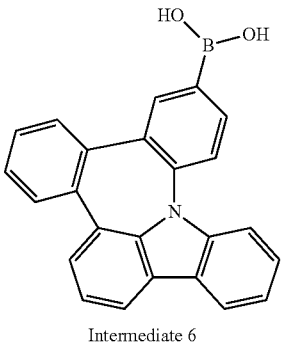
Intermediate 5

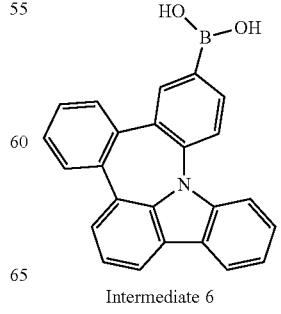
Intermediate 6

In a nitrogen atmosphere, a solution of the intermediate 5 (4.0 g) in 20 ml of THF was added with n-butyllithium (1.65 M, 6.6 ml) at −78° C. and stirred for one hour. After adding triisopropyl borate (3.1 ml) at −78° C. and stirring for 0.5 h, the reaction solution was added with water. After removing THF by evaporation, the solution was filtered to obtain the intermediate 6 as white solid (1.5 g).

$^1$H-NMR (400 MHz, acetone-d$_6$, TMS):

δ 7.29 (1H, s), 7.37-7.39 (3H, m), 7.48-7.54 (4H, m), 7.72-7.80 (3H, m), 7.88 (1H, d, J=8 Hz), 8.00 (1H, dd, J=7 Hz, 1 Hz), 8.07 (1H, d, J=1 Hz), 8.16 (1H, d, J=8 Hz).

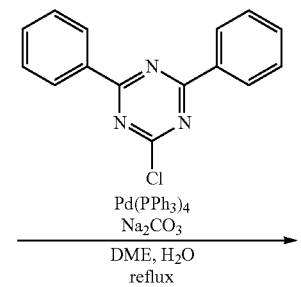
Intermediate 6

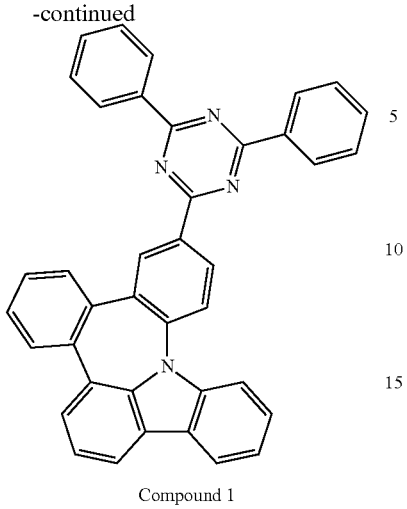

Compound 1

In a nitrogen atmosphere, a mixture of the intermediate 6 (1.5 g), 2-chloro-4,6-diphenyl-1,3,5-triazine (1.2 g), tetrakis(triphenylphosphine)palladium (0.10 g), and sodium carbonate (1.3 g) in 10 ml of DME and 5 ml water was refluxed under heating for 8 h. The reaction solution was added with water and extract with methylene dichloride, and the extract was dried over anhydrous sodium sulfate. After removing the solvent by evaporation, the residue was purified by column chromatography to obtain the compound 1 as white solid (1.6 g).

$^1$H-NMR (400 MHz, CDCl$_3$, TMS):
δ 7.37-7.63 (13H, m), 7.74 (1H, d, J=8 Hz), 7.84 (1H, dd, J=8 Hz, 1 Hz), 7.88 (2H, d, J=8 Hz), 8.05 (1H, d, J=7 Hz), 8.59 (1H, dd, J=9 Hz, 2 Hz), 8.74-8.77 (4H, m), 8.90 (1H, d, J=2 Hz).

The compound 1 thus obtained was measured for the maximum absorption wavelength, the maximum fluorescence wavelength, and the fluorescent quantum yield. The results are shown below. The maximum absorption wavelength was measured by U-3310 manufactured by Hitachi, Ltd. using a toluene solution of the compound 1. The maximum fluorescence wavelength was measured by F-7000 manufactured by Hitachi, Ltd. using a toluene solution of the compound 1. The fluorescent quantum yield was measured by C9920-02 manufactured by Hamamatsu Photonics K.K. using a toluene solution of the compound 1 (2×10$^{-5}$ mol/L) under excitation with 325 nm light.
Maximum absorption wavelength: 357 nm (toluene)
Maximum fluorescence wavelength: 448 nm (toluene)
Fluorescent quantum yield: 66% (2×10$^{-5}$ mol/L in toluene, excitation light: 325 nm)

Synthesis Example 2

Synthesis of Compound 2

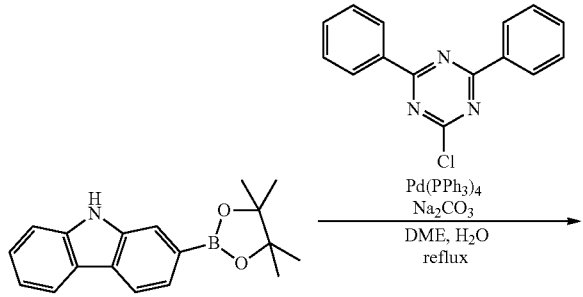

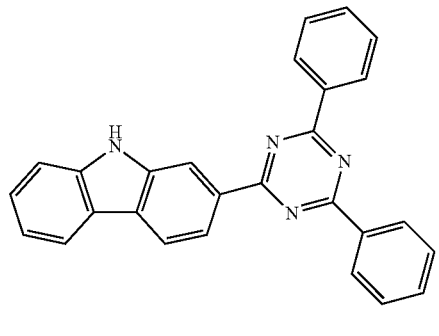

Intermediate 8

In a nitrogen atmosphere, a mixture of 2-(4,4,5,5-tetramethyl-1,3,2-dioxaborane-2-yl)-9H-carbazole (7.9 g), 2-chloro-4,6-diphenyl-1,3,5-triazine (6.5 g), tetrakis(triphenylphosphine)palladium (0.28 g), and sodium carbonate (7.7 g) in 30 ml of DME and 10 ml of water was refluxed under heating for 10 h. The reaction solution was added with water and extracted with methylene dichloride, and the extract was dried over anhydrous sodium sulfate. After removing the solvent by evaporation, the residue was purified by column chromatography to obtain the intermediate 8 as white solid (6.6 g).

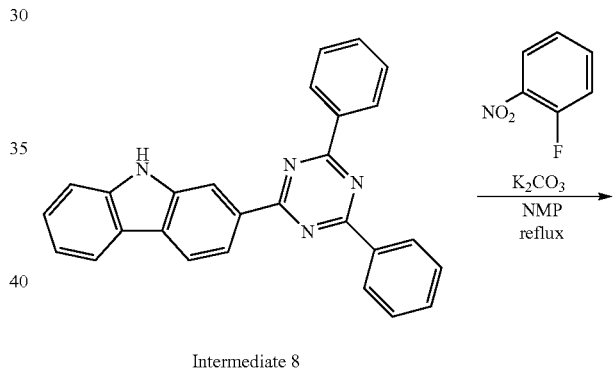

Intermediate 8

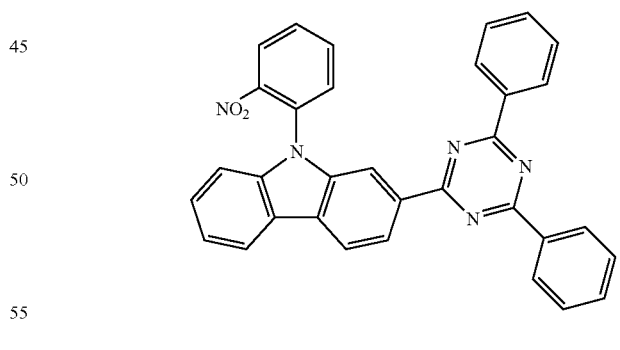

Intermediate 9

A mixture of the intermediate 8 (4.6 g), 2-fluoronitrobenzene (1.8 g), and potassium carbonate (3.2 g) in 20 ml of NMP was stirred at 150° C. for 2 h. The reaction solution was added with water and extracted with methylene dichloride, and the extract was dried over anhydrous sodium sulfate. After removing the solvent by evaporation, the residue was purified by column chromatography to obtain the intermediate 9 as yellow solid (6.0 g).

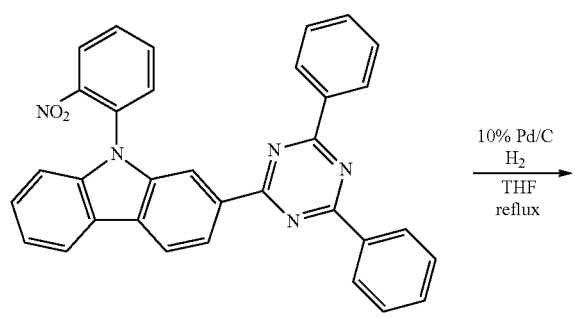

Intermediate 9

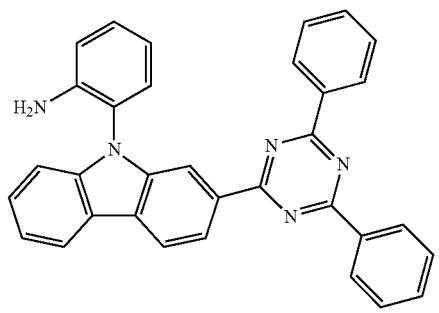

Intermediate 10

In a hydrogen atmosphere, a mixture of the intermediate 9 (6.0 g) and an activated carbon carrying 10% palladium (1.2 g) in 300 ml of THF was refluxed under heating for 5 h. The reaction solution was filtered and the solvent was removed by evaporation. The residue was purified by column chromatography to obtain the intermediate 10 as yellow solid (5.4 g).

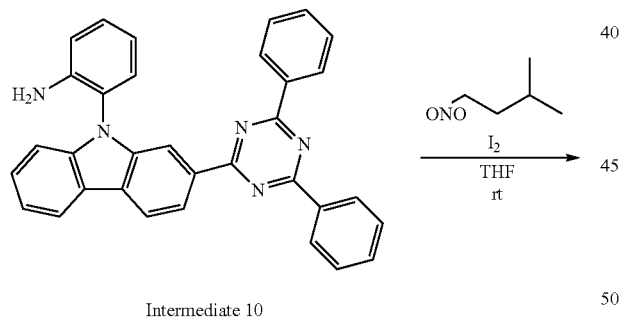

Intermediate 10

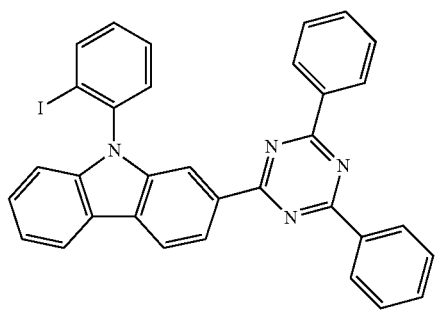

Intermediate 11

Into a mixture of the intermediate 10 (4.0 g) in 40 ml of THF, isopentyl nitrite (1.1 g) was added at room temperature, and a solution of iodine (2.1 g) in 5 ml of THF was successively added at room temperature. The reaction solution was added with water and sodium sulfite and extracted with methylene dichloride, and the extract was dried over anhydrous sodium sulfate. After removing the solvent by evaporation, the residue was purified by column chromatography to obtain the intermediate 11 as yellow solid (4.8 g).

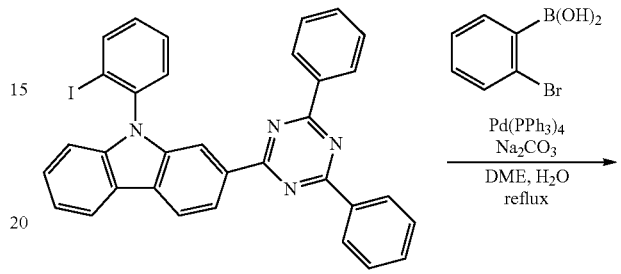

Intermediate 11

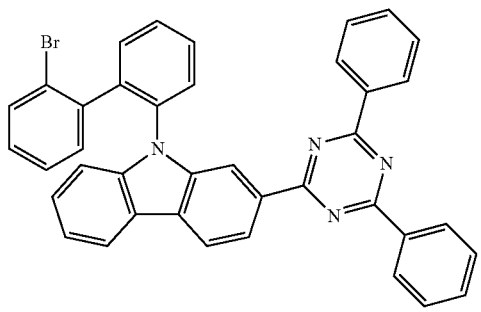

Intermediate 12

In a nitrogen atmosphere, a mixture of the intermediate 11 (4.8 g), 2-bromophenylboronic acid (1.6 g), palladium complex (0.20 g), and sodium carbonate (1.7 g) in 50 ml of DME and 25 ml of water was refluxed under heating for 0.5 h. The reaction solution was added with water and extracted with methylene dichloride, and the extract was dried over anhydrous sodium sulfate. After removing the solvent by evaporation, the residue was purified by column chromatography to obtain the intermediate 12 as yellow solid (5.0 g).

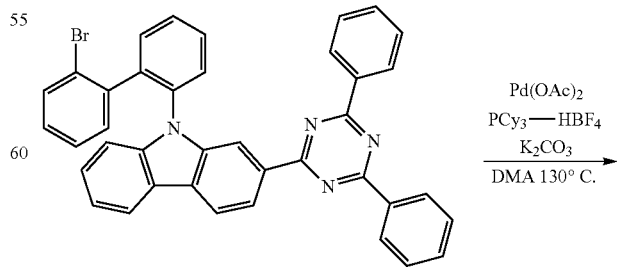

Intermediate 12

Synthesis Example 3

Synthesis of Compound X1

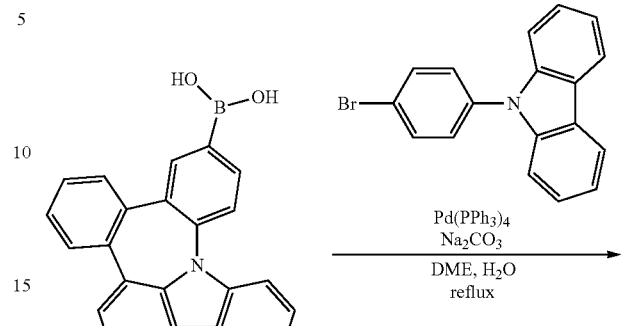

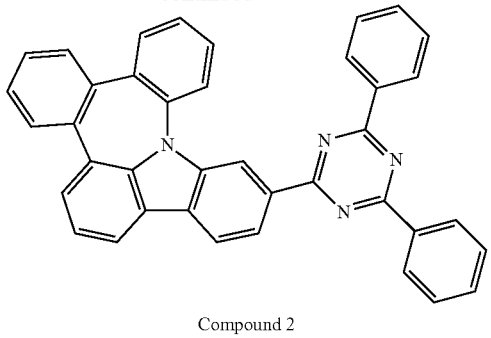

Compound 2

In a nitrogen atmosphere, a mixture of the intermediate 12 (5.0 g), palladium acetate (0.20 g), tricyclohexylphosphonium tetrafluoroborate (0.64 g), and potassium carbonate (2.4 g) in 50 ml DMA was stirred at 140° C. for 8 h. The reaction solution was added with water and extracted with methylene dichloride, and the extract was dried over anhydrous sodium sulfate. After removing the solvent by evaporation, the residue was purified by column chromatography to obtain the compound 2 as yellow solid (1.0 g).

$^1$H-NMR (400 MHz, CDCl$_3$, TMS):

δ 7.25-7.29 (2H, m), 7.41-7.52 (5H, m), 7.55-7.64 (7H, m), 7.70 (1H, dd, J=6 Hz, 2 Hz), 7.77 (1H, d, J=8 Hz), 7.95 (1H, d, J=7 Hz), 8.19 (1H, d, J=8 Hz), 8.78-8.82 (5H, m), 9.25 (1H, s)

The compound 2 thus obtained was measured for the maximum absorption wavelength, the maximum fluorescence wavelength, and the fluorescent quantum yield in the same manner as in the measurement for the compound 1. The results are shown below.

Maximum absorption wavelength: 342 nm (toluene)

Maximum fluorescence wavelength: 451 nm (toluene)

Fluorescent quantum yield: 35% (2×10$^{-5}$ mol/L in toluene, excitation light: 325 nm)

Reference Example

Upon irradiating a toluene solution of the following compound 3 (2×10$^{-5}$ mol/L) with a light of 300 nm, the emission of blue fluorescence with a maximum fluorescence wavelength of 466 nm was observed. This result shows that the compound having the following structure has an emission property useful as a fluorescent emitting material, particularly, as a blue fluorescent dopant.

Compound 3

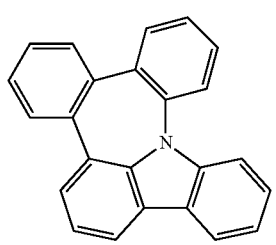

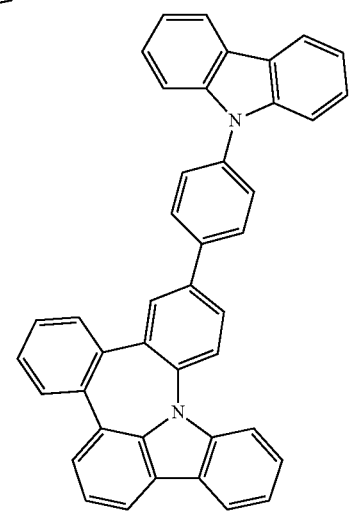

Compound X1

The compound X1 was obtained in the same manner as in the synthesis of the compound 1 except for using 9-(4-bromophenyl)carbazole in place of 2-chloro-4,6-diphenyl-1,3,5-triazine. The compound X1 was identified by the mass spectrometric analysis which showed m/e=558 (exact mass: 558.21).

Synthesis Example 4

Synthesis of Compound X2

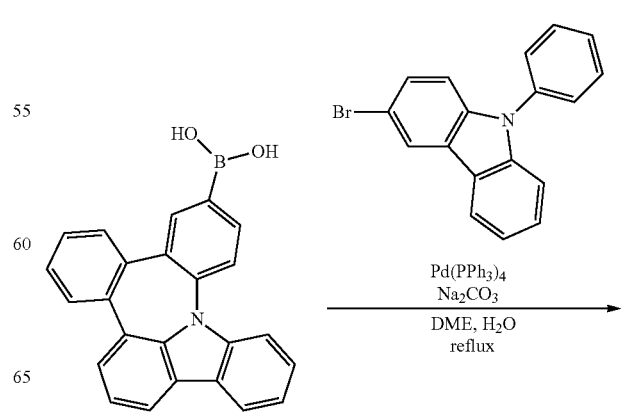

-continued

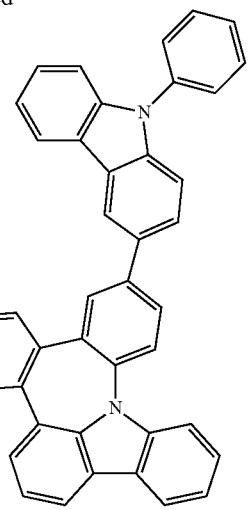

Compound X2

The compound X2 was obtained in the same manner as in the synthesis of the compound 1 except for using 3-bromo-9-phenylcarbazole in place of 2-chloro-4,6-diphenyl-1,3,5-triazine. The compound X2 was identified by the mass spectrometric analysis which showed m/e=558 (exact mass: 558.21).

Synthesis Example 5

Synthesis of Compound X3

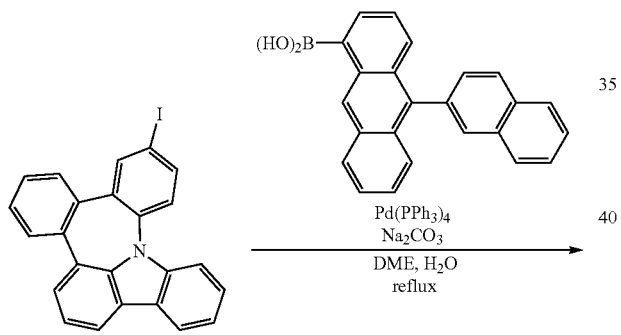

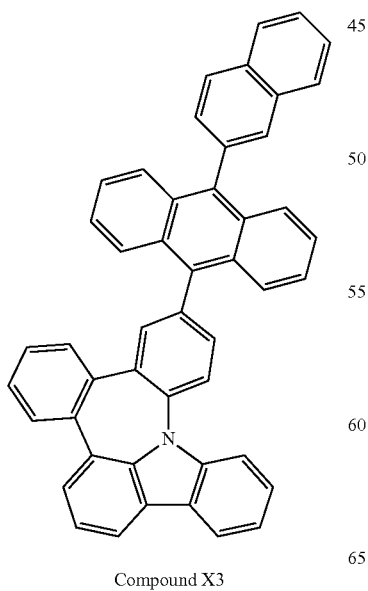

Compound X3

The compound X3 was obtained in the same manner as in the synthesis of the compound 1 except for using the intermediate 5 in place of 2-chloro-4,6-diphenyl-1,3,5-triazine and using (10-(4-(naphthalene-2-yl))anthracene-9-yl) boronic acid in place of the intermediate 6. The compound X3 was identified by the mass spectrometric analysis which showed m/e=619 (exact mass: 619.23).

Synthesis Example 6

Synthesis of Compound X4

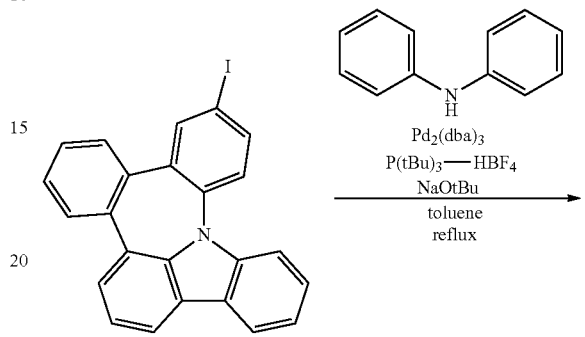

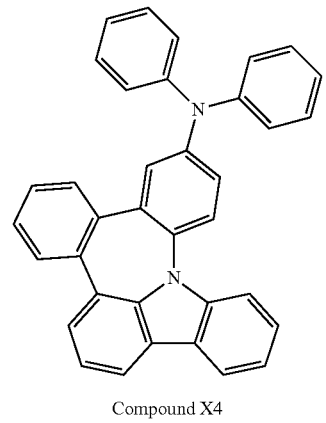

Compound X4

The compound X4 was obtained in the same manner as in the synthesis of the compound 1, while using the intermediate 5, diphenylamine, tris(dibenzylideneacetone)dipalladium(0), tri-tert-butylphosphine tetrafluoroborate, sodium tert-butoxide, and toluene. The compound X4 was identified by the mass spectrometric analysis which showed m/e=484 (exact mass: 484.19).

Synthesis Example 7

Synthesis of Compound X5

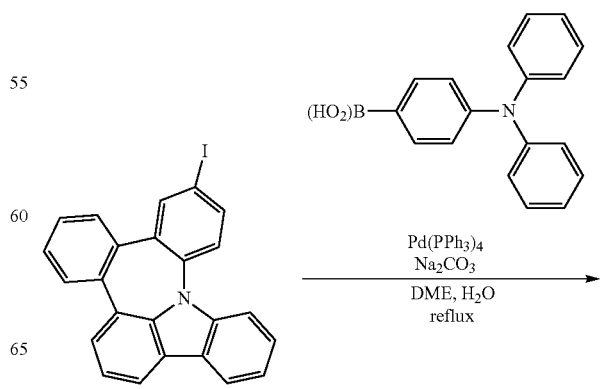

-continued

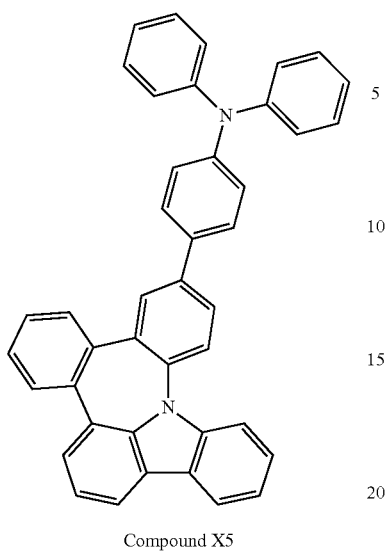

Compound X5

The compound X5 was obtained in the same manner as in the synthesis of the compound 1 except for using the intermediate 5 in place of 2-chloro-4,6-diphenyl-1,3,5-triazine and using triphenylamine-4-boronic acid in place of the intermediate 6. The compound X5 was identified by the mass spectrometric analysis which showed m/e=560 (exact mass: 560.23).

Synthesis Example 8

Synthesis of Compound X6

-continued

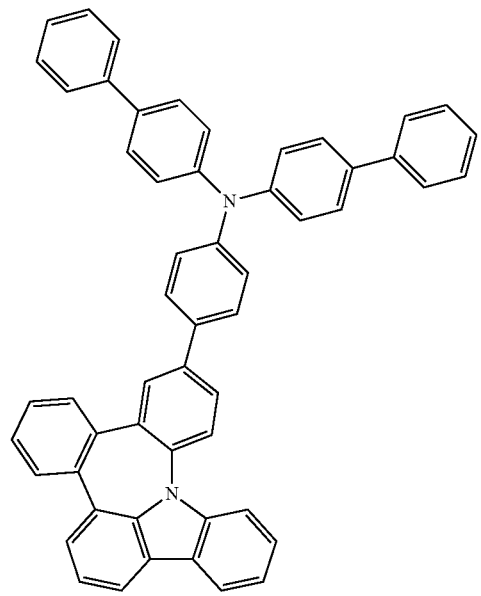

Compound X6

The compound X6 was obtained in the same manner as in the synthesis of the compound 1 except for using the intermediate 5 in place of 2-chloro-4,6-diphenyl-1,3,5-triazine and using 4-[N,N-bis(4-biphenyl)amino]phenylboronic acid in place of the intermediate 6. The compound X6 was identified by the mass spectrometric analysis which showed m/e=712 (exact mass: 712.29).

Synthesis Example 9

Synthesis of Compound X7

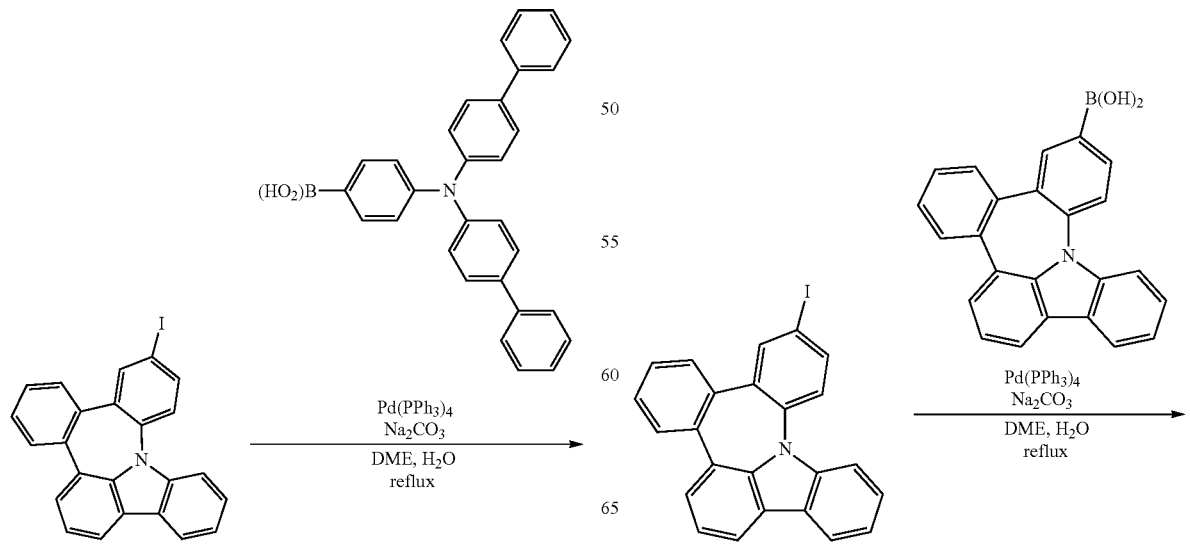

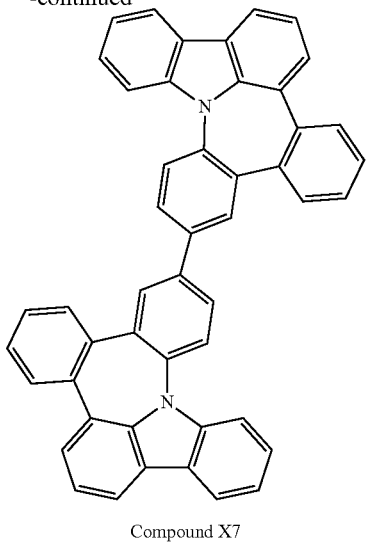

Compound X7

The compound X7 was obtained in the same manner as in the synthesis of the compound 1 except for using the intermediate 5 in place of 2-chloro-4,6-diphenyl-1,3,5-triazine. The compound X7 was identified by the mass spectrometric analysis which showed m/e=632 (exact mass: 632.23).

Synthesis Example 10

Synthesis of Compound X8

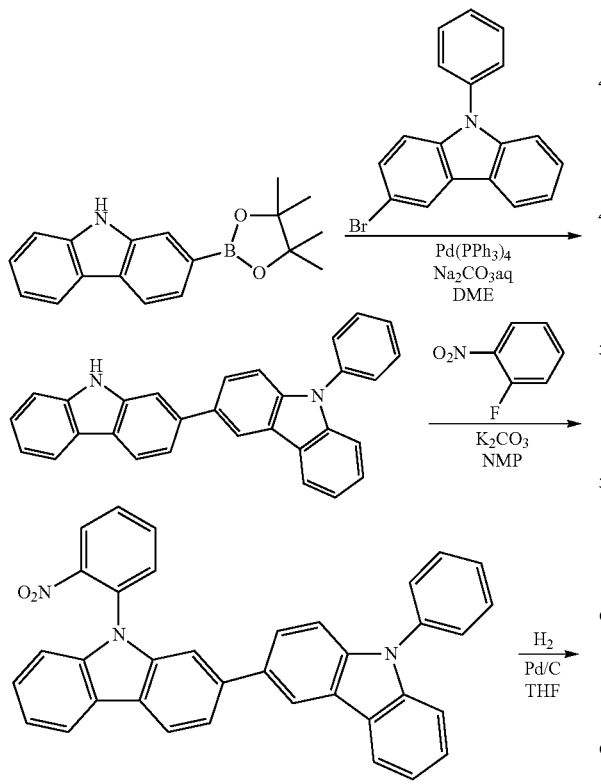

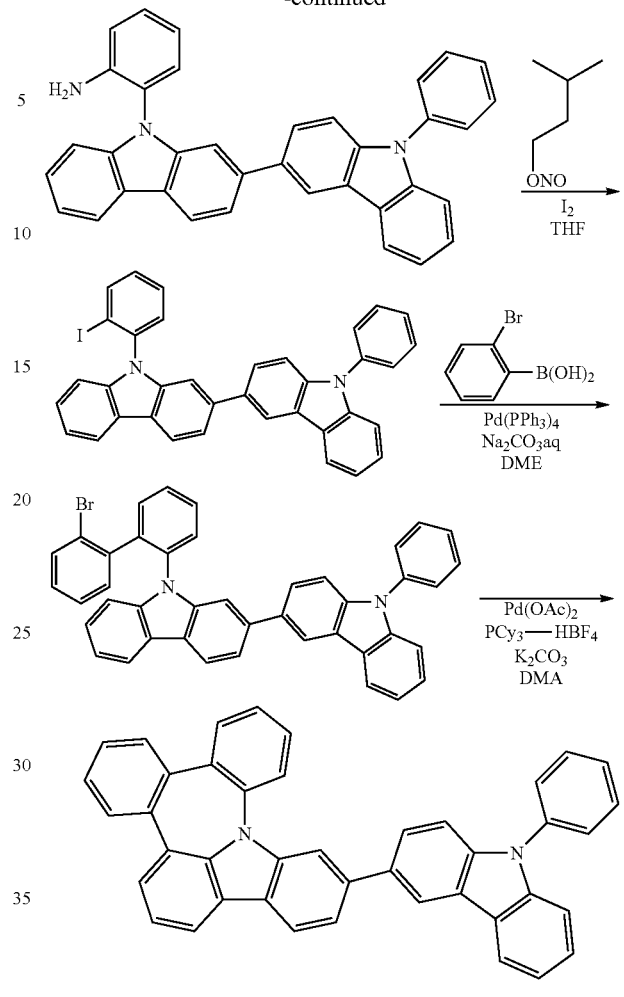

Compound X8

The compound X8 was synthesized in the same manner as in the synthesis of the compound 2 according to the above synthesis scheme. The compound X8 was identified by the mass spectrometric analysis which showed m/e=558 (exact mass: 558.21).

Example 1

Production of Organic EL Device

A glass substrate of 25 mm×75 mm×1.1 mm thickness having an ITO transparent electrode (product of Geomatec Company) was cleaned by ultrasonic cleaning in isopropyl alcohol for 5 min and then UV ozone cleaning for 30 min. The cleaned glass substrate was mounted to a substrate holder of a vacuum vapor deposition apparatus. The following compound HI-1 was vapor-deposited so as to cover the transparent electrode to form a compound HI-1 film with a thickness of 5 nm. On the compound HI-1 film, the following compound HT-1 (first hole transporting material) was vapor-deposited to form a first hole transporting layer with a thickness of 65 nm. Successively after forming the first hole transporting layer, the following compound HT-2 (second hole transporting material) was vapor-deposited to form a second hole transporting layer with a thickness of 10 nm.

On the second hole transporting layer, the compound 1 (host material) obtained in Synthesis Example 1 and Ir(bzq)$_3$ (phosphorescent emitting material) were co-deposited to form a phosphorescent light emitting layer with a thickness of 25 nm. The concentration of Ir(bzq)₃ in the light emitting layer was 10.0% by mass. The co-deposited film works as a light emitting layer.

Successively after forming the light emitting layer, the following compound ET-1 was vapor-deposited into a film with a thickness of 35 nm. The compound ET-1 film works as an electron transporting layer.

Then, LiF was vapor-deposited into a film with a thickness of 1 nm at a film-forming speed of 0.1 Å/min to form an electron injecting electrode (cathode). On the LiF film, metallic Al was vapor-deposited to form a metallic cathode with a thickness of 80 nm, thereby obtaining an organic EL device.

The compounds used in the examples and comparative examples are shown below.

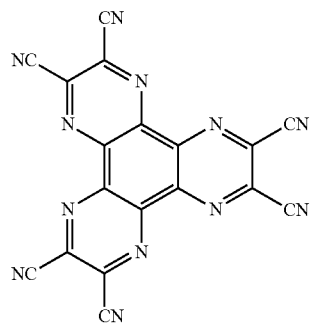

Compound HI-1

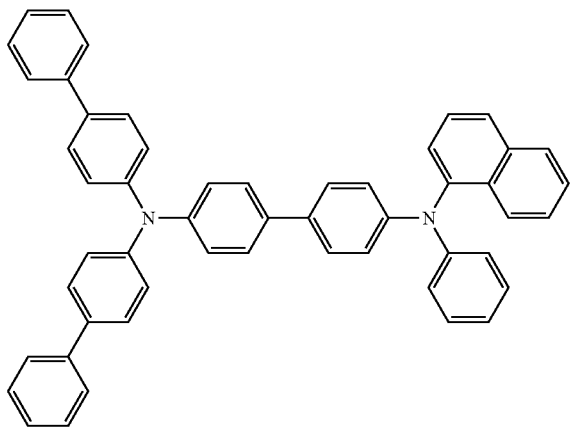

Compound HT-1

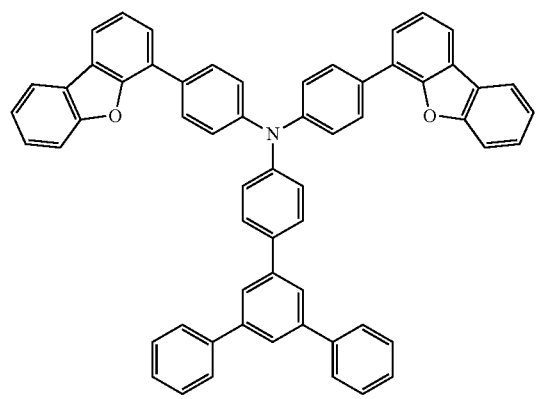

Compound HT-2

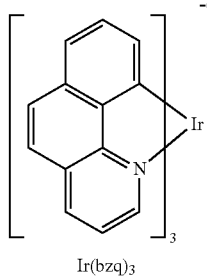

Ir(bzq)₃

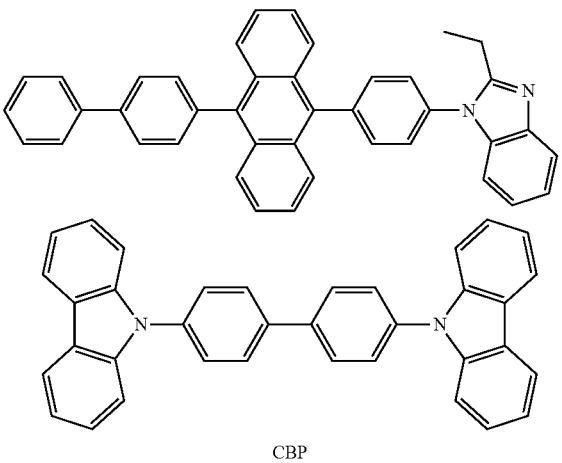

Compound ET-1

CBP

Evaluation of Emission Performance of Organic EL Device

The obtained organic EL device was measured for the emission efficiency at room temperature under constant DC driving (current density: 10 mA/cm²). The results are shown in Table 1.

Comparative Example 1

An organic EL device was produced in the same manner as in Example 1 except for forming the light emitting layer by using CBP as the host material in place of the compound 1. The results of the measured emission efficiency are shown in Table 1.

TABLE 1

| | Light emitting layer host material | Voltage (V) | Emission efficiency (cd/A) |
|---|---|---|---|
| Example 1 | Compound 1 | 3.31 | 57.07 |
| Comparative Example 1 | CBP | 5.67 | 38.68 |

REFERENCE NUMERALS

1: Organic electroluminescence device
2: Substrate
3: Anode
4: Cathode
5: Light emitting layer
6: Anode-side organic thin film layer
7: Cathode-side organic thin film layer
10: Organic thin film layers

What is claimed is:

1. A material for organic electroluminescence device comprising a nitrogen-containing heterocyclic compound A represented by formula (1):

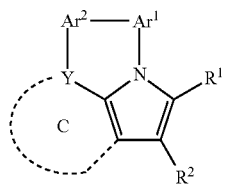

wherein:
- each of $R^1$ and $R^2$ independently represents a hydrogen atom or a group;
- when both $R^1$ and $R^2$ represent the groups, $R^1$ and $R^2$ may be bonded to each other to form a ring structure;
- each of $Ar^1$ and $Ar^2$ independently represents a substituted or unsubstituted arylene group having 6 to 50 ring carbon atoms or a substituted or unsubstituted heteroarylene group having 5 to 50 ring atoms;
- one of ring atoms of $Ar^1$ is bonded to $Ar^2$, and another ring atom of $Ar^1$ which is adjacent to the ring atom bonded to $Ar^2$ is bonded to a nitrogen atom shown in formula (1);
- one of ring atoms of $Ar^2$ is bonded to $Ar^1$, and another ring atom of $Ar^2$ which is adjacent to the ring atom bonded to $Ar^1$ is bonded to Y shown in formula (1);
- Y represents a carbon atom or a nitrogen atom; and
- C represents a substituted or unsubstituted aromatic hydrocarbon ring or a substituted or unsubstituted aromatic heterocyclic ring.

2. The material for organic electroluminescence device according to claim 1, wherein the nitrogen-containing heterocyclic compound A is represented by formula (2):

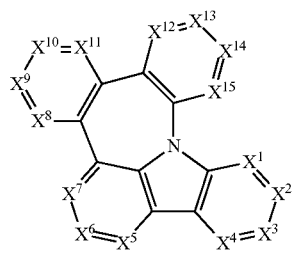

wherein:
- each of $X^1$ to $X^{15}$ independently represents C(R) or a nitrogen atom;
- R represents a hydrogen atom or a group; and
- when two or more of $X^1$ to $X^{15}$ have the group, the groups may be bonded to each other to form a ring structure.

3. The material for organic electroluminescence device according to claim 1, wherein the nitrogen-containing heterocyclic compound A is represented by formula (3):

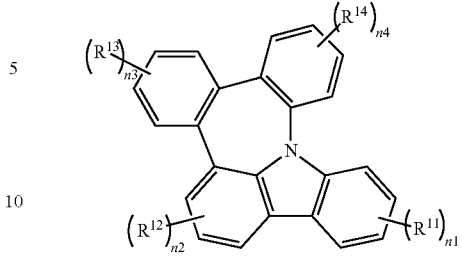

wherein:
- each of $R^{11}$ to $R^{14}$ independently represents a group;
- each of n1, n3, and n4 independently represents an integer of 0 to 4;
- n2 represents an integer of 0 to 3;
- when n1 represents 2 to 4, $R^{11}$ groups may be the same or different, and $R^{11}$ groups may be bonded to each other to form a ring structure;
- when n2 represents 2 or 3, $R^{12}$ groups may be the same or different, and $R^{12}$ groups may be bonded to each other to form a ring structure;
- when n3 represents 2 to 4, $R^{13}$ groups may be the same or different, and $R^{13}$ groups may be bonded to each other to form a ring structure; and
- when n4 represents 2 to 4, $R^{14}$ groups may be the same or different, and $R^{14}$ groups may be bonded to each other to form a ring structure.

4. The material for organic electroluminescence device according to claim 1, wherein each of the groups referred to in formulae (1) to (3) is independently selected from a substituted or unsubstituted alkyl group having 1 to 50 carbon atoms; a substituted or unsubstituted cycloalkyl group having 5 to 50 ring carbon atoms; a substituted or unsubstituted aryl group having 6 to 50 ring carbon atoms; an aralkyl group having 7 to 51 total carbon atoms having a substituted or unsubstituted aryl group having 6 to 50; an amino group; a mono- or di-substituted amino group having a substituent selected from a substituted or unsubstituted alkyl group having 1 to 50 carbon atoms and a substituted or unsubstituted aryl group having 6 to 50 ring carbon atoms; an alkoxy group having a substituted or unsubstituted alkyl group having 1 to 50 carbon atoms; an aryloxy group having a substituted or unsubstituted aryl group having 6 to 50 ring carbon atoms; a mono-, di- or tri-substituted silyl group having a substituent selected from a substituted or unsubstituted alkyl group having 1 to 50 carbon atoms and a substituted or unsubstituted aryl group having 6 to 50 ring carbon atoms; a substituted or unsubstituted heterocyclic group having 5 to 50 ring atoms; a substituted or unsubstituted haloalkyl group having 1 to 50 carbon atoms; a halogen atom; a cyano group; a nitro group; a sulfonyl group having a substituent selected from a substituted or unsubstituted alkyl group having 1 to 50 carbon atoms and a substituted or unsubstituted aryl group having 6 to 50 carbon atoms; and a di-substituted phosphoryl group having a substituent selected from a substituted or unsubstituted alkyl group having 1 to 50 carbon atoms and a substituted or unsubstituted aryl group having 6 to 50 ring carbon atoms.

5. An organic electroluminescence device comprising one or more organic thin film layers disposed between a cathode and an anode, wherein the organic thin film layers comprises a light emitting layer, and at least one layer of the organic thin film layers comprises the material for organic electroluminescence device according to claim 1.

6. The organic electroluminescence device according to claim 5, wherein the light emitting layer comprises the material for organic electroluminescence device.

7. The organic electroluminescence device according to claim 5, wherein the device comprises an anode-side organic thin film layer between the anode and the light emitting layer, and the anode-side organic thin film layer comprises the material for organic electroluminescence device.

8. The organic electroluminescence device according to claim 5, wherein the device comprises a cathode-side organic thin film layer between the cathode and the light emitting layer, and the cathode-side organic thin film layer comprises the material for organic electroluminescence device.

9. The organic electroluminescence device according to claim 5, wherein the light emitting layer comprises a phosphorescent emitting material.

10. The organic electroluminescence device according to claim 5, wherein the light emitting layer comprises a fluorescent emitting material.

11. The organic electroluminescence device according to claim 9, wherein the phosphorescent emitting material is an ortho-metallated complex comprising a metal selected from iridium (Ir), osmium (Os), and platinum (Pt).

12. A nitrogen-containing heterocyclic compound B represented by formula (1'):

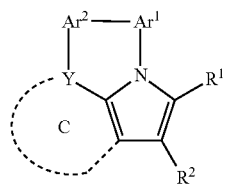

(1')

wherein:
each of $R^1$ and $R^2$ independently represents a hydrogen atom or a group;
when both $R^1$ and $R^2$ represent the groups, $R^1$ and $R^2$ may be bonded to each other to form a ring structure;
each of $Ar^1$ and $Ar^2$ independently represents a substituted or unsubstituted arylene group having 6 to 50 ring carbon atoms or a substituted or unsubstituted heteroarylene group having 5 to 50 ring atoms;
one of ring atoms of $Ar^1$ is bonded to $Ar^2$, and another ring atom of $Ar^1$ which is adjacent to the ring atom bonded to $Ar^2$ is bonded to a nitrogen atom shown in formula (1');
one of ring atoms of $Ar^2$ is bonded to $Ar^1$, and another ring atom of $Ar^2$ which is adjacent to the ring atom bonded to $Ar^1$ is bonded to Y shown in formula (1');
Y represents a carbon atom or a nitrogen atom; and
C represents a substituted or unsubstituted aromatic hydrocarbon ring or a substituted or unsubstituted aromatic heterocyclic ring;
provided that at least one of $R^1$, $R^2$, a substituent on $Ar^1$, a substituent on $Ar^2$, and a substituent on the aromatic hydrocarbon ring or the aromatic heterocyclic ring each represented by C is a group comprising a ring structure or a group comprising a reactive site.

13. The nitrogen-containing heterocyclic compound B according to claim 12, wherein the compound B is represented by formula (2'):

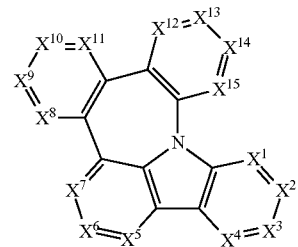

(2')

wherein:
each of $X^1$ to $X^{15}$ independently represents C(R) or a nitrogen atom;
R represents a hydrogen atom or a group; and
when two or more of $X^1$ to $X^{15}$ have the groups, the groups may be bonded to each other to form a ring structure;
provided that at least one of $X^1$ to $X^{15}$ represents C(R) wherein R represents a group comprising a ring structure or a group comprising a reactive site.

14. The nitrogen-containing heterocyclic compound B according to claim 12, wherein the compound B is represented by formula (3'):

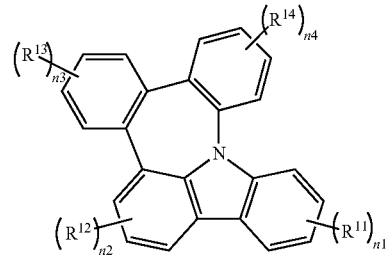

(3')

wherein:
each of $R^{11}$ to $R^{14}$ independently represents a group;
each of n1, n3 and n4 independently represents an integer of 0 to 4;
n2 represents an integer of 0 to 3;
when n1 represents 2 to 4, $R^{11}$ groups may be the same or different, and $R^{11}$ groups may be bonded to each other to form a ring structure;
when n2 represents 2 or 3, $R^{12}$ groups may be the same or different, and $R^{12}$ groups may be bonded to each other to form a ring structure;
when n3 represents 2 to 4, $R^{13}$ groups may be the same or different, and $R^{13}$ groups may be bonded to each other to form a ring structure; and
when n4 represents 2 to 4, $R^{14}$ groups may be the same or different, and $R^{14}$ groups may be bonded to each other to form a ring structure;
provided that formula (3') satisfies at least one of requirements (1) to (iv):
(i) n1 represents an integer of 1 to 4, and at least one of $R^{11}$ represents a group comprising a ring structure or a group comprising a reactive site;
(ii) n2 represents an integer of 1 to 3, and at least one of $R^{12}$ represents a group comprising a ring structure or a group comprising a reactive site;
(iii) n3 represents an integer of 1 to 4, and at least one of $R^{13}$ represents a group comprising a ring structure or a group comprising a reactive site; and (iv) n4 represents an integer of 1 to 4, and at least one of $R^{14}$ represents a group comprising a ring structure or a group comprising a reactive site.

15. The nitrogen-containing heterocyclic compound B according to claim 12, wherein the group comprising a ring structure is a substituted or unsubstituted aryl group having 6 to 50 ring carbon atoms; a group comprising a substituted or unsubstituted heteroaryl group having 5 to 50 ring atoms, or a mono- or di-substituted amino group having a substituted or unsubstituted aryl group having 6 to 50 ring carbon atoms.

16. The nitrogen-containing heterocyclic compound B according to claim 12, wherein the group comprising a reactive site comprises a reactive site selected from a halogen atom, an alkylsulfonyloxy group, an arylsulfonyloxy group, an alkylcarbonyloxy group, an arylcarbonyloxy group, a boron-containing group, a zinc-containing group, a tin-containing group, a silicon-containing group, a magnesium-containing group, a lithium-containing group, an amino group, a nitro group, a cyano group, a hydroxyl group, an alkyl-substitute or aryl-substituted carbonyl group, a carboxyl group, a vinyl group, a (meth)acryloyl group, an epoxy group, and an oxetanyl group.

17. The nitrogen-containing heterocyclic compound B according to claim 12, wherein each of the groups referred to in formulae (1') to (3') is independently selected from a substituted or unsubstituted alkyl group having 1 to 50 carbon atoms; a substituted or unsubstituted cycloalkyl group having 5 to 50 ring carbon atoms; a substituted or unsubstituted aryl group having 6 to 50 ring carbon atoms; an aralkyl group having 7 to 51 total carbon atoms having a substituted or unsubstituted aryl group having 6 to 50; an amino group; a mono- or di-substituted amino group having a substituent selected from a substituted or unsubstituted alkyl group having 1 to 50 carbon atoms and a substituted or unsubstituted aryl group having 6 to 50 ring carbon atoms; an alkoxy group having a substituted or unsubstituted alkyl group having 1 to 50 carbon atoms; an aryloxy group having a substituted or unsubstituted aryl group having 6 to 50 ring carbon atoms; a mono-, di- or tri-substituted silyl group having a substituent selected from a substituted or unsubstituted alkyl group having 1 to 50 carbon atoms and a substituted or unsubstituted aryl group having 6 to 50 ring carbon atoms; a substituted or unsubstituted heterocyclic group having 5 to 50 ring atoms; a substituted or unsubstituted haloalkyl group having 1 to 50 carbon atoms; a halogen atom; a cyano group; a nitro group; a sulfonyl group having a substituent selected from a substituted or unsubstituted alkyl group having 1 to 50 carbon atoms and a substituted or unsubstituted aryl group having 6 to 50 carbon atoms; and a di-substituted phosphoryl group having a substituent selected from a substituted or unsubstituted alkyl group having 1 to 50 carbon atoms and a substituted or unsubstituted aryl group having 6 to 50 ring carbon atoms.

18. An electronic equipment comprising the organic electroluminescence device according to claim 5.

* * * * *

UNITED STATES PATENT AND TRADEMARK OFFICE
CERTIFICATE OF CORRECTION

PATENT NO. : 9,502,667 B2
APPLICATION NO. : 14/163397
DATED : November 22, 2016
INVENTOR(S) : Masatoshi Saito et al.

Page 1 of 1

It is certified that error appears in the above-identified patent and that said Letters Patent is hereby corrected as shown below:

On the Title Page

Item (54) and in the Specification, Column 1, Line 1, should read:
-- MATERIAL FOR ORGANIC ELECTROLUMINESCENCE DEVICE, ORGANIC ELECTROLUMINESCENCE DEVICE EMPLOYING THE SAME, AND NITROGEN-CONTAINING HETEROCYCLIC COMPOUND --

Signed and Sealed this
Fourth Day of December, 2018

Andrei Iancu
*Director of the United States Patent and Trademark Office*